(12) United States Patent
Barbosa et al.

(10) Patent No.: US 7,981,881 B2
(45) Date of Patent: Jul. 19, 2011

(54) FUSED HETEROCYCLIC COMPOUNDS AND USE THEREOF

(75) Inventors: Joseph Barbosa, Lambertville, NJ (US);
William J. Pitts, Newtown, PA (US);
Junqing Guo, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 477 days.

(21) Appl. No.: 12/050,227

(22) Filed: Mar. 18, 2008

(65) Prior Publication Data

US 2008/0293650 A1 Nov. 27, 2008

Related U.S. Application Data

(62) Division of application No. 10/702,295, filed on Nov. 6, 2003, now Pat. No. 7,384,937.

(60) Provisional application No. 60/424,250, filed on Nov. 6, 2002.

(51) Int. Cl.
| A61P 19/00 | (2006.01) |
| A61K 31/55 | (2006.01) |
| A61K 31/535 | (2006.01) |
| A61K 31/497 | (2006.01) |
| A61K 31/519 | (2006.01) |
| C07D 413/00 | (2006.01) |
| C07D 487/00 | (2006.01) |

(52) U.S. Cl. ........ 514/212.08; 514/234.5; 514/252.16; 514/265.1; 540/524; 544/117; 544/280

(58) Field of Classification Search ............ 514/212.08, 514/234.5, 252.16, 265.1; 540/524; 544/117, 544/280
See application file for complete search history.

(56) References Cited

U.S. PATENT DOCUMENTS

| 5,212,291 A | 5/1993 | Murdock et al. |
| 5,527,896 A | 6/1996 | Wigler et al. |
| 5,726,302 A | 3/1998 | Ugarkar et al. |
| 5,733,913 A | 3/1998 | Blankley et al. |
| 5,733,914 A | 3/1998 | Blankley et al. |
| 5,977,305 A | 11/1999 | Wigler et al. |
| 6,028,183 A | 2/2000 | Lin et al. |

FOREIGN PATENT DOCUMENTS

| EP | 0 767 172 | 4/1997 |
| EP | 0 861 836 | 9/1998 |
| EP | 1 201 765 | 5/2000 |
| ES | 2 009 145 | 9/1989 |
| JP | 58-150503 | 9/1983 |
| WO | WO 98/13350 | 4/1998 |
| WO | WO 98/33798 | 8/1998 |
| WO | WO 01/28987 | 4/2001 |
| WO | WO 01/44258 | 6/2001 |
| WO | WO 01/55148 | 8/2001 |
| WO | WO 01/64679 | 9/2001 |

OTHER PUBLICATIONS

Han, P. et al., "Alternative Splicing of the High Affinity cAMP-Specific Phosphodiesterase (PDE7A) mRNA in Human Skeletal Muscle and Heart", The Journal of Biological Chemistry, vol. 272, No. 26, pp. 16152-16157 (1997).
Henry, J.R. et al., "p38 mitogen-activated protein kinase as a target for drug discovery", Drugs of the Future, vol. 24, No. 12, pp. 1345-1354 (1999).
Li, L. et al., "CD3- and CD28-Dependent Induction of PDE7 Required for T Cell Activation", Science, vol. 283, pp. 848-851 (1999).
Moreland, L.W. et al., "Etanercept Therapy in Rheumatoid Arthritis: A Randomized, Controlled Trial", Ann. Intern. Med., vol. 130, pp. 478-486 (1999).
Nakata, A. et al., "Potential role of phosphodiesterase 7 in human T cell function; comparative effects of two phosphodiesterase inhibitors", Clin. Exp. Immunol., vol. 128, pp. 460-466 (2002).
Rankin, E.C.C. et al., "The Therapeutic Effects of an Engineered Human Anti-Tumor Necrosis Factor Alpha Antibody (CDP571) in Rheumatoid Arthritis", British Journal of Rheumatology, vol. 34, pp. 334-342 (1995).
Salituro, F.G. et al., "Inhibitors of p38 MAP Kinase: Therapeutic Intervention in Cytokine-Mediated Diseases", Current Medicinal Chemistry, vol. 6, pp. 807-823 (1999).
Sasaki, T. et al., "Identification of Human PDE7B, a cAMP-Specific Phosphodiesterase", Biochemical and Biophysical Research Communications, vol. 271, pp. 575-583 (2000).

*Primary Examiner* — Brenda L Coleman
(74) *Attorney, Agent, or Firm* — Ying Wang; Laurelee A. Duncan

(57) ABSTRACT

Fused heterocylic compounds of the following Formula

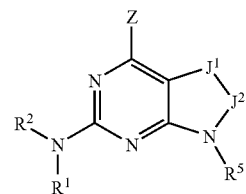

wherein $R^1$, $R^2$, $R^5$, $Z$, $J^1$ and $J^2$ are described herein, and analogs thereof are provided which are useful in treating leukocyte activation-associated disorders.

9 Claims, No Drawings

FUSED HETEROCYCLIC COMPOUNDS AND USE THEREOF

This application is a divisional of U.S. Ser. No. 10/702,295, filed Nov. 6, 2003 which claims priority from U.S. provisional application Ser. No. 60/424,250 filed Nov. 6, 2002, the entirety of which is incorporated herein by reference.

FIELD OF THE INVENTION

The present invention relates to fused heterocylic compounds, pharmaceutical compositions containing these compounds, and the use of these compounds in the treatment of leukocyte activation-associated disorders.

BACKGROUND OF THE INVENTION

The immune system plays an important role in host defense. In the treatment of leukocyte activation-associated disorders is often desirable to attenuate the immune response. Such disorders include the immune response incurred by transplantation or diseases improved by decreased T-cell activation and proliferation. It is accepted that agents that inhibit T-cell proliferation may be useful in the treatment of the aforementioned disorders.

A number of agents demonstrate clinical or therapeutic utility by attenuating or modulating the immune system. Such agents include Cyclosporin A ("CsA"), azathioprine, tacrolimus, sirolimus and mycophenolate mofetil. However, these agents often demonstrate a relatively high incidence (25 to >50%) of multiple unique liabilities during clinical or therapeutic use. For example, CsA therapy is associated with nephrotoxicity, azathioprine therapy is associated with leukopenia, and tacrolimus therapy is associated with undesirable effects on the central nervous system. Also, sirolimus therapy is associated with hypertension, hyperlipidemia and hypercholesterolemia, and mycophenolate mofetil therapy is associated with diarrhea.

The overproduction of cytokines, such as TNF-α, is also implicated in a wide variety of leukocyte activation-associated disorders, including rheumatoid arthritis (RA), psoriasis, multiple sclerosis, inflammatory bowel disease, endotoxin shock, osteoporosis, Alzheimer's disease and congestive heart failure, among others. See e.g., Henry et al., *Drugs Fut.*, 24:1345-1354 (1999); Salituro et al., *Curr. Med. Chem.*, 6:807-823 (1999). There is convincing evidence in human patients that cytokine protein antagonists can provide treatment for these disorders. See e.g., Rankin et al., *Br. J. Rheumatol.*, 34:334-342 (1995) (monoclonal antibody to TNF-α—Enbrel®); and Moreland et al., *Ann. Intern. Med.*, 130: 478-486 (1999) (soluble TNF-α receptor-Fc fusion protein—etanercept). Accordingly, it is accepted that agents demonstrating TNF-α inhibitory activity are useful for the treatment of leukocyte activation-associated disorders.

As none of the current treatments provide complete relief of symptoms and are often associated with various liabilities, new agents and improved methods for treating leukocyte activation-associated disorders are needed.

SUMMARY OF THE INVENTION

The present invention provides novel fused heterocyclic compounds of the following Formula (I), their enantiomers, diastereomers, and pharmaceutically acceptable salts, prodrugs and solvates thereof, for use in treating leukocyte activation-associated disorders:

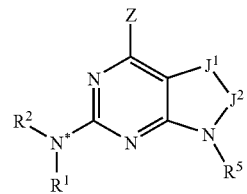

(I)

wherein:
$R^1$ is hydrogen or alkyl;
$R^2$ is
(a) heteroaryl or heterocyclo, either of which may be optionally independently substituted with one to three groups selected from $T^1$, $T^2$ and/or $T^3$;
(b) aryl substituted with one to three groups selected from $T^1$, $T^2$ and/or $T^3$ provided that at least one of $T^1$, $T^2$ and/or $T^3$ is other than H; or
(c) aryl fused to a heteroaryl or heterocyclo ring forming a fused ring system bound to N* through the aryl wherein the fused ring system may be optionally independently substituted with one to three groups selected from $T^1$, $T^2$ and/or $T^3$;
provided that $R^2$ is not

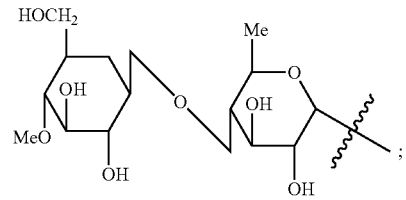

Z is $-NR^3R^4$, $-NR^3SO_2R^6$, $OR^4$, $SR^4$, haloalkyl or halogen;
$J^1$ is O, S, S(O), S(O)$_2$ or optionally substituted $C_{1-3}$ alkylene;
$J^2$ is carbonyl or optionally substituted $C_{1-3}$ alkylene, provided that $J^1$ and $J^2$ taken together do not form an alkylene chain of greater than 4 carbon atoms;
$R^3$ and $R^4$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which may be optionally independently substituted where valance allows with one to three groups $T^4$, $T^5$ and/or $T^6$, or $R^3$ and $R^4$ may be taken together with the nitrogen atom to which they are attached to form a heterocyclo or heteroaryl ring, either of which is optionally independently substituted where valance allows with one to three groups independently selected from $T^4$, $T^5$ and/or $T^6$;
$R^5$ is
(i) H, cyano, alkyl, alkenyl, alkynyl, cycloalkyl, (cycloalkyl)alkyl, aryl, (aryl)alkyl, heterocyclo, (heterocyclo)alkyl, heteroaryl or (heteroaryl)alkyl, any of which may be independently substituted where valance allows with one to three groups $T^7$, $T^8$ and/or $T^9$; or
(ii) $-C(O)_rR^7$, $-C(O)-C(O)-C(O)OR^7$ or $-SO_2R^8$;
$R^6$ is alkyl, alkenyl, aryl, (aryl)alkyl, heteroaryl, (heteroaryl)alkyl, cycloalkyl, (cycloalkyl)alkyl, heterocyclo, or (heterocyclo)alkyl, any of which may be optionally independently substituted where valance allows with one to three groups $T^4$, $T^5$ and/or $T^6$;

$R^7$ is
(i) H, alkyl, alkenyl, heterocyclo, (heterocyclo)alkyl, (hydroxy)alkyl, (alkoxy)alkyl, (aryloxy)alkyl, heteroaryl, aryl or (aryl)alkyl, any of which may be optionally independently substituted where valance allows with one to three groups $T^7$, $T^8$ and/or $T^9$; or
(ii) —$NR^9R^{10}$ or ($NR^9R^{10}$)alkyl;

$R^8$ is
(i) alkyl, alkenyl, heterocyclo, (heterocyclo)alkyl, (hydroxy)alkyl, (alkoxy)alkyl, (aryloxy)alkyl, heteroaryl, aryl or (aryl)alkyl, any of which may be optionally independently substituted where valance allows with one to three groups $T^7$, $T^8$ and/or $T^9$; or
(ii) —$NR^9R^{10}$ or ($NR^9R^{10}$)alkyl;

$R^9$ and $R^{10}$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which may be optionally independently substituted where valance allows with one to three groups $T^7$, $T^8$ and/or $T^9$;

$T^1$-$T^9$ are each independently
(i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, aryl, (aryl)alkyl, heterocyclo, (heterocyclo)alkyl, heteroaryl, (heteroaryl)alkyl, —$OT^{10}$, —SH, —$ST^{10}$, —$C(O)_tH$, —$C(O)_tT^{10}$, —O—$C(O)T^{10}$, $T^{17}C(O)_tN(T^{11})T^{10}$, —$SO_3H$, —$S(O)_tT^{10}$, $S(O)_tN(T^{11})T^{10}$, -$T^{12}$-$NT^{14}T^{15}$, -$T^{12}$—$N(T^{11})$-$T^{13}$-$NT^{14}T^{15}$, -$T^{12}$-$N(T^{16})$-$T^{15}$-$T^{10}$ and -$T^{12}$-$N(T^{16})$-$T^{13}$-H; or
(ii) halo, cyano, nitro, OH, oxo, —SH, amino, —$OT^{10}$, —$ST^{10}$, —$C(O)_tH$, —$C(O)_tT^{10}$, —O—$C(O)T^{10}$, $T^{17}C(O)_tN(T^{11})T^{10}$, —$SO_3H$, —$S(O)_tT^{10}$, $S(O)_tN(T^{11})T^{10}$, -$T^{12}$-$NT^{14}T^{15}$, -$T^{12}$-$N(T^{11})$-$T^{13}$-$NT^{14}T^{15}$, -$T^{12}$-$N(T^{16})$-$T^{15}$-$T^{10}$ or -$T^{12}$-$N(T^{16})$-$T^{13}$-H;

t is 1 or 2;

$T^{10}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{12}$ and $T^{13}$ are each independently a single bond, -$T^{17}$-$S(O)_t$-$T^{18}$-, -$T^{17}$-$C(O)$-$T^{18}$-, -$T^{17}$-$C(S)$-$T^{18}$-, -$T^{17}$-O-$T^{18}$-, -$T^{17}$-S-$T^{18}$-, -$T^{17}$O—$C(O)$-$T^8$-, -$T^{17}$-$C(O)_tT^{18}$-, -$T^{17}$-C(=$NT^{19}$)-$T^{18}$- or -$T^{17}$-$C(O)$—$C(O)$-$T^{18}$-;

$T^{11}$, $T^{14}$, $T^{15}$, $T^{16}$ and $T^{19}$ are each independently
(i) hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —$ST^{22}$, —$C(O)_tH$, —$C(O)_tT^{22}$, —O—$C(O)T^{22}$ and —$S(O)_tT^{22}$; or
(ii) halo, cyano, nitro, OH, oxo, —SH, amino, —$OT^{22}$, —$ST^{22}$, —$C(O)_tH$, —$C(O)_tT^{22}$, —O—$C(O)T^{22}$, —$SO_3H$ or —$S(O)_tT^{22}$; or
(iii) $T^{14}$ and $T^{15}$ may together be alkylene or alkenylene, completing a 3- to 8-membered saturated or unsaturated ring together with the atoms to which they are attached, which ring is substituted with one or more groups listed in the description of $T^{20}$; or
(iv) $T^{14}$ or $T^{15}$ together with $T^{11}$, may be alkylene or alkenylene completing a 3- to 8-membered saturated or unsaturated ring together with the nitrogen atoms to which they are attached, which ring is substituted with one or more groups listed in the description of $T^{20}$; or
(v) $T^{14}$ and $T^{15}$ or $T^{11}$ and $T^{16}$ together with the nitrogen atom to which they are attached may combine to form a group —N=$CT^{20}T^{21}$;

$T^{17}$ and $T^{18}$ are each independently a single bond, alkylene, alkenylene or alkynylene;

$T^{20}$ and $T^{21}$ are each
(i) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —$ST^{22}$, —$C(O)_tH$, —$C(O)_tT^{22}$, —O—$C(O)T^{22}$ and —$S(O)_tT^{22}$; or
(ii) halo, cyano, nitro, OH, oxo, —SH, amino, —$OT^{22}$, —$ST^{22}$, —$C(O)_tH$, —$C(O)_tT^{22}$, —O—$C(O)T^{22}$, —$SO_3H$, —$S(O)_tT^{22}$, $S(O)_tN(T^{11})T^{22}$;

$T^{22}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl.

The following are definitions of the terms as used throughout this specification and claims. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred.

The term "substituted alkyl" refers to alkyl groups substituted with one or more groups listed in the definition of $T^1$-$T^9$, preferably selected from halo, cyano, O—$R_{11}$, S—$R_{11}$, $NR_{12}R_{13}$, nitro, cycloalkyl, substituted cycloalkyl, oxo, aryl, substituted aryl, heterocyclo, heteroaryl, $CO_2R_{11}$, $S(O)R_{11}$, $SO_2R_{11}$, $SO_3R_{11}$, $SO_2NR_{12}R_{13}$, $C(O)NR_{12}R_{13}$, C(O)alkyl and C(O)H.

The term "alkylene" refers to a straight chain bridge of 1 to 4 carbon atoms connected by single bonds (e.g., —(CH$_2$)$_x$— wherein x is 1 to 5), which may be substituted with one or more groups listed in the definition of $T^1$-$T^9$.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl.

The term "substituted alkenyl" refers to an alkenyl group as defined above substituted with one or more groups listed in the definition of $T^1$-$T^9$, preferably selected from halo, cyano, O—$R_{11}$, S—$R_{11}$, $NR_{12}R_{13}$, nitro, cycloalkyl, substituted cycloalkyl, oxo, aryl, substituted aryl, heterocyclo, heteroaryl, $CO_2R_{11}$, $S(O)R_{11}$, $SO_2R_{11}$, $SO_3R_{11}$, $SO_2NR_{12}R_{13}$, $C(O)NR_{12}R_{13}$, C(O)alkyl and C(O)H.

The term "alkynyl" refers to straight or branched chain hydrocarbon group having 2 to 12 carbon atoms and one, two or three triple bonds, preferably 2 to 6 carbon atoms and one triple bond.

The term "substituted alkynyl" refers to an alkynyl group as defined above substituted with one or more groups listed in the definition of $T^1$-$T^9$, preferably selected from halo, cyano, O—$R_{11}$, S—$R_{11}$, $NR_{12}R_{13}$, nitro, cycloalkyl, substituted cycloalkyl, oxo, aryl, substituted aryl, heterocyclo, heteroaryl, $CO_2R_{11}$, $S(O)R_{11}$, $SO_2R_{11}$, $SO_3R_{11}$, $SO_2NR_{12}R_{13}$, $C(O)NR_{12}R_{13}$, $C(O)_t$alkyl and C(O)H.

The term "carbonyl" refers to C=O, which may also be designated as C(O).

The group —$C(O)_tX$ refers to C(O)X where t is 1 and the structure

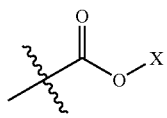

where t is 2.

The term "halo" refers to chloro, bromo, fluoro and iodo.

The term "cycloalkyl" refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons, preferably 3 to 7 carbons, forming the ring and which may be fused to 1 or 2 aromatic or heterocyclo rings, which include cyclopropyl, cyclobutyl, cyclopentyl, cyclohexyl, cycloheptyl, cyclooctyl, cyclodecyl, cyclododecyl, cyclohexenyl,

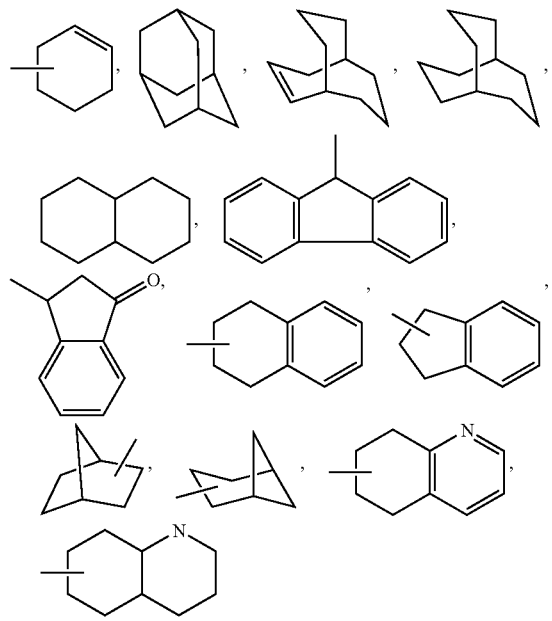

and the like.

The term "substituted cycloalkyl" refers to such cycloalkyl group as defined above substituted with one or more groups listed in the definition of $T^1$-$T^9$ preferably selected from halogen, nitro, alkyl, substituted alkyl, alkenyl, cyano, cycloalkyl, substituted cycloalkyl, aryl, substituted aryl, heterocyclo, heteroaryl, oxo, $OR_{11}$, $CO_2R_{11}$, $C(O)NR_{12}R_{13}$, $OC(O)R_{11}$, $OC(O)OR_{11}$, $OC(O)NR_{12}R_{13}$, $OCH_2CO_2R_{11}$, $C(O)R_{11}$, $NR_{12}R_{13}$, $NR_{14}C(O)R_{11}$, $NR_{14}C(O)OR_{11}$, $NR_{14}C(O)C(O)OR_{11}$, $NR_{14}C(O)C(O)NR_{12}R_{13}$, $NR_{14}C(O)C(O)$alkyl, $NR_{14}C(NCN)OR_{11}$, $NR_{14}C(O)NR_{12}R_{13}$, $NR_{14}C(NCN)NR_{12}R_{13}$, $NR_{14}C(NR_{15})NR_{12}R_{13}$, $NR_{14}SO_2NR_{12}R_{13}$, $NR_{14}SO_2R_{11}$, $SR_{11}$, $S(O)R_{11}$, $SO_2R_{11}$, $SO_3R_{11}$, $SO_2NR_{12}R_{13}$, $NHOR_{11}$, $NR_{14}NR_{12}R_{13}$, $N(COR_{11})OR_{14}$, $N(CO_2R_{11})OR_{14}$, $C(O)NR_{14}(CR_{16}R_{11})_rR_{11}$, $CO(CR_{16}R_{17})_pO(CR_{12}R_{13})_qCO_2R_{11}$, $CO(CR_{16}R_{17})_rOR_{11}$, $CO(CR_{16}R_{17})_pO(CR_{18}R_{13})_qR_{11}$, $CO(CR_{16}R_{17})_rNR_{12}R_{13}$, $OC(O)O(CR_{16}R_{17})_mNR_{12}R_{13}$, $OC(O)N(CR_{16}R_{17})_rR_{11}$, $O(CR_{16}R_{17})_m NR_{12}R_{13}$, $NR_{14}C(O)(CR_{16}R_{17})_rR_{11}$, $NR_{14}C(O)(CR_{16}R_{17})_r OR_{11}$, $NR_{14}C(=NC)(CR_{16}R_{17})_rR_{11}$, $NR_{14}CO(CR_{16}R_{17})_r NR_{12}R_{13}$, $NR_{14}(CR_{16}R_{17})_mOR_{11}$, $NR_{14}(CR_{16}R_{17})_rCO_2R_{11}$, $NR_{14}(CR_{16}R_{17})_m NR_{12}R_{13}$, $NR_{14}(CR_{16}R_{17})_nSO_2(CR_{18}R_{13})_q R_{11}$, $CONR_{14}(CR_{16}R_{17})_nSO_2(CR_{18}R_{13})_qR_{11}$, $SO_2NR_{14}(CR_{16}R_{17})_nCO(CR_{18}R_{19})_qR_{11}$ and $SO_2NR_{14}(CR_{16}R_{17})_m OR_{11}$.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl, as well as such rings fused to a cycloalkyl, cycloalkenyl, heterocyclo, or heteroaryl ring. Examples include:

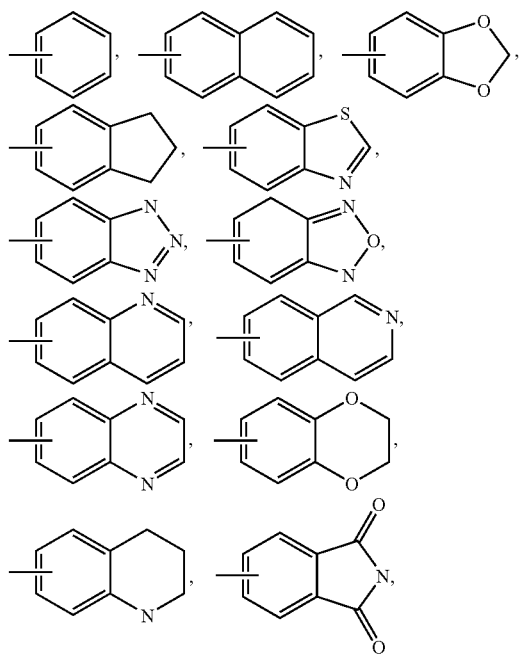

and the like.

The term "substituted aryl" refers to such aryl groups as defined above substituted with one or more groups listed in the definition of $T^1$-$T^9$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_{11}$, $CO_2R_{11}$, $C(O)NR_{12}R_{13}$, $OC(O)R_{11}$, $OC(O)OR_{11}$, $OC(O)NR_{12}R_{13}$, $OCH_2CO_2R_{11}$, $C(O)R_{11}$, $NR_{12}R_{13}$, $NR_{14}C(O)R_{11}$, $NR_{14}C(O)OR_{11}$, $NR_{14}C(O)C(O)OR_{11}$, $NR_{14}C(O)C(O)NR_{12}R_{13}$, $NR_{14}C(O)C(O)$alkyl, $NR_{14}C(NCN)OR_{11}$, $NR_{14}C(O)NR_{12}R_{13}$, $NR_{14}C(NCN)NR_{12}R_{13}$, $NR_{14}C(NR_{15})NR_{12}R_{13}$, $NR_{14}SO_2NR_{12}R_{13}$, $NR_{14}SO_2R_{11}$, $SR_{11}$, $S(O)R_{11}$, $SO_2R_{11}$, $SO_3R_{11}$, $SO_2NR_{12}R_{13}$, $NHOR_{11}$, $NR_{14}NR_{12}R_{13}$, $N(COR_{11})OR_{14}$, $N(CO_2R_{11})OR_{14}$, $C(O)NR_{14}(CR_{16}R_{17})_rR_{11}$, $CO(CR_{16}R_{17})_p$ $O(CR_{12}R_{13})_qCO_2R_{11}$, $CO(CR_{16}R_{17})_rOR_{11}$, $CO(CR_{16}R_{17})_p$ $O(CR_{18}R_{19})_qR_{11}$, $CO(CR_{16}R_{17})_rNR_{12}R_{13}$, $OC(O)O$ $(CR_{16}R_{17})_mNR_{12}R_{13}$, $OC(O)N(CR_{16}R_{17})_rR_{11}$, $O(CR_{16}R_{17})_m$ $NR_{12}R_{13}$, $NR_{14}C(O)(CR_{16}R_{17})_rR_{11}$, $NR_{14}C(O)(CR_{16}R_{17})_r$ $OR_{11}$, $NR_{14}C(=NC)(CR_{16}R_{17})_rR_{11}$, $NR_{14}CO(CR_{16}R_{17})_rNR_{12}R_{13}$, $NR_{14}(CR_{16}R_{17})_mOR_{11}$, $NR_{14}(CR_{16}R_{17})_rCO_2R_{11}$, $NR_{14}(CR_{16}R_{17})_mNR_{12}R_{13}$, $NR_{14}(CR_{16}R_{17})_nSO_2(CR_{18}R_{13})_q$ $R_{11}$, $CONR_{14}(CR_{16}R_{17})_nSO_2(CR_{18}R_{19})_qR_{11}$, $SO_2NR_{14}(CR_{16}R_{17})_nCO(CR_{18}R_{19})_qR_{11}$ and $SO_2NR_{14}(CR_{16}R_{17})_m OR_{11}$ as well as pentafluorophenyl.

The terms "heterocycle", "heterocyclic", "heterocyclic group" or "heterocyclo" refer to fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions. Exemplary heterocyclic groups include

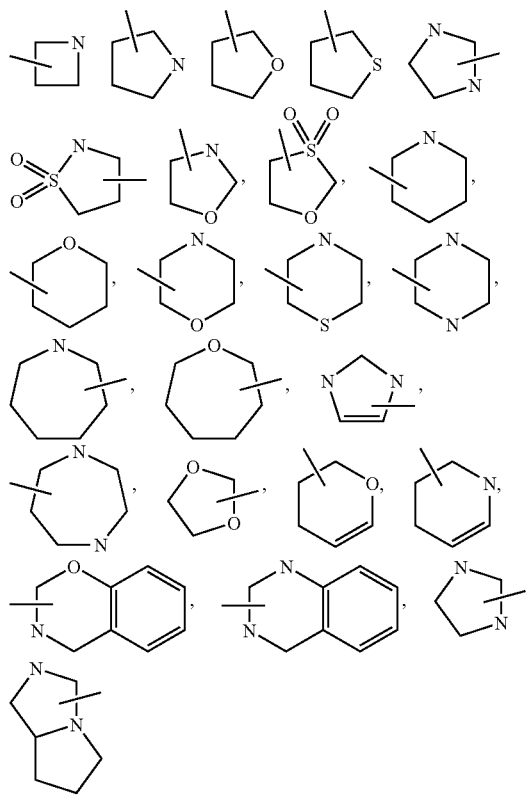

and the like.

The terms "substituted heterocycle" or "substituted heterocyclo" and the like refer to such heterocyclo groups as defined above substituted with one or more groups listed in the definition of $T^1$-$T^9$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_{11}$, $CO_2R_{11}$, $C(O)NR_{12}R_{13}$, $OC(O)R_{11}$, $OC(O)OR_{11}$, $OC(O)NR_{12}R_{13}$, $OCH_2CO_2R_{11}$, $C(O)R_{11}$, $NR_{12}R_{13}$, $NR_{14}C(O)R_{11}$, $NR_{14}C(O)OR_{11}$, $NR_{14}C(O)C(O)OR_{11}$, $NR_{14}C(O)C(O)NR_{12}R_{13}$, $NR_{14}C(O)C(O)alkyl$, $NR_{14}C(NCN)OR_{11}$, $NR_{14}C(O)NR_{12}R_{13}$, $NR_{14}C(NCN)NR_{12}R_{13}$, $NR_{14}C(NR_{15})NR_{12}R_{13}$, $NR_{14}SO_2NR_{12}R_{13}$, $NR_{14}SO_2R_{11}$, $SR_{11}$, $S(O)R_{11}$, $SO_2R_{11}$, $SO_3R_{11}$, $SO_2NR_{12}R_{13}$, $NHOR_{11}$, $NR_{14}NR_{12}R_{13}$, $N(COR_{11})OR_{14}$, $N(CO_2R_{11})OR_{14}$, $C(O)NR_{14}(CR_{16}R_{17})_rR_{11}$, $CO(CR_{16}R_{17})_pO(CR_{18}R_{13})_qCO_2R_{11}$, $CO(CR_{16}R_{17})_rOR_{11}$, $CO(CR_{16}R_{17})_pO(CR_{18}R_{19})_qR_{11}$, $CO(CR_{16}R_{17})_rNR_{12}R_{13}$, $OC(O)O(CR_{16}R_{17})_mNR_{12}R_{13}$, $OC(O)N(CR_{16}R_{17})_rR_{11}$, $O(CR_{16}R_{17})_mNR_{12}R_{13}$, $NR_{14}C(O)(CR_{16}R_{17})_rR_{11}$, $NR_{14}C(O)(CR_{16}R_{17})_rOR_{11}$, $NR_{14}C(=NC)(CR_{16}R_{17})_rR_{11}$, $NR_{14}CO(CR_{16}R_{17})_rNR_{12}R_{13}$, $NR_{14}(CR_{16}R_{17})_mOR_{11}$, $NR_{14}(CR_{16}R_{17})_rCO_2R_{11}$, $NR_{14}(CR_{16}R_{17})_mNR_{12}R_{13}$, $NR_{14}(CR_{16}R_{17})_nSO_2(CR_{18}R_{13})_qR_{11}$, $CONR_{14}(CR_{16}R_{17})_nSO_2(CR_{18}R_{19})_qR_{11}$, $SO_2NR_{14}(CR_{16}R_{17})_nCO(CR_{18}R_{19})_qR_{11}$ and $SO_2NR_{14}(CR_{16}R_{17})_m OR_{11}$.

The term "heteroaryl" as used herein alone or as part of another group refers to a 5- 6- or 7-membered aromatic rings containing from 1 to 4 nitrogen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are such rings fused to a cycloalkyl, aryl, cycloheteroalkyl, or another heteroaryl ring. One, two, or three available carbon or nitrogen atoms in the heteroaryl ring can be optionally substituted with substituents listed in the definition of $T^1$-$T^9$. Also an available nitrogen or sulfur atom in the heteroaryl ring can be oxidized. Examples of heteroaryl rings include

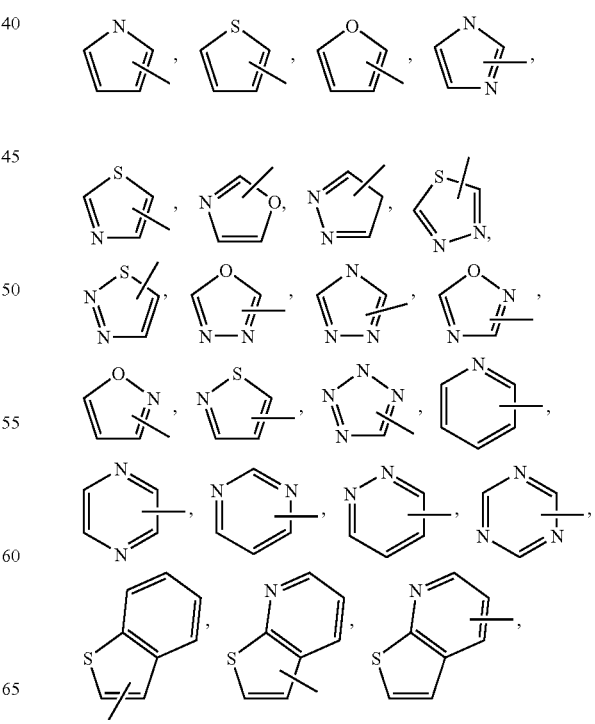

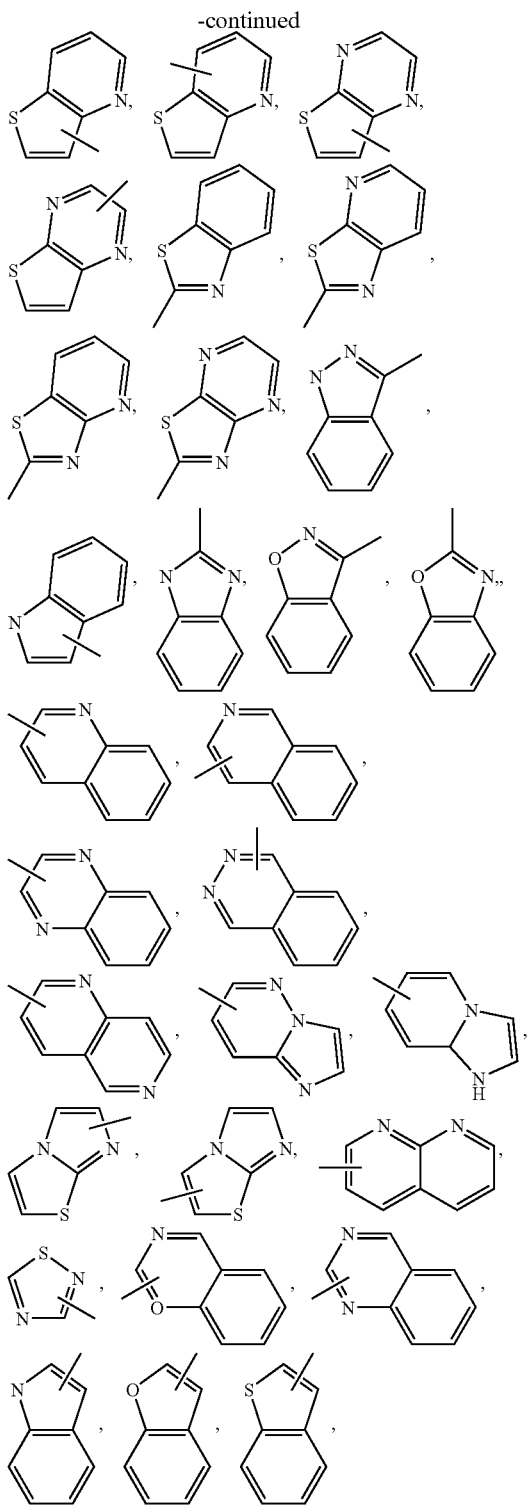

and the like.

The term "substituted heteroaryl" refers to such heteroaryl groups as defined above substituted on any available atom with one or more groups listed in the definition of $T^1$-$T^9$, "preferably selected from" refers to such heterocyclo groups as defined above substituted with one or more groups listed in the definition of $T^1$-$T^9$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_{11}$, $CO_2R_{11}$, $C(O)NR_{12}R_{13}$, $OC(O)R_{11}$, $OC(O)OR_{11}$, $OC(O)NR_{12}R_{13}$, $OCH_2CO_2R_{11}$, $C(O)R_{11}$, $NR_{12}R_{13}$, $NR_{14}C(O)R_{11}$, $NR_{14}C(O)OR_{11}$, $NR_{14}C(O)C(O)OR_{11}$, $NR_{14}C(O)C(O)NR_{12}R_{13}$, $NR_{14}C(O)C(O)$alkyl, $NR_{14}C(NCN)OR_{11}$, $NR_{14}C(O)NR_{12}R_{13}$, $NR_{14}C(NCN)NR_{12}R_{13}$, $NR_{14}C(NR_{15})NR_{12}R_{13}$, $NR_{14}SO_2NR_{12}R_{13}$, $NR_{14}SO_2R_{11}$, $SR_{11}$, $S(O)R_{11}$, $SO_2R_{11}$, $SO_3R_{11}$, $SO_2NR_{12}R_{13}$, $NHOR_{11}$, $NR_{14}NR_{12}R_{13}$, $N(COR_{11})OR_{14}$, $N(CO_2R_{11})OR_{14}$, $C(O)NR_{14}(CR_{16}R_{17})_rR_{11}$, $CO(CR_{16}R_{17})_p$ $O(CR_{12}R_{13})_qCO_2R_{11}$, $CO(CR_{16}R_{17})_rOR_{11}$, $CO(CR_{16}R_{17})_p$ $O(CR_{18}R_{19})_qR_{11}$, $CO(CR_{16}R_{17})_rNR_{12}R_{13}$, $OC(O)O$ $(CR_{16}R_{17})_mNR_{12}R_{13}$, $OC(O)N(CR_{16}R_{17})_rR_{11}$, $O(CR_{16}R_{17})_m NR_{12}R_{13}$, $NR_{14}C(O)(CR_{16}R_{17})_rR_{11}$, $NR_{14}C(O)(CR_{16}R_{17})_r OR_{11}$, $NR_{14}C(=NC)(CR_{16}R_{17})_rR_{11}$, $NR_{14}CO(CR_{16}R_{17})_r NR_{12}R_{13}$, $NR_{14}(CR_{16}R_{17})_mOR_{11}$, $NR_{14}(CR_{16}R_{17})_rCO_2R_{11}$, $NR_{14}(CR_{16}R_{17})_mNR_{12}R_{13}$, $NR_{14}(CR_{16}R_{17})_nSO_2(CR_{18}R_{19})_q R_{11}$, $CONR_{14}(CR_{16}R_{17})_nSO_2 (CR_{18}R_{19})_qR_{11}$, $SO_2NR_{14}(CR_{16}R_{17})_nCO(CR_{18}R_{19})_qR_{11}$ and $SO_2NR_{14}(CR_{16}R_{17})_m OR_{11}$.

The variables employed in the preceeding definitions are herein defined as follows:

$R_{11}$, $R_{14}$, and $R_{15}$ are independently selected from the group consisting of hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O)Oalkyl, C(O)Osubstituted alkyl, C(O)heterocyclo, C(O)heteroaryl, aryl, substituted aryl, heterocyclo and heteroaryl.

$R_{12}$ and $R_{13}$ are independently selected from the group consisting of hydrogen, alkyl, substituted alkyl, cycloalkyl, substituted cycloalkyl, alkenyl, alkynyl, C(O)alkyl, C(O)substituted alkyl, C(O)cycloalkyl, C(O)substituted cycloalkyl, C(O)aryl, C(O)substituted aryl, C(O)Oalkyl, C(O)Osubstituted alkyl, C(O)heterocyclo, C(O)heteroaryl, $S(O)_2$alkyl, $S(O)_2$substituted alkyl, $S(O)_2$cycloalkyl, $S(O)_2$substituted cycloalkyl, $S(O)_2$aryl, $S(O)_2$substituted aryl, $S(O)_2$heterocyclo, $S(O)_2$heteroaryl, aryl, substituted aryl, heterocyclo and heteroaryl, or $R_{12}$ and $R_{13}$ taken together with the nitrogen atom to which they are attached complete a heterocyclo or heteroaryl ring.

$R_{16}$ and $R_{18}$ are independently selected from hydrogen and alkyl or 1 to 4 carbons.

$R_{17}$ and $R_{19}$ are independently selected from hydrogen, alkyl of 1 to 4 carbons, and substituted alkyl or 1 to 4 carbons.

n is zero or an integer from 1 to 4.

m is an integer from 2 to 6.

p is an integer from 1 to 3.

q is zero or an integer from 1 to 3.

r is zero or an integer from 1 to 6.

The variables employed within the definition of $T^1$-$T^9$ are defined herein as follows:

$T^1$-$T^9$ are each independently (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, aryl, (aryl)alkyl, heterocyclo, (heterocyclo)alkyl, heteroaryl or (heteroaryl)alkyl, $-OT^{10}$, $-SH$, $-ST^{10}$, $-C(O)_tH$, $-C(O)_tT^{10}$, $-O-C(O)T^{10}$, $T^{17}C(O)_tN(T^{11})T^{10}$, $-SO_3H$, $-S(O)_t$ $T^{10}$, $S(O)_tN(T^{11})T^{10}$, $-T^{12}-NT^{14}T^{15}$, $-T^{12}-N(T^{11})-T^{13}-NT^{14}T^{15}$, $-T^{12}-N(T^{16})-T^{15}-T^{10}$ and $-T^{12}-N(T^{16})-T^{13}-H$; or (ii) halo, cyano, nitro, OH, oxo, —SH, amino, —OT$^{10}$, —ST$^{10}$, —C(O)$_t$H, —C(O)$_t$T$^{10}$, —O—C(O)T$^{10}$, T$^{17}$C(O)$_t$N(T$^{11}$)T$^{10}$, —SO$_3$H, —S(O)$_t$T$^{10}$, S(O)$_t$N(T$^{11}$)T$^{10}$, -T$^{12}$-NT$^{14}$T$^{15}$, -T$^{12}$-N(T$^{11}$)-T$^{13}$-NT$^{14}$T$^{15}$, -T$^{12}$-N(T$^{16}$)-T$^{15}$-T$^{10}$ or -T$^{12}$-N(T$^{16}$)-T$^{13}$-H;

The variable t is 1 or 2.

T$^{10}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl.

T$^{12}$ and T$^{13}$ are each independently a single bond, -T$^{17}$-S(O)$_t$-T$^{18}$-, -T$^{17}$-C(O)-T$^{18}$-, -T$^{17}$-C(S)-T$^{18}$-, -T$^{17}$-O-T$^{18}$-, -T$^{17}$-S-T$^{18}$-, -T$^{17}$-O—C(O)-T$^{18}$-, -T$^{17}$-C(O)$_t$T$^{18}$-, -T$^{17}$-C(=NT$^{19}$)-T$^{18}$- or -T$^{17}$-C(O)—C(O)-T$^{18}$-.

T$^{11}$, T$^{14}$, T$^{15}$, T$^{16}$ and T$^{19}$ are each independently (i) hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —ST$^{22}$, —C(O)$_t$H, —C(O)$_t$T$^{22}$, —O—C(O)T$^{22}$ and —S(O)$_t$T$^{22}$; or (ii) halo, cyano, nitro, OH, oxo, —SH, amino, —OT$^{22}$, —ST$^{22}$, —C(O)$_t$H, —C(O)$_t$T$^{22}$, —O—C(O)T$^{22}$, —SO$_3$H, —S(O)$_t$T$^{22}$ and S(O)$_t$N(T$^{11}$)T$^{22}$; or (iii) T$^{14}$ and T$^{15}$ may together be alkylene or alkenylene, completing a 3- to 8-membered saturated or unsaturated ring together with the atoms to which they are attached, which ring is substituted with one or more groups listed in the description of T$^{20}$; or (iv) T$^{14}$ or T$^{15}$ together with T$^{11}$, may be alkylene or alkenylene completing a 3- to 8-membered saturated or unsaturated ring together with the nitrogen atoms to which they are attached, which ring is substituted with one or more groups listed in the description of T$^{20}$; or (v) T$^{14}$ and T$^{15}$ or T$^{11}$ and T$^{16}$ together with the nitrogen atom to which they are attached may combine to form a group —N=CT$^{20}$T$^{21}$.

T$^{17}$ and T$^{18}$ are each independently a single bond, alkylene, alkenylene or alkynylene.

T$^{20}$ and T$^{21}$ are each (i) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —ST$^{22}$, —C(O)$_t$H, —C(O)$_t$T$^{22}$, —O—C(O)T$^{22}$ and —S(O)$_t$T$^{22}$; or (ii) halo, cyano, nitro, OH, oxo, —SH, amino, —OT$^{22}$, —ST$^{22}$, —C(O)$_t$H, —C(O)$_t$T$^{22}$, —O—C(O)T$^{22}$, —SO$_3$H, —S(O)$_t$T$^{22}$, S(O)$_t$N(T$^{11}$)T$^{22}$; or T$^{22}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl.

The term "optionally substituted" is intended to be synonymous with "unsubstituted or substituted". For example, an optionally substituted heterocycle is equivalent to an unsubstituted or substituted heterocycle.

"T-cell mediated diseases" refers to any disorder or disease state in which modulation of the activity of T-cells is implicated in a process which results in either a pathophysiological state or a process where the normal function of T-cells is intended to be suppressed for therapeutic benefit. Examples of T-cell mediated disorders include transplant rejection, graph verses host disease, and autoimmune disorders, such as rheumatoid arthritis, multiple sclerosis, juvenile diabetes, asthma, and inflammatory bowel disease, T-cell mediated hypersensitivity diseases, ischemic or reperfusion injury, and T-cell proliferative disorders. T-cell mediated diseases are included in the definition of "leukocyte activation-associated disorders" which is defined infra.

The compounds of Formula (I) in accordance with the present invention are employed, typically in the form of a pharmaceutical composition including a pharmaceutically acceptable carrier for the treatment of T-cell mediated disease. The compounds employed for this purpose are typically administered in an amount from about 0.01 to 100 mg/kg/day.

The pharmaceutical compositions comprising at least one compound of Formula (I) may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of Formula (I) may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered in the form of liposomes.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound employed in the present invention may be determined by one of ordinary skill in the art, and includes exemplary dosage amounts for an adult human of from about 0.01 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to inflammatory, immunological, or respiratory cell-associated disorders.

Compounds of Formula (I) include salts, prodrugs and solvates. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the Formula (I) may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of Formula (I), or a salt and/or solvate thereof Solvates of compounds of Formula (I) are preferably hydrates.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews,* 8, 1-38 (1992), each of which is incorporated herein by reference.

Solvates (e.g., hydrates) of the compounds of Formula (I) are also with the scope of the present invention. Methods of solvation are generally known in the art.

All stereoisomers of the present compounds, such as those which may exist due to asymmetric carbons on the R substituents of the compound of Formula (I), including enantiomeric and diastereomeric forms, are within the scope of this invention. Individual stereoisomers of the compounds of the invention may, for example, be substantially free of other isomers, or may be admixed, for example, as racemates or with all other, or other selected, stereoisomers. The chiral centers of the present invention can have an S or R configuration as defined by the IUPAC 1974 Recommendations.

Preferred Compounds

Preferred compounds within the scope of the present invention include compounds of Formula (I) (above), their enantiomers, diastereomers, and pharmaceutically acceptable salts, prodrugs and solvates thereof, in which the substituents $R^1$, $R^2$, $Z$, $J^1$, $J^2$ and $R^5$ are selected from the following:

$R^1$ is hydrogen or alkyl;

$R^2$ is
- (a) heteroaryl (preferably thiazolyl or oxazolyl) optionally independently substituted with one to three groups selected from $T^1$, $T^2$ and/or $T^3$ (preferably $T^1$, $T^2$, and/or $T^3$ are alkyl, haloalkyl, cyano, halogen, heteroaryl, —C(O)$_t$T$^{10}$, OT$^{10}$, —S(O)$_t$N(T$^{11}$)T$^{10}$ or -T$^{17}$NT$^{11}$T$^{10}$); or
- (b) aryl (preferably phenyl) substituted with one to three groups (preferably at least one group at the para position) selected from $T^1$, $T^2$ and/or $T^3$ provided that at least one of $T^1$, $T^2$ and/or $T^3$ is other than H ($T^1$ is preferably cyano, cyano, C(O)$_t$T$^{10}$, S(O)$_t$N(T$^{11}$)T$^{10}$ or heteroaryl [heteroaryl is preferably imidazolyl, oxazolyl or thiazolyl, any of which is optionally further substituted with one to two groups preferably selected from cyano, C(O)$_t$T$^{10}$, S(O)$_t$N(T$^{11}$)T$^{10}$ and haloalkyl]); or
- (c) aryl fused to a heteroaryl or heterocyclo ring forming a fused ring system bound to N* through the aryl wherein the fused ring system (preferably tetrahydro indole bound through the aryl ring, quinolyl bound through the aryl ring [especially quinol-6-yl], quinazolinyl bound through the aryl ring [especially quinazolin-7-yl], cinnolinyl bound through the aryl ring [especially cinnolin-6-yl], isoquinolinyl bound through the aryl ring [especially isoquinol-6-yl], or phthalazinyl bound through the aryl ring [especially phthalazin-6-yl]). may be optionally independently substituted with one to three groups selected from $T^1$, $T^2$ and/or $T^3$ ($T^1$, $T^2$, and/or $T^3$ are preferably selected from halogen, OH, OT$^{10}$, alkyl, haloalkyl —CO$_t$H, —CO$_t$T$^{10}$ and —C(O)NT$^{11}$T$^{10}$);

Z is —NR$^3$R$^4$, —NR$^3$SO$_2$R$^6$, OR$^4$, SR$^4$, haloalkyl or halogen (preferably —NR$^3$R$^4$ or halogen, even more preferably —NR$^3$R$^4$);

$J^1$ is O, S, S(O), S(O)$_2$ or optionally substituted $C_{1-3}$ alkylene (preferably O, S or optionally substituted $C_1$ alkylene);

$J^2$ is carbonyl or optionally substituted $C_{1-3}$ alkylene, provided that $J^1$ and $J^2$ taken together do not form an alkylene chain of greater than 4 carbon atoms;

$R^3$ and $R^4$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which may be optionally independently substituted where valance allows with one to three groups $T^4$, $T^5$ and/or $T^6$ ($T^4$, $T^5$ and/or $T^6$ are preferably selected from alkyl, hydroxyalkyl, halo, cyano, OH, oxo, cycloalkyl, cycloalkenyl, heterocyclo, heteroaryl, —C(O)$_t$T$^{10}$, —C(O)$_t$H, —NHC(O)T$^{10}$, C(O)N(T$^{11}$)(T$^{10}$), OT$^{10}$, ST$^{10}$, S(O)$_3$H, S(O)$_t$T$^{10}$, S(O)$_t$N(T$^{10}$)(T$^{11}$), T$^{17}$N(T$^{14}$)(T$^{15}$) and T$^{12}$N(T$^{16}$)-T$^{15}$-T$^{10}$);

or $R^3$ and $R^4$ may be taken together with the nitrogen atom to which they are attached to form a heterocyclo or heteroaryl ring (preferably piperidyl, piperazinyl, morpholinyl, diazapanyl, 4 dioxa-8-azaspiro[4,5]decan-8-yl or pyrrolyl), either of which is optionally independently substituted where valance allows with one to three groups independently selected from $T^4$, $T^5$ and/or $T^6$ [preferably $T^4$, $T^5$ and/or $T^6$ is selected from alkyl, hydroxyalkyl, halo, cyano, OH, oxo, cycloalkyl, cycloalkenyl, optionally substituted heterocyclo, optionally substituted heteroaryl, —C(O)$_t$T$^{10}$, —C(O)$_t$H, —NHC(O)T$^{10}$, C(O)N(T$^{11}$)(T$^{10}$), OT$^{10}$, ST$^{10}$, S(O)$_3$H, S(O)$_t$T$^{10}$, S(O)$_t$N(T$^{14}$)(T$^{15}$), T$^{12}$N(T$^{14}$)(T$^{15}$) and T$^{12}$N(T$^{16}$)-T$^{15}$-T$^{10}$];

$R^5$ is
- (i) H, cyano, alkyl, alkenyl, alkynyl, cycloalkyl, (cycloalkyl)alkyl, aryl, (aryl)alkyl, heterocyclo, (heterocyclo [preferably piperizolyl, morpholinyl, and indanyl],) alkyl, heteroaryl or (heteroaryl [preferably pyridyl, furanyl, thienyl, benzoisothiazolyl, and thiazolyl])alkyl, any of which may be independently substituted where valance allows with one to three groups $T^7$, $T^8$ and/or $T^9$ [$T^7$, $T^8$ and/or $T^9$ preferably selected from cyano, oxo, hydroxy, alkyl, halo, haloalkyl, —OT$^{10}$, —C(O)$_t$N(T$^{11}$)(T$^{10}$), —C(O)$_t$NH S(O)$_t$(T$^{11}$), —S(O)$_t$T$^{10}$, —S(O)$_t$N(T$^{14}$)(T$^{15}$), T$^{12}$N(T$^{14}$)(T$^{15}$), —C(O)$_t$T$^{11}$, heterocyclo and heteroaryl, any of which may be optionally substituted by one to three groups independently preferably selected from cyano, oxo, hydroxy, alkyl, halo, haloalkyl, and —OT$^{10}$]; or
- (ii) —C(O)$_t$R$^7$, —C(O)—C(O)—C(O)OR$^7$ or —SO$_2$R$^8$;

Preferred compounds of the present invention include compounds of Formula (Ia)

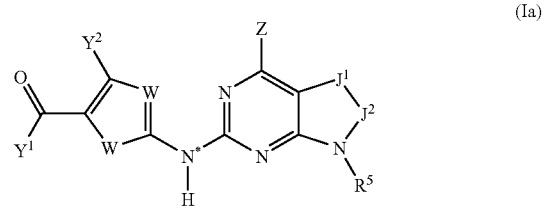

(Ia)

their enantiomers, diastereomers, and pharmaceutically acceptable salts, prodrugs and solvates thereof, in which:

W is O or S;

$Y^1$ is —NHT$^{15}$ or OT$^{10}$;

$Y^2$ is alkyl, or haloalkyl;

Z is —NR$^3$R$^4$ or halogen;

$J^1$ is O or optionally substituted $C_{1-3}$ alkylene;

$J^2$ is carbonyl or optionally substituted $C_{1-3}$ alkylene, provided that $J^1$ and $J^2$ taken together do not form an alkylene chain of greater than 4 carbon atoms;

$R^3$ and $R^4$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which may be optionally independently substituted where valance allows with one to three groups $T^4$, $T^5$ and/or $T^6$;

or $R^3$ and $R^4$ may be taken together with the nitrogen atom to which they are attached to form a heterocyclo or heteroaryl ring, either of which is optionally independently substituted where valance allows with one to three groups independently selected from $T^4$, $T^5$ and/or $T^6$;

$R^5$ is
- (i) H, cyano, alkyl, alkenyl, alkynyl, cycloalkyl, (cycloalkyl)alkyl, aryl, (aryl)alkyl, heterocyclo, (heterocyclo)alkyl, heteroaryl or (heteroaryl)alkyl, any of which may be independently substituted where valance allows with one to three groups $T^7$, $T^8$ and/or $T^9$; or
- (ii) —C(O)$_t$R$^7$, —C(O)—C(O)—C(O)OR$^7$ or —SO$_2$R$^8$;

$R^6$ is alkyl, alkenyl, aryl, (aryl)alkyl, heteroaryl, (heteroaryl)alkyl, cycloalkyl, (cycloalkyl)alkyl, heterocyclo, or (heterocyclo)alkyl, any of which may be optionally independently substituted where valance allows with one to three groups $T^4$, $T^5$ and/or $T^6$;

R⁷ is
(i) H, alkyl, alkenyl, heterocyclo, (heterocyclo)alkyl, (hydroxy)alkyl, (alkoxy)alkyl, (aryloxy)alkyl, heteroaryl, aryl or (aryl)alkyl, any of which may be optionally independently substituted where valance allows with one to three groups $T^7$, $T^8$ and/or $T^9$; or
(ii) —NR⁹R¹⁰ or (NR⁹R¹⁰)alkyl;

R⁸ is
(i) alkyl, alkenyl, heterocyclo, (heterocyclo)alkyl, (hydroxy)alkyl, (alkoxy)alkyl, (aryloxy)alkyl, heteroaryl, aryl or (aryl)alkyl, any of which may be optionally independently substituted where valance allows with one to three groups $T^7$, $T^8$ and/or $T^9$; or
(ii) —NR⁹R¹⁰ or (NR⁹R¹⁰)alkyl;

R⁹ and R¹⁰ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which may be optionally independently substituted where valance allows with one to three groups $T^7$, $T^8$ and/or $T^9$;

$T^1$-$T^9$ are each independently
(i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, aryl, (aryl)alkyl, heterocyclo, (heterocyclo)alkyl, heteroaryl or (heteroaryl)alkyl, —OT¹⁰, —SH, —ST¹⁰, —C(O)$_t$H, —C(O)$_t$T¹⁰, —O—C(O)T¹⁰, T¹⁷C(O)$_t$N(T¹¹)T¹⁰, —SO₃H, —S(O)$_t$T¹⁰, S(O)$_t$N(T¹¹)T¹⁰, -T¹²-NT¹⁴T¹⁵, -T¹²-N(T¹¹)-T¹³-NT¹⁴T¹⁵, -T¹²-N(T¹⁶)-T¹⁵-T¹⁰ and -T¹²-N(T¹⁶)-T¹³-H; or
(ii) halo, cyano, nitro, OH, oxo, —SH, amino, —OT¹⁰, —ST¹⁰, —C(O)$_t$H, —C(O)$_t$T¹⁰, —O—C(O)T¹⁰, T¹⁷C(O)$_t$N(T¹¹)T¹⁰, —SO₃H, —S(O)$_t$T¹⁰, S(O)$_t$N(T¹¹)T¹⁰, -T¹²-NT¹⁴T¹⁵, -T¹²-N(T¹¹)-T¹³-NT¹⁴T¹⁵, -T¹²-N(T¹⁶)-T¹⁵-T¹⁰ or -T¹²-N(T¹⁶)-T¹³-H;

t is 1 or 2;

$T^{10}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{12}$ and $T^{13}$ are each independently a single bond, -T¹⁷-S(O)$_t$-T¹⁸-, -T¹⁷-C(O)-T¹⁸-, -T¹⁷-C(S)-T¹⁸-, -T¹⁷-O-T¹⁸-, -T¹⁷-S-T¹⁸-, -T¹⁷-O—C(O)-T¹⁸-, -T¹⁷-C(O)$_t$T¹⁸-, -T¹⁷-C(=NT¹⁹)-T¹⁸- or -T¹⁷-C(O)—C(O)-T¹⁸-;

$T^{11}$, $T^{14}$, $T^{15}$, $T^{16}$ and $T^{19}$ are each independently
(i) hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —ST²², —C(O)$_t$H, —C(O)$_t$T²², —O—C(O)T²² and —S(O)$_t$T²²; or
(ii) halo, cyano, nitro, OH, oxo, —SH, amino, —OT²², —ST²², —C(O)$_t$H, —C(O)$_t$T²², —O—C(O)T²², —SO₃H, —S(O)$_t$T²² or S(O)$_t$N(T¹¹)T²²;
(iii) T¹⁴ and T¹⁵ may together be alkylene or alkenylene, completing a 3- to 8-membered saturated or unsaturated ring together with the atoms to which they are attached, which ring is substituted with one or more groups listed in the description of $T^{20}$; or
(iv) T¹⁴ or T¹⁵ together with T¹¹, may be alkylene or alkenylene completing a 3- to 8-membered saturated or unsaturated ring together with the nitrogen atoms to which they are attached, which ring is substituted with one or more groups listed in the description of $T^{20}$; or
(v) T¹⁴ and T¹⁵ or T¹¹ and T¹⁶ together with the nitrogen atom to which they are attached may combine to form a group —N=CT²⁰T²¹;

$T^{17}$ and $T^{18}$ are each independently a single bond, alkylene, alkenylene or alkynylene;

$T^{20}$ and $T^{21}$ are each
(i) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —ST²², —C(O)$_t$H, —C(O)$_t$T²², —O—C(O)T²² and —S(O)$_t$T²²; or
(ii) halo, cyano, nitro, OH, oxo, —SH, amino, —OT²², —ST²², —C(O)$_t$H, —C(O)$_t$T²², —O—C(O)T²², —SO₃H, —S(O)$_t$T²² or S(O)$_t$N(T¹¹)T²²; and $T^{22}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl.

More preferred compounds are compounds within the scope Formula (Ia), their enantiomers, diastereomers, and pharmaceutically acceptable salts, prodrugs and solvates thereof, in which Z is selected from

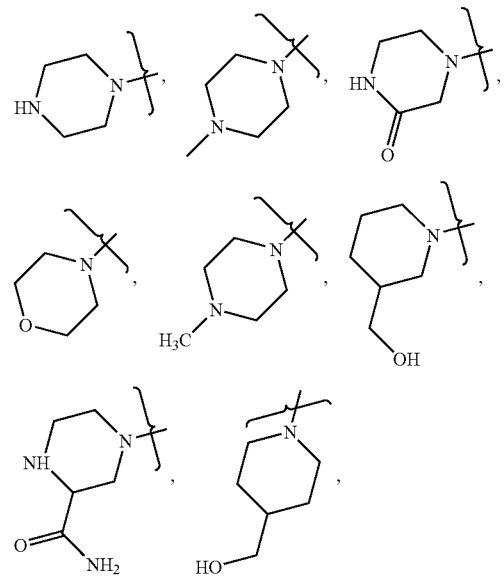

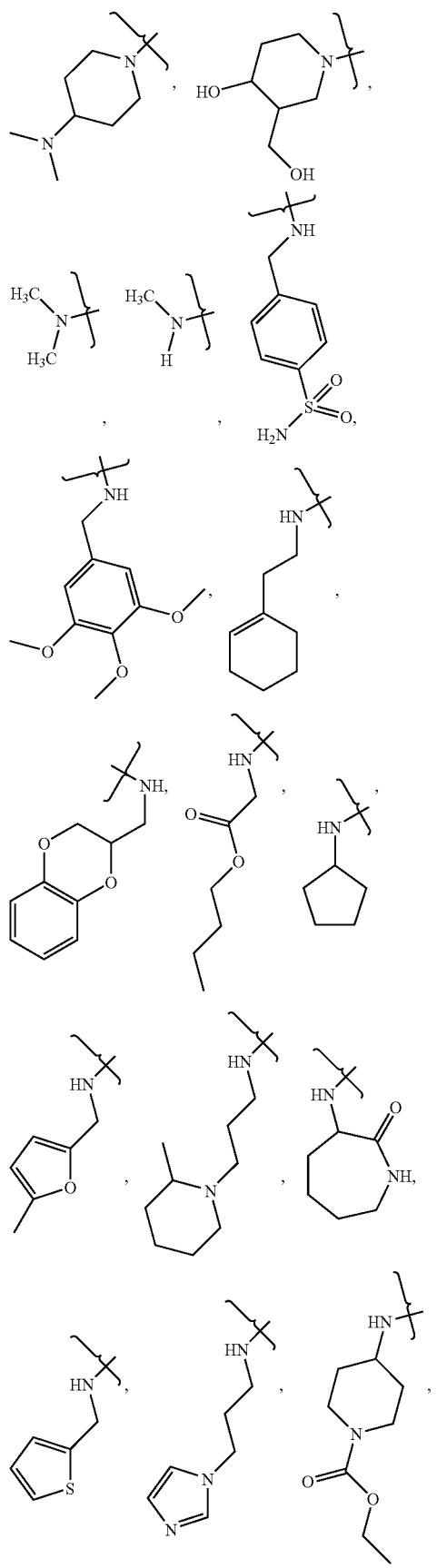
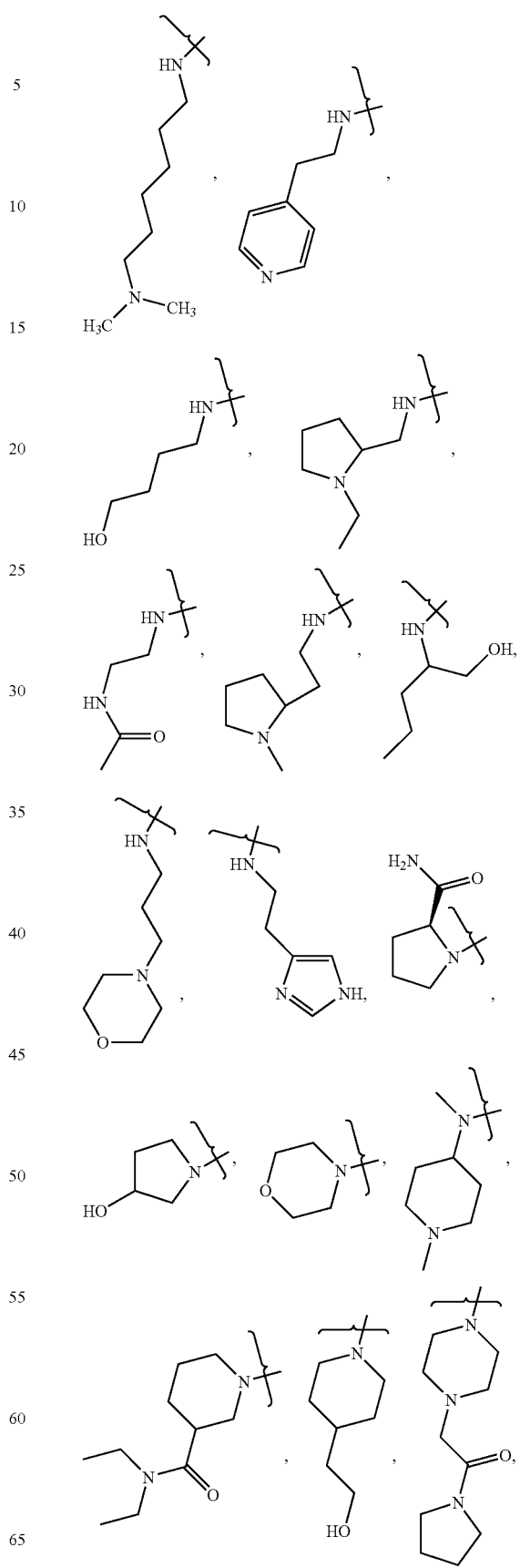

-continued
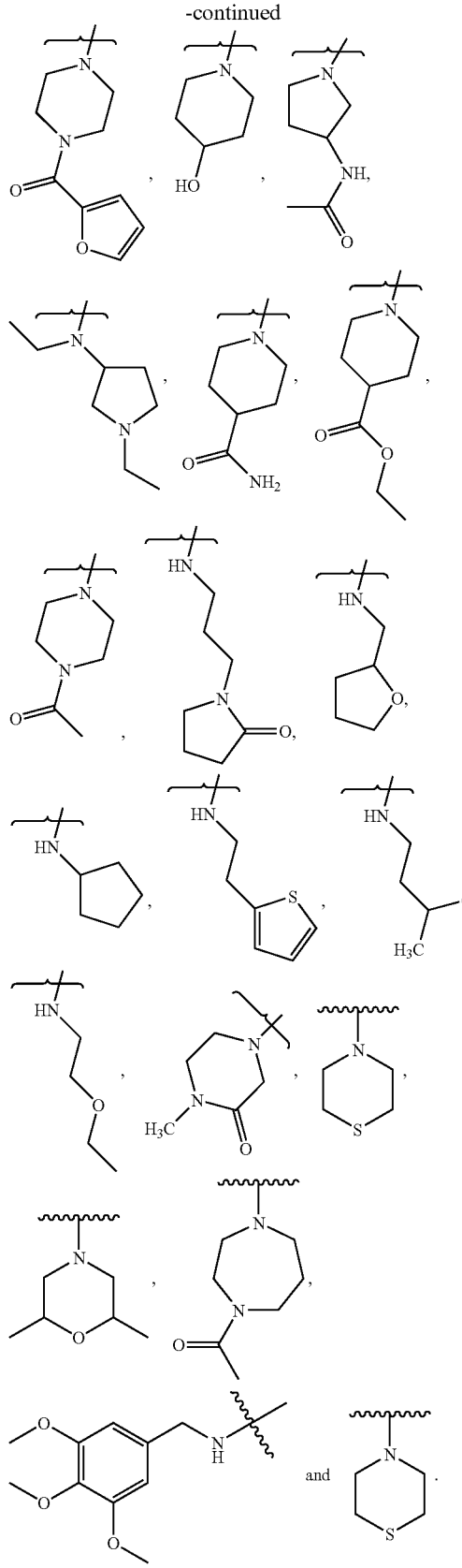
Also more preferred compounds include compounds within the scope of Formula (Ia), their enantiomers, diastereomers, and pharmaceutically acceptable salts, prodrugs and solvates thereof, in which $R^5$ is selected from:
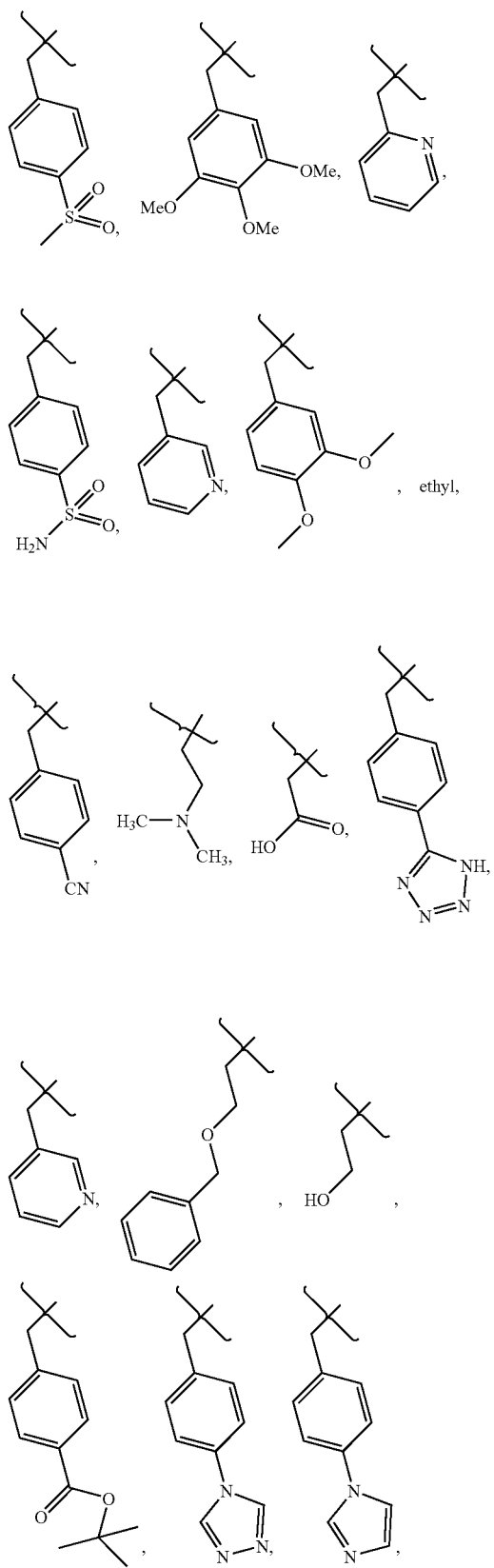

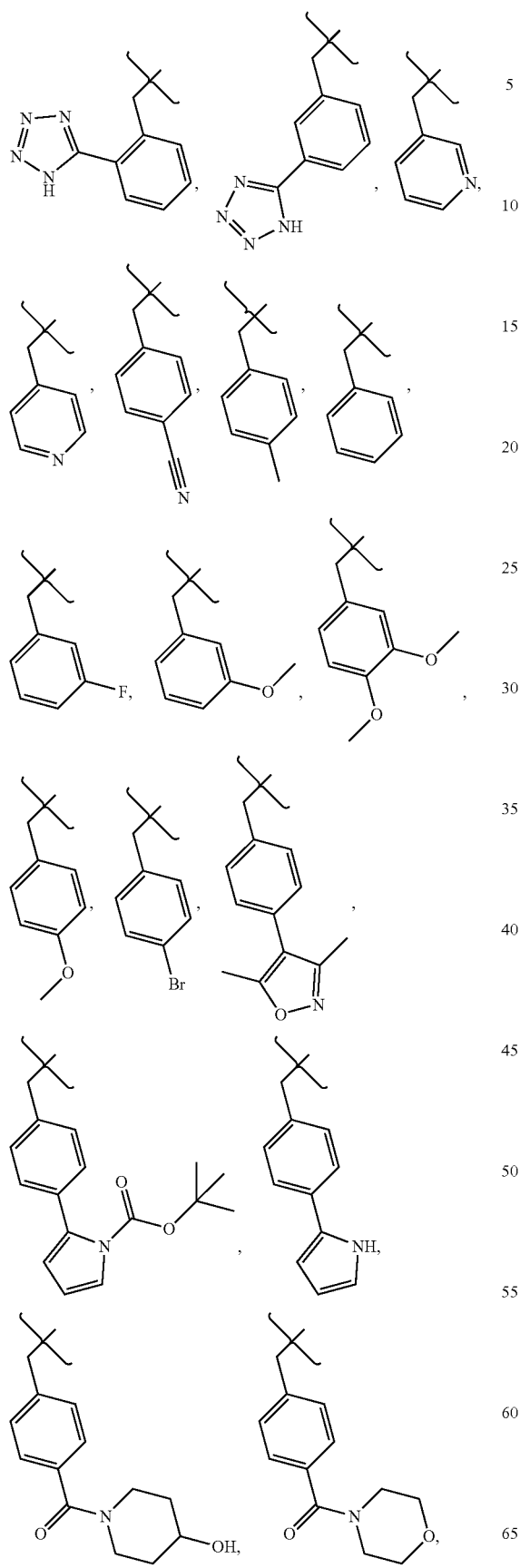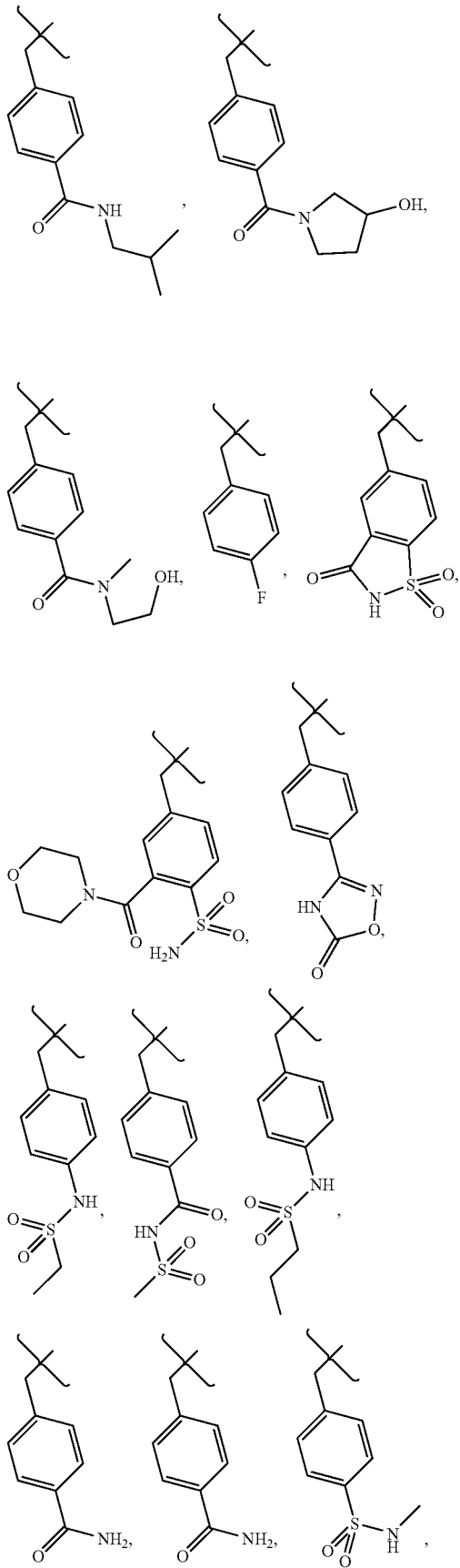

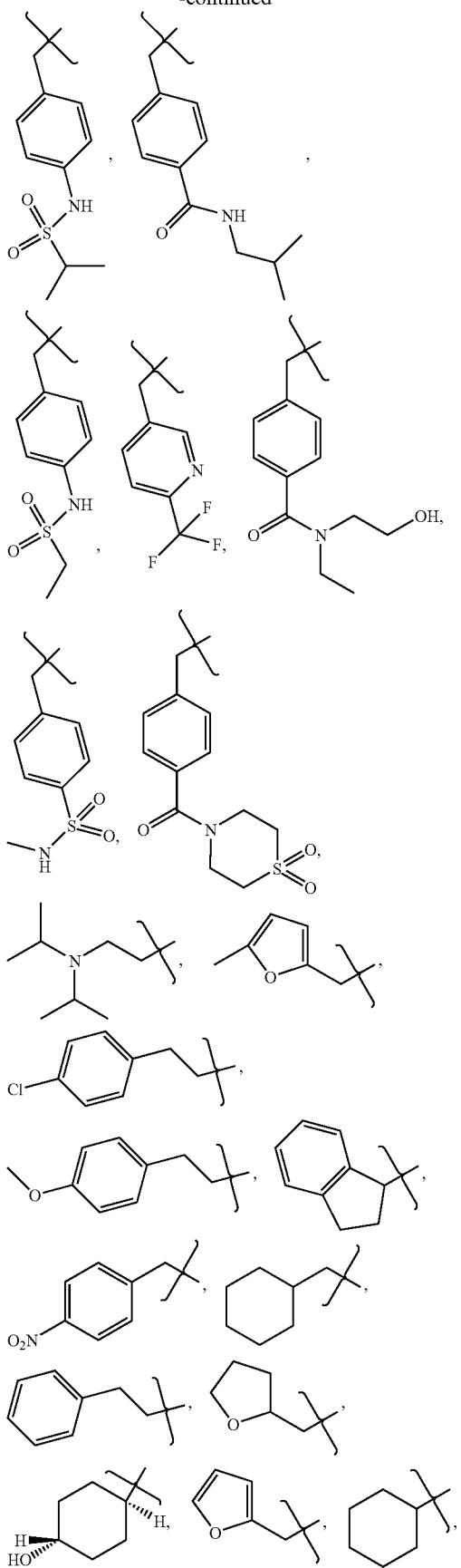

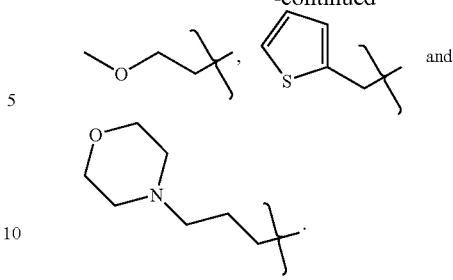

Preferred compounds within the scope of the present invention include compounds having Formula (II)

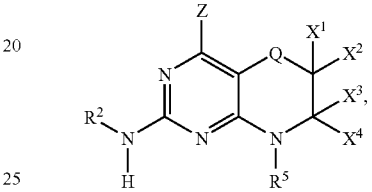

(II)

their enantiomers, diastereomers, and pharmaceutically acceptable salts, prodrugs and solvates thereof, in which:

Q is O, S or optionally substituted $C_1$ alkylene (more preferably Q is —$CH_2$— or O); and $X^1$, $X^2$, $X^3$ and $X^4$ are (i) independently chosen from hydrogen, $T^{10}$, $OT^{10}$ and $NT^{14}T^{15}$; and/or (ii) either $X^1$ and $X^2$ or $X^3$ and $X^4$ may be taken together to be a carbonyl group.

Preferred compounds within the scope of the present invention include compounds having Formula (III)

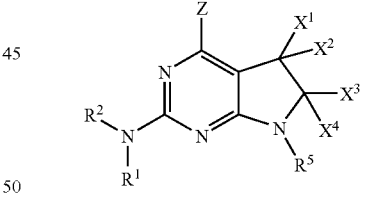

(III)

their enantiomers, diastereomers, and pharmaceutically acceptable salts, prodrugs and solvates thereof, in which:

$X^1$, $X^2$, $X^3$ and $X^4$ are (i) independently chosen from hydrogen, $T^{10}$, $OT^{10}$ or $NT^{14}T^{15}$; and/or (ii) either $X^1$ and $X^2$ or $X^3$ and $X^4$ may be taken together to be a carbonyl group.

More preferred compounds are compounds within the scope of Formula (III) (above), their enantiomers, diastereomers, and pharmaceutically acceptable salts, prodrugs and solvates thereof, in which $X^1$, $X^2$, $X^3$ and $X^4$ are independently chosen from hydrogen, $T^{10}$, $OT^{10}$ or $NT^{14}T^{15}$.

More preferred compounds also include compounds within the scope of Formula (III), their enantiomers, diastereomers, and pharmaceutically acceptable salts, prodrugs and solvates thereof, in which:

$X^1$, $X^2$ are independently chosen from hydrogen, $T^{10}$, $OT^{10}$ or $NT^{14}T^{15}$; and $X^3$ and $X^4$ are taken together to be a carbonyl group.

Preferred compounds within the scope of the present invention include compounds having Formula (IV)

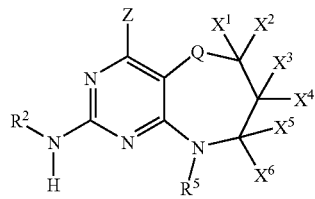
(IV)

their enantiomers, diastereomers, and pharmaceutically acceptable salts, prodrugs and solvates thereof, wherein:

Q is O, S or optionally substituted $C_1$ alkylene (more preferably Q is —$CH_2$— or O), and $X^1$, $X^2$, $X^3$, $X^4$, $X^5$ and $X^6$ are (i) independently chosen from hydrogen, $T^{10}$, $OT^{10}$ or $NT^{14}T^{15}$; and/or (ii) any one of $X^1$ and $X^2$ or $X^3$ and $X^4$ or $X^5$ and $X^6$ may be taken together to be a carbonyl group.

More preferred compounds of the present invention include compounds of Formulas (I), (II), (III), or (IV), their enantiomers, diastereomers, and pharmaceutically acceptable salts, prodrugs and solvates thereof, in which $R^2$ is chosen from:

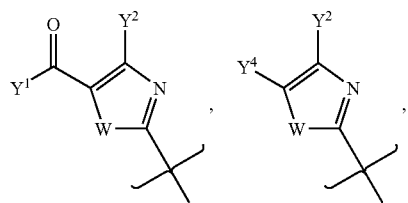

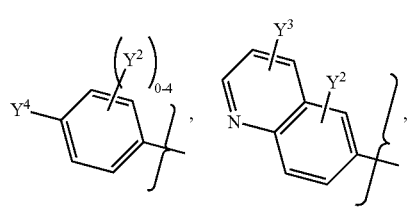

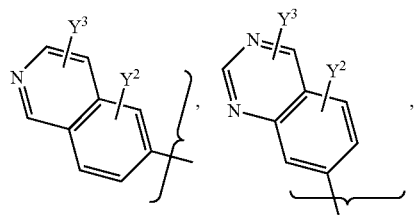

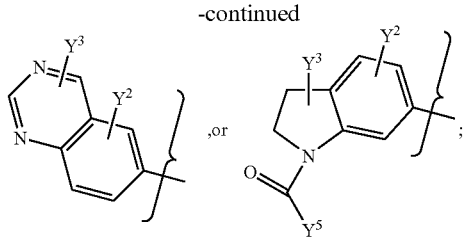

W is O or S;

$Y^1$ is —$NHT^{15}$ or $OT^{10}$;

$Y^2$ and $Y^3$ are independently hydrogen, halo, $OT^{10}$, alkyl or haloalkyl;

$Y^4$ is optionally substituted heteroaryl, cyano, $C(O)_tT^{10}$ or $S(O)_tNT^{14}T^{15}$; and $Y^5$ is alkyl, haloalkyl, $NHT^{15}$ or $OT^{10}$.

Even more preferred compounds of the present invention include compounds of Formulas (I), (Ia), (II), (III), or (IV), their enantiomers, diastereomers, and pharmaceutically acceptable salts, prodrugs and solvates thereof, wherein $R^2$ is

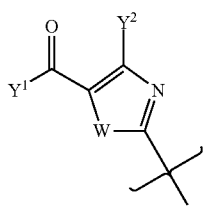

W is O or S (preferably S);

$Y^1$ is —$NHT^{15}$ or $OT^{10}$ (preferably $OT^{10}$) and $Y^2$ is alkyl, or haloalkyl (preferably alkyl).

More preferred compounds of the present invention include compounds of Formulas (I), (Ia) (II), (III), or (IV), their enantiomers, diastereomers, and pharmaceutically acceptable salts, prodrugs and solvates thereof, wherein $R^1$ is H;

$J^1$ is O, S or optionally substituted $C_1$ alkylene;

$J^2$ is C(O), or optionally substituted $C_{1-3}$ alkylene;

Z is —$NR^3R^4$ or halo;

$R^3$ is H or alkyl;

Even more preferred compounds of the present invention include compounds of Formula (I), (Ia), (II), (III), or (IV) include:

i. 2-[7-(4-Methanesulfonyl-benzyl)-4-morpholin-4-yl-5,6-dihydro-pyrrolo[2,3-d]pyrimidin2-ylamino]-4-methyl-thiazole-5-carboxylic acid ethyl ester;

2-[7-(4-Methanesulfonyl-benzyl)-4-methylamino-5,6-dihydro-pyrrolo[2,3-d]pyrimidin-2-ylamino]-4-methyl-thiazole-5-carboxylic acid ethyl ester;

2-[7-(3,4-Dimethoxy-benzyl)-4-(3-oxo-piperazin-1-yl)-5,6-dihydro-pyrrolo[2,3-d]pyrimidin-2-ylamino]-4-methyl-thiazole-5-carboxylic acid ethyl ester;

2-[4-(2-Cyclohex-1-enyl-ethylamino)-7-pyridin-3-ylmethyl-5,6-dihydro-pyrrolo[2,3-d]pyrimidin-2-ylamino]-4-methyl-thiazole-5-carboxylic acid ethyl ester;

2-[4-(Butoxycarbonylmethyl-amino)-7-pyridin-3-ylmethyl-5,6-dihydro-pyrrolo[2,3-d]pyrimidin-2-ylamino]-4-methyl-thiazole-5-carboxylic acid ethyl ester;

2-(4-Cyclopentylamino-7-pyridin-3-ylmethyl-5,6-dihydro-pyrrolo[2,3-d]pyrimidin-2-ylamino)-4-methyl-thiazole-5-carboxylic acid ethyl ester;

4-Methyl-2-{4-[(5-methyl-furan-2-ylmethyl)-amino]-7-pyridin-3-ylmethyl-5,6-dihydro-pyrrolo[2,3-d]pyrimidin-2-ylamino}-thiazole-5-carboxylic acid ethyl ester;

4-Methyl-2-{4-[3-(2-methyl-piperidin-1-yl)-propylamino]-7-pyridin-3-ylmethyl-5,6-dihydro-pyrrolo[2,3-d]pyrimidin-2-ylamino}-thiazole-5-carboxylic acid ethyl ester;

4-Methyl-2-[4-(2-oxo-azepan-3-ylamino)-7-pyridin-3-ylmethyl-5,6-dihydro-pyrrolo[2,3-d]pyrimidin-2-ylamino]-thiazole-5-carboxylic acid ethyl ester;

4-Methyl-2-{7-pyridin-3-ylmethyl-4-[(thiophen-2-ylmethyl)-amino]-5,6-dihydro-pyrrolo[2,3-d]pyrimidin-2-ylamino}-thiazole-5-carboxylic acid ethyl ester;

2-[4-(3-Imidazol-1-yl-propylamino)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-[4-(1-carboxyethyl-piperidin-4-ylamino)-7-pyridin-3-ylmethyl-5,6-dihydro-pyrrolo[2,3-d]pyrimidin-2-ylamino]-thiazole-5-carboxylic acid ethyl ester;

2-[4-(6-Dimethylamino-hexylamino)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-[4-(2-pyridin-4-yl-ethylamino)-7-pyridin-3-ylmethyl-5,6-dihydro-pyrrolo[2,3-d]pyrimidin-2-ylamino]-thiazole-5-carboxylic acid ethyl ester;

2-[4-(4-Hydroxy-butylamino)-7-pyridin-3-ylmethyl-5,6-dihydro-pyrrolo[2,3-d]pyrimidin-2-ylamino]-4-methyl-thiazole-5-carboxylic acid ethyl ester;

2-{4-[(1-Ethyl-pyrrolidin-2-ylmethyl)-amino]-7-pyridin-3-ylmethyl-5,6-dihydro-pyrrolo[2,3-d]pyrimidin-2-ylamino}-4-methyl-thiazole-5-carboxylic acid ethyl ester;

2-[4-(2-Acetylamino-ethylamino)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-{4-[2-(1-methyl-pyrrolidin-2-yl)-ethylamino]-7-pyridin-3-ylmethyl-5,6-dihydro-pyrrolo[2,3-d]pyrimidin-2-ylamino}-thiazole-5-carboxylic acid ethyl ester;

2-[4-(1-Hydroxymethyl-butylamino)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-[4-(3-morpholin-4-yl-propylamino)-7-pyridin-3-ylmethyl-5,6-dihydro-pyrrolo[2,3-d]pyrimidin-2-ylamino]-thiazole-5-carboxylic acid ethyl ester;

2-{4-[2-(1H-Imidazol-4-yl)-ethylamino]-7-pyridin-3-ylmethyl-5,6-dihydro-pyrrolo[2,3-d]pyrimidin-2-ylamino}-4-methyl-thiazole-5-carboxylic acid ethyl ester;

2-[4-{(S)-2-Carbamoyl-pyrrolidin-1-yl}-7-pyridin-3-ylmethyl-5,6-dihydro-pyrrolo[2,3-d]pyrimidin-2-ylamino]-4-methyl-thiazole-5-carboxylic acid ethyl ester;

2-[4-(3-Hydroxy-pyrrolidin-1-yl)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-(4-morpholin-4-yl-7-pyridin-3-ylmethyl-5,6-dihydro-pyrrolo[2,3-d]pyrimidin-2-ylamino)-thiazole-5-carboxylic acid ethyl ester;

4-Methyl-2-{4-[methyl-(1-methyl-piperidin-4-yl)-amino]-7-pyridin-3-ylmethyl-5,6-dihydro-pyrrolo[2,3-d]pyrimidin-2-ylamino}-thiazole-5-carboxylic acid ethyl ester;

2-[4-(3-Diethylcarbamoyl-piperidin-1-yl)-7-pyridin-3-ylmethyl-5,6-dihydro-pyrrolo[2,3-d]pyrimidin-2-ylamino]-4-methyl-thiazole-5-carboxylic acid ethyl ester;

2-{4-[4-(2-Hydroxy-ethyl)-piperidin-1-yl]-7-pyridin-3-ylmethyl-5,6-dihydro-pyrrolo[2,3-d]pyrimidin-2-ylamino}-4-methyl-thiazole-5-carboxylic acid ethyl ester;

4-Methyl-2-{4-[4-(2-oxo-2-pyrrolidin-1-yl-ethyl)-piperazin-1-yl]-7-pyridin-ylmethyl-5,6-dihydro-pyrrolo[2,3-d]pyrimidin-2-ylamino}-thiazole-5-carboxylic acid ethyl ester;

2-{4-[4-(Furan-2-carbonyl)-piperazin-1-yl]-7-pyridin-3-ylmethyl-5,6-dihydro-pyrrolo[2,3-d]pyrimidin-2-ylamino}-4-methyl-thiazole-5-carboxylic acid ethyl ester, 2-[4-(4-Hydroxy-piperidin-1-yl)-7-pyridin-3-ylmethyl-5,6-dihydro-pyrrolo[2,3-d]pyrimidin-2-ylamino]-4-methyl-thiazole-5-carboxylic acid ethyl ester;

2-[4-(3-Acetylamino-pyrrolidin-1-yl)-7-pyridin-3-ylmethyl-5,6-dihydro-pyrrolo[2,3-d]pyrimidin-2-ylamino]-4-methyl-thiazole-5-carboxylic acid ethyl ester;

2-{4-[Ethyl-(1-ethyl-pyrrolidin-3-yl)-amino]-7-pyridin-3-ylmethyl-5,6-dihydro-pyrrolo[2,3-d]pyrimidin-2-ylamino}-4-methyl-thiazole-5-carboxylic acid ethyl ester;

4-Methyl-2-[4-(4-carboxyethyl-piperidin-1-yl)-7-pyridin-3-ylmethyl-5,6-dihydro-pyrrolo[2,3-d]pyrimidin-2-ylamino]-thiazole-5-carboxylic acid ethyl ester;

2-[4-(4-Acetyl-piperazin-1-yl)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-{4-[3-(2-oxo-pyrrolidin-1-yl)-propylamino]-7-[4-(1H-tetrazol-5-yl)-benzyl]-5,6-dihydro-pyrrolo[2,3-d]pyrimidin-2-ylamino}-thiazole-5-carboxylic acid ethyl ester;

4-Methyl-2-(4-morpholin-4-yl-6-oxo-7-pyridin-4-ylmethyl-5,6-dihydro-pyrrolo[2,3-d]pyrimidin-2-ylamino)-thiazole-5-carboxylic acid ethyl ester;

4-Methyl-2-[4-morpholin-4-yl-8-(4-sulfamoyl-benzyl)-5,6,7,8-tetrahydro-pyrido[2,3-d]pyrimidin-2-ylamino]-thiazole-5-carboxylic acid ethyl ester;

4-Methyl-2-[4-methylamino-8-(4-sulfamoyl-benzyl)-5,6,7,8-tetrahydro-pyrido[2,3-d]pyrimidin-2-ylamino]-thiazole-5-carboxylic acid ethyl ester;

2-[8-(4-Ethanesulfonylamino-benzyl)-4-(3-oxo-piperazin-1-yl)-5,6,7,8-tetrahydro-pyrido[2,3-d]pyrimidin-2-ylamino]-4-methyl-thiazole-5-carboxylic acid ethyl ester;

2-[4-(2-Acetylamino-ethylamino)-8-(4-ethanesulfonylamino-benzyl)-5,6,7,8-tetrahydro-pyrido[2,3-d]pyrimidin-2-ylamino]-4-methyl-thiazole-5-carboxylic acid ethyl ester;

2-[8-(4-Methanesulfonylaminocarbonyl-benzyl)-4-(3-oxo-piperazin-1-yl)-5,6,7,8-tetrahydro-pyrido[2,3-d]pyrimidin-2-ylamino]-4-methyl-thiazole-5-carboxylic acid ethyl ester;

2-[4-(4-Hydroxy-piperidin-1-yl)-9-(4-sulfamoyl-benzyl)-5,6,7,8-tetrahydro-pyrimido[4,5-b]azepin-2-ylamino]-4-methyl-thiazole-5-carboxylic acid ethyl ester; or 2-[4-(4-Acetyl-[1,4]diazepan-1-yl)-9-(4-sulfamoyl-benzyl)-5,6,7,8-tetrahydro-pyrimido[4,5-b]azepin-2-ylamino]-4-methyl-thiazole-5-carboxylic acid ethyl ester; or ii. the enantiomers, diastereomers, and pharmaceutically acceptable salts, prodrugs and solvates of each of (i).

Methods of Preparation

Compounds having the structure of Formula (I) may be prepared by reference to the methods illustrated in the following Schemes A through D. In particular, Schemes A1, A2, A3 and A4 depict various methods by which compounds of Formula (I) may be prepared. Scheme B illustrates the preparation of key intermediate 2-substituted malonates. Scheme C depicts a method by which amides of Formula (I) may be prepared from esters of Formula (I). Finally, schemes D1 and D2 outline the preparation of the intermediate guanidines.

One of skill in the art understands that any compound of Formula (I) may be produced by the above Schemes by the suitable selection of appropriate substitution. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

Compounds within the scope of the present invention may be prepared by several methods. Compounds of formula II, III, or IV where Q is not a heteroatom is prepared as shown in Scheme A1. Guanidine A1.1 is heated in the presence of a base such as sodium ethoxide with an appropriate 2-substituted malonate A1.2 to produce intermediate A1.3 which upon reaction with phosphorous oxychloride at elevated temperature provides intermediate A1.4. Cleavage of the olefin by a two step protocol involving dihydroxylation with osmium tetraoxide in the presence of a co-oxidant such as N-methylmorpholine N-oxide to give intermediate A1.5 followed by reaction with either sodium periodate or lead(IV) acetate to provide intermediate A1.6. Reductive amination of A1.6 using sodium triacetoxyborohydride and acetic acid in THF with amine A1.7 results in spontaneous ring closure giving intermediate A1.8. Reaction with reagent A1.9, (an alcohol, a thiol or a sulfonamide) in the presence of a suitable base provides A1.10 which is a compound described by Formula II, III, or IV.

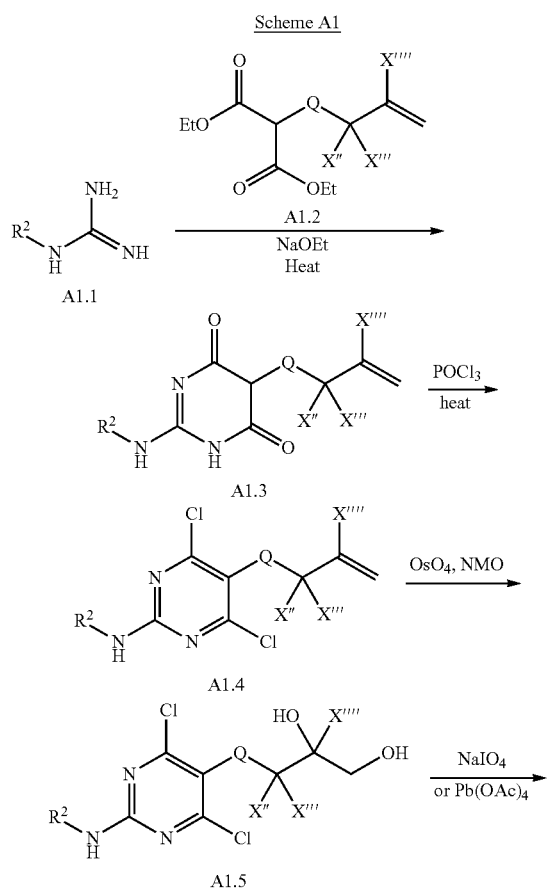

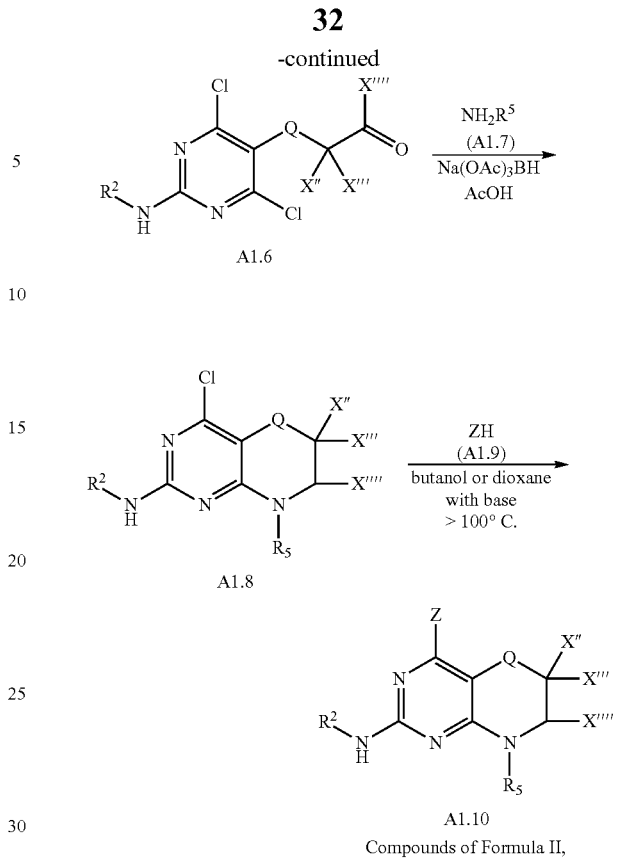

$Q = (CTT')_n$ n = 0, 1, or 2
X, X', X", T T', etc. = a substituent
$Z = NR^3R^4, NR^3SO_2R^4, OR^4, SR^4$ In the case of compounds of Formula II, III, or IV where Q is a heteroatom (Scheme A2), guanidine A1.1 is heated in the presence of a base such as sodium ethoxide with an appropriate 2-substituted malonate A2.1 to produce intermediate A2.2. Reaction of A2.2 with phosphorous oxychloride in the presence of a base at elevated temperature provides intermediate A2.3. Heating with amine A1.7 in the presence of a base such as triethylamine or Hunigs base in a solvent such as N-methyl pyrrolidone followed by hydrolysis with aqueous acid provides intermediate A2.4. A2.4 is then reduced with sodium cyanoborohydride in acetic acid to A2.5. Reaction with reagent A1.9, (an amine, alcohol, thiol or sulfonamide) in the presence of a suitable base provides compound A2.6 which is a compound of Formula II, III, or IV.

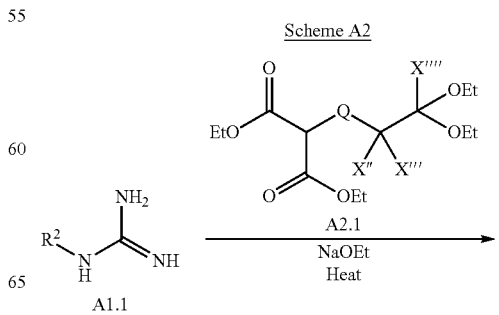

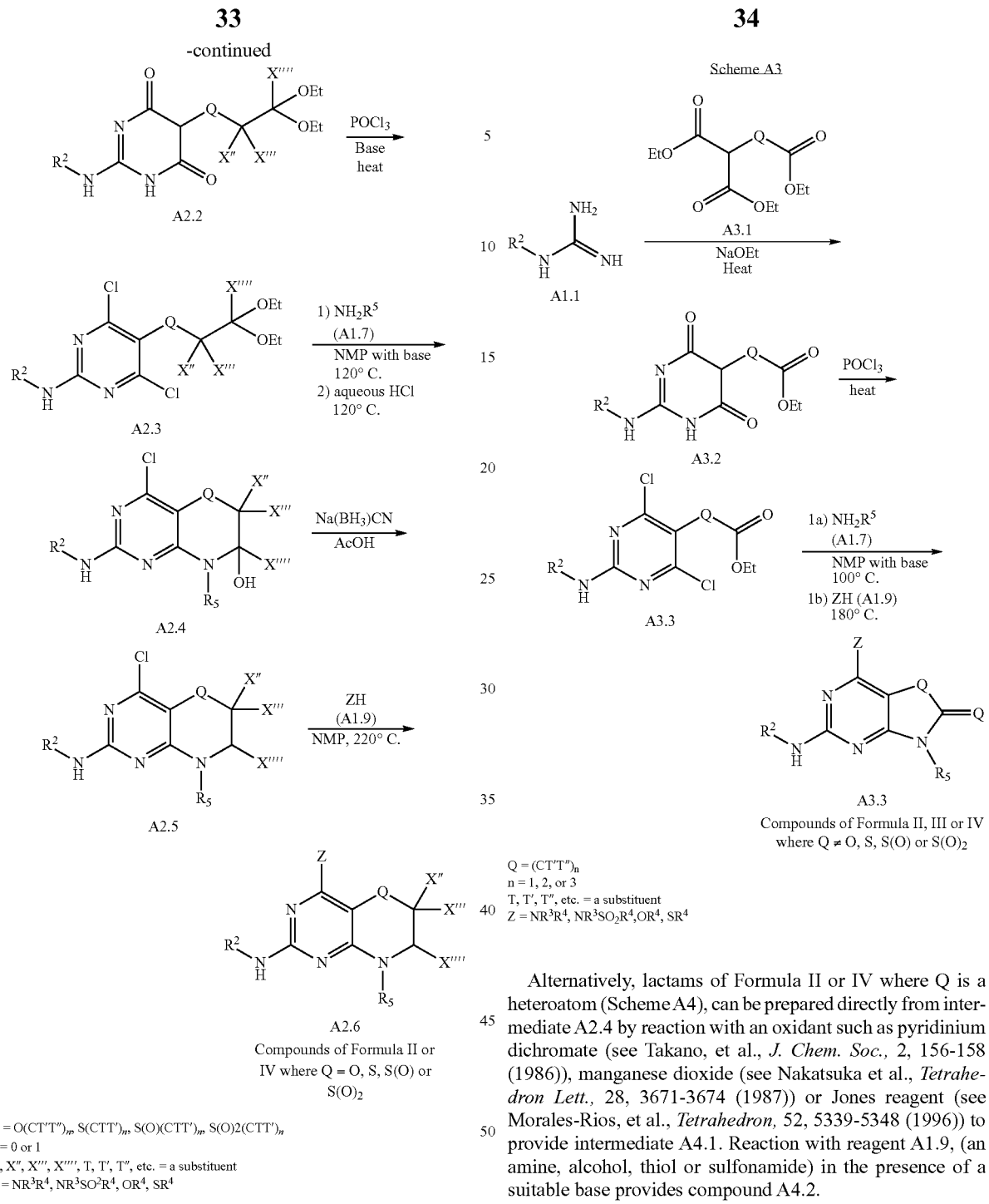

For the preparation of lactams of Formula II, III, or IV where Q is not a heteroatom (Scheme A3), guanidine A1.1 is heated in the presence of a base such as sodium ethoxide with an appropriate 2-substituted malonate A3.1 to produce intermediate A3.2. Reaction of A3.2 with phosphorous oxychloride at elevated temperature provides intermediate A3.3 which is then heated with amine A1.7 in the presence of a base such as triethylamine or Hunigs base in a solvent such as N-methyl pyrrolidone. Reagent A1.9 (an amine, alcohol, thiol or sulfonamide) is then added directly to the "same pot" and heated to provide compound A3.3 which is described by Formula II, III, or IV.

Alternatively, lactams of Formula II or IV where Q is a heteroatom (Scheme A4), can be prepared directly from intermediate A2.4 by reaction with an oxidant such as pyridinium dichromate (see Takano, et al., *J. Chem. Soc.*, 2, 156-158 (1986)), manganese dioxide (see Nakatsuka et al., *Tetrahedron Lett.*, 28, 3671-3674 (1987)) or Jones reagent (see Morales-Rios, et al., *Tetrahedron*, 52, 5339-5348 (1996)) to provide intermediate A4.1. Reaction with reagent A1.9, (an amine, alcohol, thiol or sulfonamide) in the presence of a suitable base provides compound A4.2.

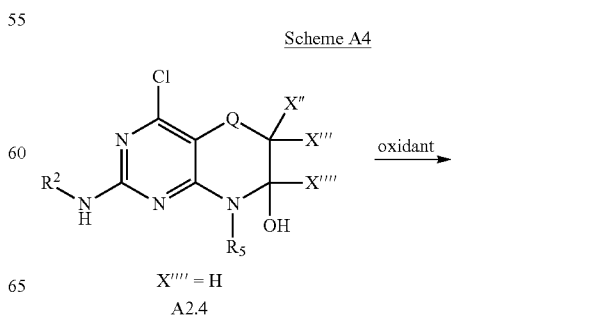

Scheme A4

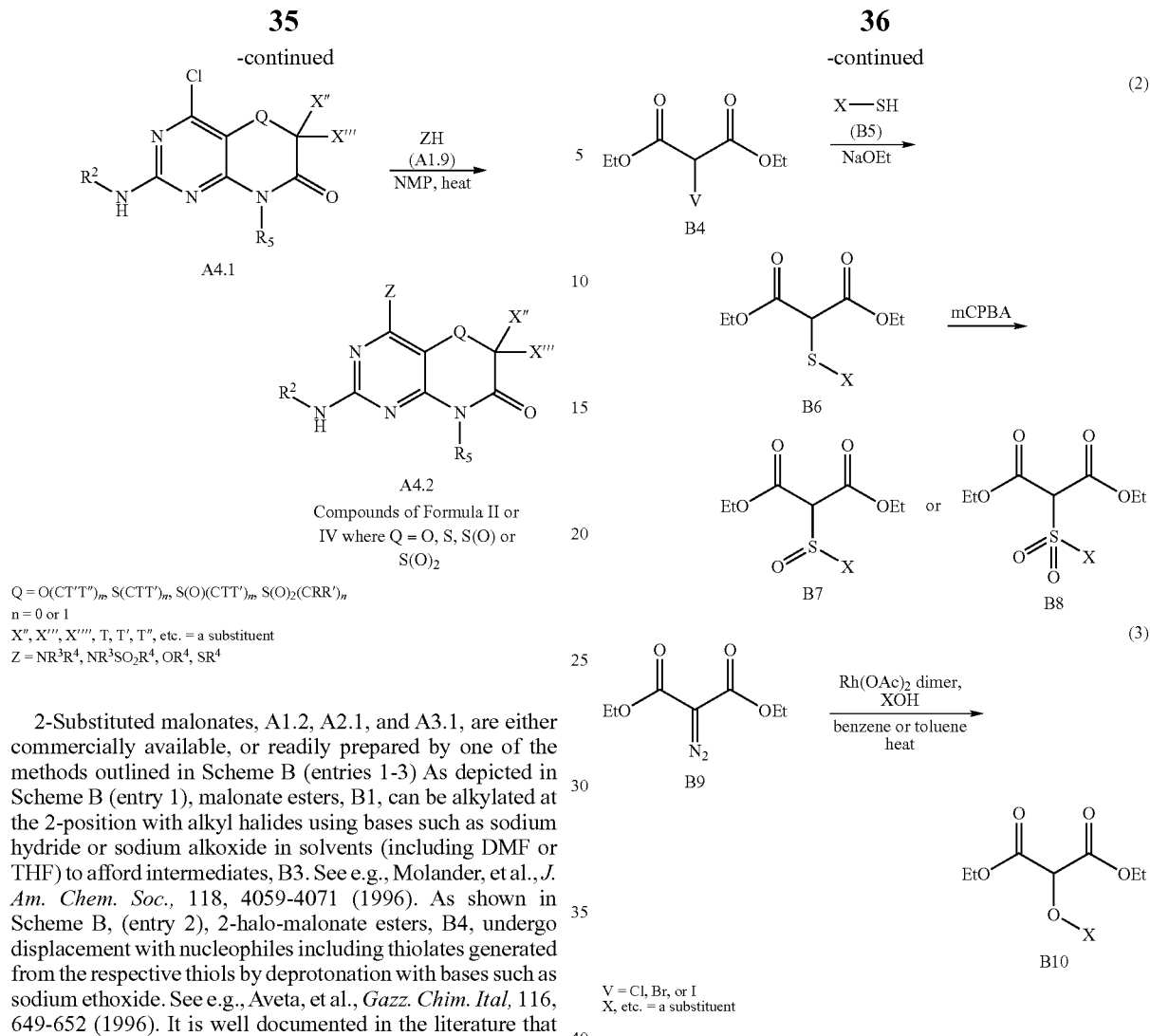

2-Substituted malonates, A1.2, A2.1, and A3.1, are either commercially available, or readily prepared by one of the methods outlined in Scheme B (entries 1-3) As depicted in Scheme B (entry 1), malonate esters, B1, can be alkylated at the 2-position with alkyl halides using bases such as sodium hydride or sodium alkoxide in solvents (including DMF or THF) to afford intermediates, B3. See e.g., Molander, et al., *J. Am. Chem. Soc.*, 118, 4059-4071 (1996). As shown in Scheme B, (entry 2), 2-halo-malonate esters, B4, undergo displacement with nucleophiles including thiolates generated from the respective thiols by deprotonation with bases such as sodium ethoxide. See e.g., Aveta, et al., *Gazz. Chim. Ital*, 116, 649-652 (1996). It is well documented in the literature that sulfides such as intermediate B6 can be selectively oxidized either to the sulfoxide, B7, or sulfone, B8, with oxidants (including m-chloroperoxybenzoic acid) by careful regulation of experimental conditions such as temperature. See e.g., Fujisawa, et al., *Tetrahedron Lett.*, 25, 5083-5086 (1984); and Sutton, et al., *Org. Lett.*, 2, 319-322 (2000). Additionally, as depicted in Scheme B (entry 3), 2-substituted malonates, B10, can be prepared by the reaction of diazomalonates with alcohols at elevated temperatures in solvents such as benzene, chloroform or toluene in the presence of transition metal catalysts, such as Rh(OAc)$_2$ dimer. See e.g., Connell, et al., *Tetrahedron*, 49, 5445-5460 (1993).

Scheme C outlines the conversion of esters of Formula (I) to amides of Formula (I). Hydrolysis of the ester C1.1 under basic conditions (using e.g., sodium hydroxide) affords acid C2. Alternatively, one may use a protecting group (such as a tert-butyl or benzyl group as depicted in compounds C1.2 and C2.3, respectively) which will readily allow removal (for instance, by treatment with trifluoroacetic acid or reaction with hydrogen in the presence of a suitable catalyst such as palladium on carbon under elevated pressure) to produce acid C2. See e.g., Greene, Theodora W., et al., *Protective Groups in Organic Synthesis*, 3$^{rd}$ ed. Coupling of acid C2 via standard amide bond coupling techniques (EDCI/HOAt) with the appropriate amine, C3, gives the desired amide, C4.

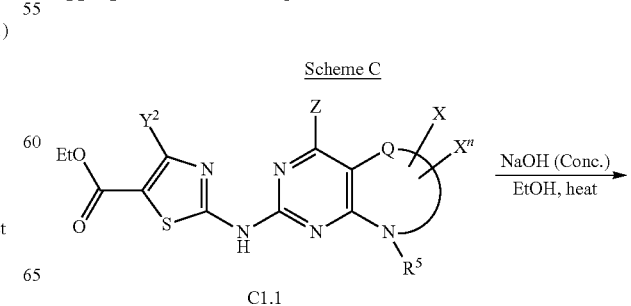

Scheme C

-continued

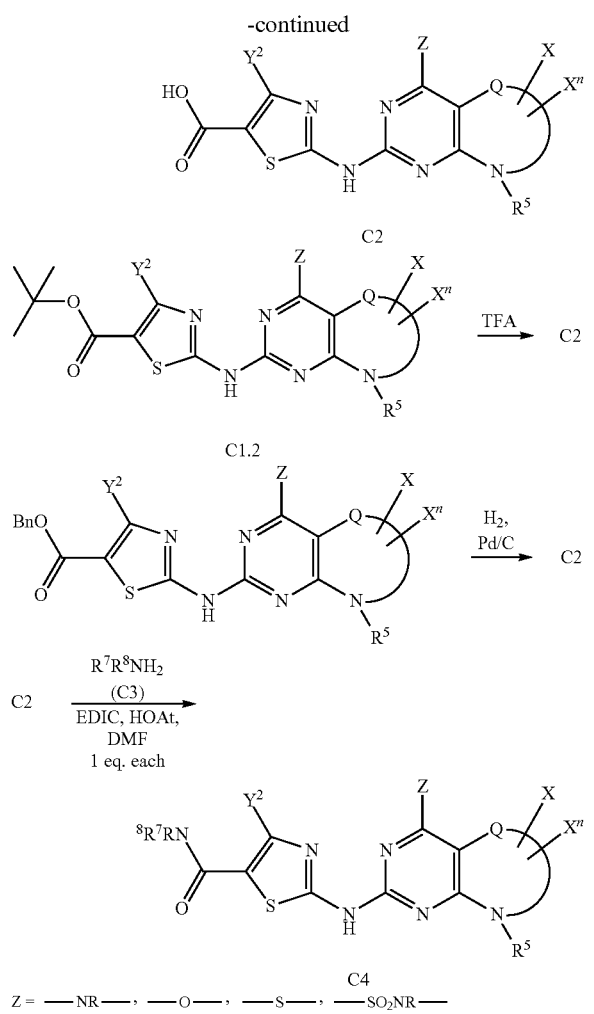

Z = —NR—, —O—, —S—, —SO$_2$NR—
R, X, X$^n$, Y$^2$, etc. = a substituent
n = an integer
Q = O, S, S(O), S(O)$_2$ or alkylene The appropriately substituted guanidines referred to in scheme A are either commercially available or readily prepared by a number of methods known to one skilled in the art of organic chemistry. As depicted in scheme D1, amines D1.1 may be reacted with a number of reagents, such as the commercially available 2-3,5-dimethylpyrazole-1-carboxamidine nitrate, D1.2, to provide the desired guanidine, D1.3.

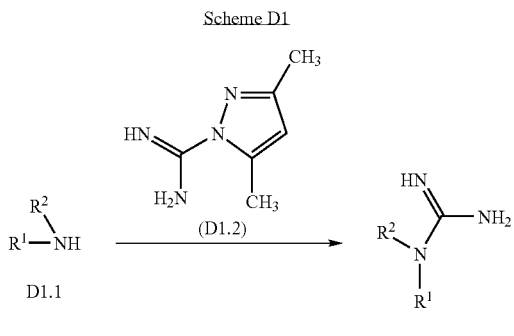

In some instances it is more convenient to prepare the intermediate guanidines as illustrated in Scheme D2. An alpha-haloketone, D2.1, is reacted with 2-imino-4-thiobiuret, D2.2, to provide guanidine salt D2.3, which is liberated by treatment with a basic resin, or sodium hydroxide, sodium methoxide, or an amine base to provide intermediate D2.4. Then, D2.4 can be further elaborated as described in Scheme A to provide compounds of Formula (I).

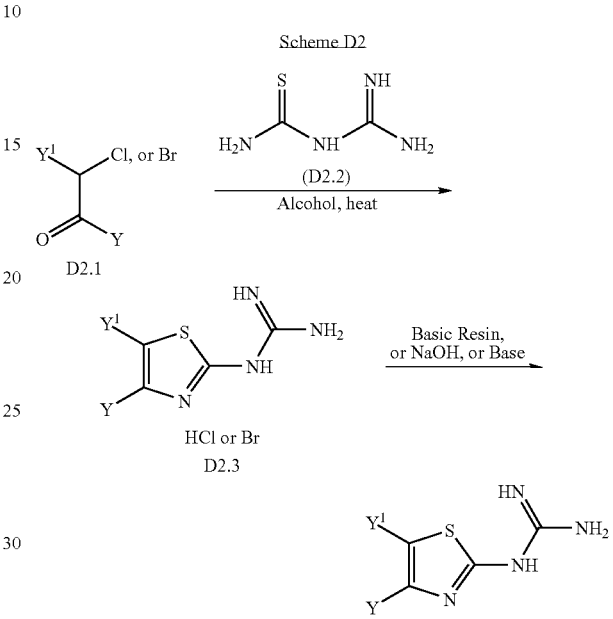

Utility

The compounds of Formula (I), are useful in the treatment (including prevention, partial alleviation or cure) of leukocyte activation-associated disorders. These disorders include (but are not limited to) transplant rejection (such as organ transplant, acute transplant, xenotransplant or heterograft or homograft such as is employed in burn treatment); protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell-mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituitarism; Guillain-Barre syndrome; other autoimmune diseases; glomerulonephritis; serum sickness; uticaria; allergic diseases such as respiratory allergies (e.g., asthma, hayfever, allergic rhinitis) or skin allergies; scleracierma; mycosis fungoides; acute inflammatory and respiratory responses (such as acute respiratory distress syndrome and ischemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic sclerosis; and morphea.

The term "leukocyte activation-associated disorder" or "leukocyte activation-mediated disorder" as used herein includes each of the above referenced diseases or disorders. The compounds of the present invention are useful for treating the aforementioned exemplary disorders irrespective of their etiology.

The present invention thus provides methods for the treatment of leukocyte activation-associated disorders (discussed above) comprising the step of administering to a subject in need thereof of at least one compounds of Formula (I). Other therapeutic agents such as those described below may be employed with the compounds of the present invention. In the methods of the present invention, such other therapeutic agent(s) may be administered prior to, simultaneously with or following the administration of the compound(s) of the present invention.

The methods of treating diseases which would benefit from administering compounds of Formula (I) alone or in combination with each other and/or other suitable therapeutic agents useful in treating such conditions. These agents include, without limitation: immunosuppressants such as cyclosporins (e.g., cyclosporin A), anti-IL-1 agents, such as Anakinra®, the IL-1 receptor antagonist, CTLA4-Ig, antibodies such as anti-ICAM-3, anti-IL-2 receptor (Anti-Tac®), anti-CD45RB, anti-CD2, anti-CD3, anti-CD4, anti-CD80, anti-CD86, monoclonal antibody OKT3, agents blocking the interaction between CD40 and CD154, such as antibodies specific for CD40 and/or CD154 (i.e., CD40L), fusion proteins constructed from CD40 and CD 154 (CD40Ig and CD8-CD154), interferon beta, interferon gamma, methotrexate, FK506 (tacrolimus, Prograf®), rapamycin (sirolimus or Rapamune®) mycophenolate mofetil, leflunomide (Arava®), azathioprine and cyclophosphamide, inhibitors, such as nuclear translocation inhibitors, of NF-kappa B function, such as deoxyspergualin (DSG), non-steroidal antiinflammatory drugs (NSAIDS) such as ibuprofen, cyclooxygenase-2 (COX-2) inhibitors such as celecoxib (Celebrex®) and rofecoxib (Vioxx®), or derivatives thereof, steroids such as prednisone or dexamethasone, gold compounds TNF-α inhibitors such as tenidap, anti-TNF antibodies or soluble TNF receptor such as etanercept (Enbrel®), inhibitors of p-38 kinase such as BIRB-796, RO-3201195, VX-850, and VX-750, beta-2 agonists such as albuterol, levalbuterol (Xopenex®), and salmeterol (Serevent®), inhibitors of leukotriene synthesis such as montelukast (Singulair®) and zarifukast (Accolate®), and anticholinergic agents such as ipratropium bromide (Atrovent®), PDE4 inhibitors such as Arofyline, Cilomilast, Roflumilast, C-11294A, CDC-801, BAY-19-8004, Cipamfylline, SCH351591, YM-976, PD-189659, Mesiopram, Pumafentrine, CDC-998, IC-485, and KW-4490, and PDE7 inhibitors such as IC242. See Lee, et al., *Cell Signalling*, 14, 277-284, (2002). Other compounds which may be used in combination with compounds of Formula (I) to treat diseases are disclosed in the following patent documents: WO 0068230, WO 0129049, WO 0132618, WO 0134601, WO 0136425, WO 0174786, WO 0198274, WO 0228847; U.S. Prov. Appl. Ser. Nos. 60/287,964, and 60/355,141; as well as anti-cytokines such as anti-IL-1 mAb or IL-1 receptor agonist; anti-IL-4 or IL-4 receptor fusion proteins; and PTK inhibitors such as those disclosed in U.S. Pat. Nos. 5,990,109, 6,235,740 and 6,239,133, U.S. Appl. Ser. No. 60/065,042 and Ser. No. 09/173,413, filed Nov. 10, 1997 and Oct. 15, 1998, respectively. All of the foregoing patents and patent applications are incorporated herein by reference in their entirety.

See also the following documents and references cited therein: Hollenbaugh, D., et al., *J. Immunol. Methods*, 188(1), 1-7 (1995); Hollenbaugh, D., et al., *EMBO J.*, 11(12), 4313-4321 (1992); and Moreland, L. W., et al., *New England J. of Medicine*, 337(3), 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

Use of the compounds having Formula (I) of the present invention in treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituitarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ischemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic sclerosis; and morphea.

The combined activity of the present compounds towards T-cells may be of value in the treatment of any of the aforementioned disorders.

In a particular embodiment, the compounds of the present invention are useful for the treatment of the aforementioned exemplary disorders irrespective of their etiology, for example, in the treatment of transplant rejection, rheumatoid arthritis, multiple sclerosis, chronic obstructive pulmonary disease, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, respiratory diseases such as asthma, COPD and bronchitis or atopic dermatitis.

T-Cell Proliferation Assay

Peripheral blood mononuclear cells (PBMC) were isolated from whole blood by density gradient centrifugation over Lymphoprep, 1.077. Cells were plated into 96 well U-bottom plates at 2.5×10$_5$ cells/well in 10% FBS RPMI 1640 (Life Technologies/Gibco-BRL) containing 10 ug/ml anti-CD3 (G19-4, Bristol-Myers Squibb P.R.I., Princeton, N.J.) and 1 ug/ml anti-CD28 (9.3, Bristol-Myers Squibb P.R.I.) in the presence and absence of inhibitors. DMSO (used as a solvent for inhibitors) was added to the medium at 0.1% final concentration. The total volume per well was 200 µL. Cells were incubated at 37 C 5% CO2 for 3 days, at which time 0.5 µCi of $^3$H-thymidine was added to each well. Six hours following the addition of $^3$H-thymidine, the plates were harvested onto filter plates, 30 ul EcoLite scintillant (ICN, Costa Mesa, Calif.) was added per well, and plates read on a Top Count-NXT scintillation counter.

TNFα Secretion Assay

The ability of compounds to inhibit the production and secretion of TNFα from leukocytes was performed using either PBMC (obtained as described above) or the THP-1 cell line as a source of monocytes. Compounds were diluted in RPMI 1640 supplemented with 10% FBS and DMSO at a final concentration of 0.2%. Cells (2×10$^5$/well in U-bottom 96 well plates) were pre-incubated with compounds for 30 min at 37 C prior to addition of lipopolysaccharide (LPS) at a final concentration of 6.25 ng/ml in a total volume of 200 µL. After 4 h at 37° C., 50 µL of supernatant was carefully aspirated for detection of soluble TNFα. Soluble TNFα was detected by ELISA developed by R&D Systems (Minneapolis, Minn.) according to the manufacturer's instructions.

EXAMPLES

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by the example only where the compound is the title compound of the example (for example, "A2" denotes the title compound of Example A2).

Abbreviations
Ac Acetyl
AcOH Acetic acid
aq. Aqueous
CDI Carbonyldiimidazole
Bn Benzyl
Bu Butyl
Boc tert-butoxycarbonyl
DMAP Dimethylaminopyridine
DMA N,N-Dimethylacetamide
DMF dimethylformamide
DMSO Dimethylsulfoxide
EDC 1-(3-Dimethylaminopropyl)-3-ethylcarbodiimide hydrochloride
EtOAc Ethyl acetate
Et Ethyl
EtOH Ethanol
H Hydrogen
h Hours
i iso
HPLC High pressure liquid chromatography
HOAc Acetic acid
Lawesson's Reagent [2,4-bis(4-methoxyphenyl)-1,3-dithia-2,4-diphosphetane-2-4-disulfide
LC liquid chromatography
Me Methyl
MeOH Methanol
min. Minutes
M$^+$ (M+H)$^+$
M$^{+1}$ (M+H)$^+$
MS Mass spectrometry
n normal
Pd/C Palladium on carbon
Ph Phenyl
Pr Propyl
Ret Time Retention time
rt or RT Room temperature
sat. Saturated
S-Tol-BINAP (S)-(−)-2,2'-Bis(di-p-tolylphosphino)-1,1'-binapthyl
t tert
TFA Trifluoroacetic acid
THF Tetrahydrofuran
YMC YMC Inc, Wilmington, N.C. 28403

Example A1

2-[4-(4-Hydroxy-piperidin-1-yl)-7-pyridin-2-ylmethyl-5,6-dihydro-pyrrolo[2,3-d]pyrimidin-2-ylamino]-4-methyl-thiazole-5-carboxylic acid ethyl ester

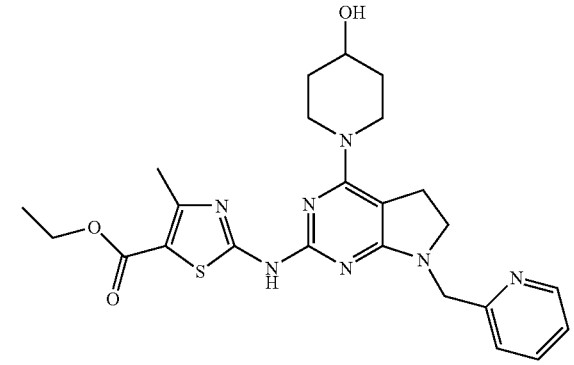

A1.1: 2-[(Aminoiminomethyl)amino]-4-methyl-5-thiazolecarboxylic acid ethyl ester

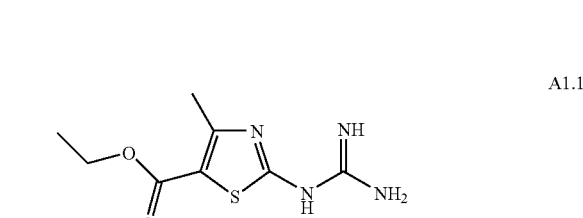

A1.1

A solution of 2-imino-4-thiobiuret (20.0 g, 0.17 mol), 2-chloroacetoacetate (28 g, 0.17 mol) in ethanol (500 mL)

was heated to 100° C. for 4 hours. The reaction mixture was concentrated to half volume and poured into 1 liter of 1N NaOH. The white solid which precipitated out was collected by filtration and dried under vacuum to yield A1.1 (30.5 g, 79%). $^1$H-NMR (DMSO-$d_6$) δ: 4.22 (2H, q, J=7 Hz), 2.50 (3H, merge with DMSO), 1.26 (3H, t, J=7 Hz). HPLC: 97.7%, ret. time=1.619 min., LC/MS (M+H)$^+$=229.

A1.2: 2-(5-Allyl-4,6-dioxo-1,4,5,6-tetrahydro-pyrimidin-2-ylamino)-4-methyl-thiazole-5-carboxylic acid ethyl ester

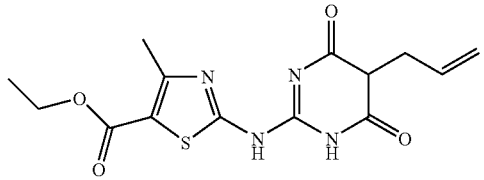

A1.2

To a solution of NaOEt in EtOH [prepared by dissolving Na (88 mg, 3.83 mmol, 2.5 eq) in 15 mL of absolute ethanol] was added A1.1 (350 mg, 1.53 mmol, 1 eq) and the mixture was stirred at rt for 20 min. Diethyl allylmalonate (0.30 mL, 1.53 mmol, 1 eq) was added dropwise, the reaction mixture was heated at reflux for 22 h and then cooled and poured onto a mixture of ice and 10% aq $H_2SO_4$. The solid was collected by filtration, washed with water and dried to afford A1.2 (346 mg, 67% yield) as a tan solid. LC/MS: 337.58 [M+H]$^+$; HPLC: 93% at 3.49 min (Phenomenex Luna 5 μm C18 column 4.6×50 mm, 10-90% aqueous methanol over 4 min containing 0.2% phosphoric acid, 4 mL/min, monitoring at 220 nm).

A1.3: 2-(5-Allyl-4,6-dichloro-pyrimidin-2-ylamino)-4-methyl-thiazole-5-carboxylic acid ethyl ester

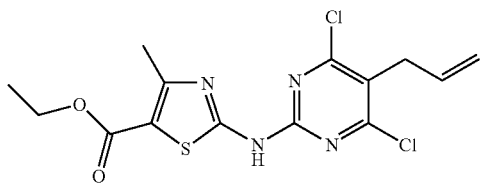

A1.3

A mixture of A1.2 (346 mg, 1.03 mmol, 1 eq) and POCl$_3$ (5 mL) was heated in a 100° C. oil bath for 19 h. The reaction mixture was poured onto ice, neutralized with 2 N NaOH, and extracted with ethyl acetate. The organic phase was washed with sat. NaHCO$_3$, water and brine, dried over MgSO$_4$ and concentrated to afford A1.3 (285 mg, 74% yield) as a yellow solid. LC/MS: 337.58 [M+H]$^+$; HPLC: >95% at 2.10 min (Xterra 5 μm C18 column 4.6×30 mm, 10-90% aqueous methanol over 2 min containing 0.2% phosphoric acid, 5 mL/min, monitoring at 254 nm). $^1$H NMR (400 MHz, DMSO-$d_6$): δ 5.90 (m, 1H), 5.10 (m, 2H), 4.27 (q, J=7.1 Hz, 2H), 3.53 (m, 2 H), 2.55 (s, 3H), 1.29 (t, J=7.1 Hz, 3H).

A1.4: 2-[4,6-Dichloro-5-(2-oxo-ethyl)-pyrimidin-2-ylamino]-4-methyl-thiazole-5-carboxylic acid ethyl ester

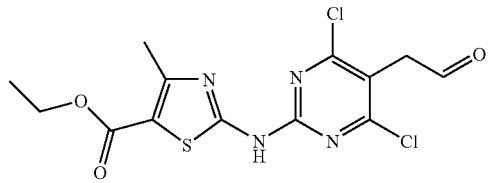

A1.4

A solution of A1.3 (109 mg, 0.292 mmol, 1 eq) and NMO monohydrate (79 mg, 0.584 mmol, 2 eq) in THF/H$_2$O (6:1, 6.4 mL) was cooled to 0° C. and a 4 wt % aq solution of OsO$_4$ (0.18 mL, 0.029 mmol, 0.1 eq) was added. The reaction mixture was warmed to rt, stirred for 41 h and then quenched with a solution of 80 mg of NaHSO$_3$ in 5 mL H$_2$O and extracted twice with ethyl acetate. The organic phase was washed with water and brine, dried over Na$_2$SO$_4$ and concentrated.

The crude product in THF/ethanol/water (4:1:2, 5 mL) was cooled to 0° C., NaIO$_4$ (125 mg, 0.584 mmol, 2 eq) was added portionwise and the reaction mixture was stirred at 0° C. for 3 h and then warmed to rt and stirred overnight. The mixture was poured into water and extracted with ethyl acetate. The organic layer was washed with brine, dried over Na$_2$SO$_4$ and concentrated. The crude product was passed through a silica gel plug eluted first with dichloromethane (discarded) and then with ethyl acetate. The ethyl acetate fractions were concentrated to afford A1.4 (85 mg, 78% yield) as a white solid. HPLC: >95% at 3.58 min (Phenomenex Luna 5 μm C18 column 4.6×50 mm, 10-90% aqueous methanol over 4 min containing 0.2% phosphoric acid, 4 mL/min, monitoring at 254 nm). $^1$H NMR (400 MHz, DMSO-$d_6$): δ 9.72 (s, 1H), 4.27 (q, J=7.1 Hz, 2H), 4.11 (m, 2H), 2.56 (s, 3H), 1.29 (t, J=7.1 Hz, 3H).

A1.5: 2-(4-Chloro-7-pyridin-2-ylmethyl-5,6-dihydro-pyrrolo[2,3-d]pyrimidin-2-ylamino)-4-methyl-thiazole-5-carboxylic acid ethyl ester

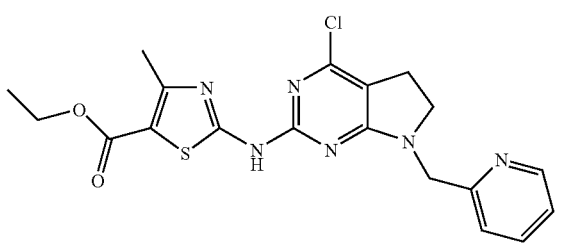

A1.5

A mixture of A1.4 (34 mg, 0.0911 mmol, 1 eq) in THF (1 mL) was treated with 2-picolylamine (10.3 mg, 0.0957 mmol, 1.05 eq), Na(OAc)$_3$BH (29 mg, 0.137 mmol, 1.5 eq) and acetic acid (5.2 μL, 0.0911 mmol, 1 eq). The reaction mixture was stirred at rt for 10 min, 3 drops of Et₃N were added and stirring continued for 1 h. The mixture was poured into sat. NaHCO₃, extracted twice with ethyl acetate and the combined organic layers were washed with brine, dried over Na₂SO₄ and concentrated. Column chromatography (SiO₂, eluted with ethyl acetate) gave A1.5 (25 mg, 64% yield) as an off-white solid. LC/MS: 431.46 [M+H]⁺; HPLC: >95% at 3.20 min (Phenomenex Luna 5 μm C18 column 4.6×50 mm, 10-90% aqueous methanol over 4 min containing 0.2% phosphoric acid, 4 mL/min, monitoring at 254 nm). ¹H NMR (400 MHz, CDCl₃): δ 9.53 (brs, 1H), 8.58 (d, J=4.9 Hz, 1H), 7.67 (ddd, J=1.7, 7.7, 7.7 Hz, 1H), 7.37 (d, J=7.7 Hz, 1H), 7.22 (m, 1H), 4.79 (s, 2H), 4.28 (q, J=7.1 Hz, 2H), 3.77 (t, J=8.4 Hz, 2H), 3.03 (J=8.2 Hz, 2H), 2.65 (s, 3H), 1.30 (t, J=7.1 Hz, 3H).

A1.6: 2-[4-(4-Hydroxy-piperidin-1-yl)-7-pyridin-2-ylmethyl-5,6-dihydro-pyrrolo[2,3-d]pyrimidin-2-ylamino]-4-methyl-thiazole-5-carboxylic acid ethyl ester A mixture of A1.5 (15 mg, 0.0348 mmol, 1 eq), 4-hydroxypiperidine (7 mg, 0.0696 mmol, 2 eq), Hunig's base (18 μL, 0.1044 mmol, 3 eq) and n-butanol (0.5 mL) was heated in a sealed tube at 150° C. until the reaction was complete by HPLC analysis. The reaction mixture was cooled to rt and concentrated in vacuo. Column chromatography (SiO₂, 5% methanol/ethyl acetate) provided A1 (10.4 mg, 60% yield) as an oil. LC/MS: 496.57 [M+H]⁺; HPLC: 95% at 1.22 min (Xterra 5 μm C18 column 4.6×30 mm, 10-90% aqueous methanol over 2 min containing 0.2% phosphoric acid, 5 mL/min, monitoring at 254 nm). ¹H NMR (400 MHz, CDCl₃): δ 8.70 (brs, 1H), 8.55 (d, J=4.7 Hz, 1H), 7.63 (ddd, J=1.7, 7.7, 7.7 Hz, 1H), 7.33 (d, J=7.8 Hz, 1H), 7.18 (m, 1H), 4.69 (s, 2H), 4.26 (q, J=7.1 Hz, 2H), 4.15-4.20 (m, 2H), 3.94 (m, 1H), 3.53 (t, J=8.4 Hz, 2H), 3.28 (m, 2H), 3.09 (J=8.4 Hz, 2H), 2.60 (s, 3H), 1.96 (m, 2H), 1.58 (m, 2H), 1.31 (t, J=7.1 Hz, 3H).

Example A2-A72

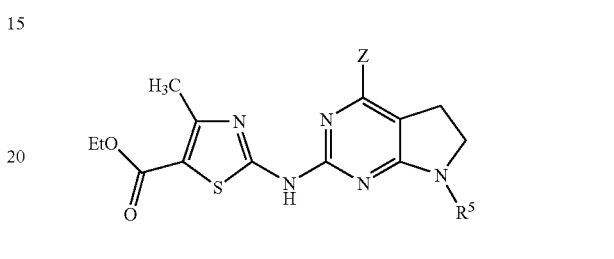

Examples A2 to A72 were prepared from intermediate A1.4 in a similar manner to that used for Example A1 utilizing the appropriate amine replacements.

TABLE A

| Ex. | Z | R⁵ | Name | HPLC Retention (min) | MS Reported |
|---|---|---|---|---|---|
| A2 | piperazin-1-yl (HN-piperazine) | 4-(methanesulfonyl)benzyl | 2-[7-(4-Methanesulfonyl-benzyl)-4-piperazin-1-yl-5,6-dihydro-pyrrolo[2,3-d]pyrimidin-2-ylamino]-4-methyl-thiazole-5-carboxylic acid ethyl ester | 1.19ᵃ | 558.44 |
| A3 | piperazin-1-yl (HN-piperazine) | 3,4,5-trimethoxybenzyl | 4-Methyl-2-[4-piperazin-1-yl-7-(3,4,5-trimethoxy-benzyl)-5,6-dihydro-pyrrolo[2,3-d]pyrimidin-2-ylamino]-thiazole-5-carboxylic acid ethyl ester | 1.35ᵃ | 570.24 |
| A4 | 4-methyl-piperazin-1-yl | 3,4,5-trimethoxybenzyl | 4-Methyl-2-[4-(4-methyl-piperazin-1-yl)-7-(3,4,5-trimethoxy-benzyl)-5,6-dihydro-pyrrolo[2,3-d]pyrimidin-2-ylamino]-thiazole-5-carboxylic acid ethyl ester | 1.34ᵃ | 584.56 |

TABLE A-continued

| Ex. | Z | R⁵ | Name | HPLC Retention (min) | MS Reported |
|---|---|---|---|---|---|
| A5 | 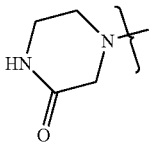 | 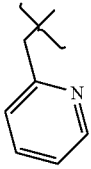 | 4-Methyl-2-[4-(3-oxo-piperazin-1-yl)-7-pyridin-2-ylmethyl-5,6-dihydro-pyrrolo[2,3-d]pyrimidin-2-ylamino]-thiazole-5-carboxylic acid ethyl ester | 1.18[a] | 495.51 |
| A6 | 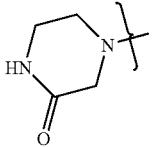 | 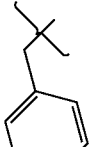 | 2-[7-(4-Methanesulfonyl-benzyl)-4-(3-oxo-piperazin-1-yl)-5,6-dihydro-pyrrolo[2,3-d]pyrimidin-2-ylamino]-4-methyl-thiazole-5-carboxylic acid ethyl ester | 2.93[b] | 572.31 |
| A7 | 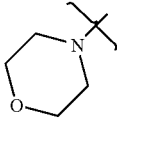 | 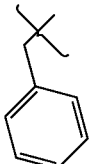 | 2-[7-(4-Methanesulfonyl-benzyl)-4-morpholin-4-yl-5,6-dihydro-pyrrolo[2,3-d]pyrimidin-2-ylamino]-4-methyl-thiazole-5-carboxylic acid ethyl ester | 3.02[b] | 559.32 |
| A8 | 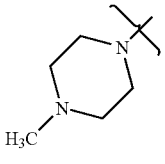 | 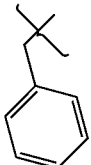 | 2-[7-(4-Methanesulfonyl-benzyl)-4-(4-methyl-piperazin-1-yl)-5,6-dihydro-pyrrolo[2,3-d]pyrimidin-2-ylamino]-4-methyl-thiazole-5-carobxylic acid ethyl ester | 2.41[b] | 572.47 |
| A9 | 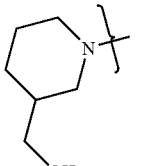 | 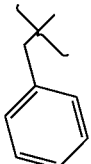 | 2-[4-(3-Hydroxymethyl-piperidin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester | 2.83[b] | 587.32 |
| A10 | 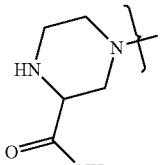 | 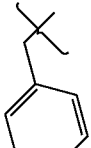 | 2-[4-(3-Carbamoyl-piperazin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester | 2.35[b] | 601.32 |

TABLE A-continued

| Ex. | Z | R⁵ | Name | HPLC Retention (min) | MS Reported |
|---|---|---|---|---|---|
| A11 | (4-hydroxymethyl-piperidin-1-yl) | (4-methanesulfonyl-benzyl) | 2-[4-(4-Hydroxymethyl-piperidin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester | 2.73[b] | 587.30 |
| A12 | (4-dimethylamino-piperidin-1-yl) | (4-methanesulfonyl-benzyl) | 2-[4-(4-Dimethylamino-piperidin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester | 2.17[b] | 600.37 |
| A13 | (4-hydroxy-3-hydroxymethyl-piperidin-1-yl) | (4-methanesulfonyl-benzyl) | 2-[4-(4-Hydroxy-3-hydroxymethyl-piperidin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester | 2.57[b] | 603.37 |
| A14 | N(CH₃)₂ | (4-methanesulfonyl-benzyl) | 2-[4-Dimethylamino-7-(4-methanesulfonyl-benzyl)-5,6-dihydro-pyrrolo[2,3-d]pyrimidin-2-ylamino]-4-methyl-thiazole-5-carboxylic acid ethyl ester | 2.78[b] | 517.30 |
| A15 | NH(CH₃) | (4-methanesulfonyl-benzyl) | 2-[7-(4-Methanesulfonyl-benzyl)-4-methylamino-5,6-dihydro-pyrrolo[2,3-d]pyrimidin-2-ylamino]-4-methyl-thiazole-5-carboxylic acid ethyl ester | 2.64[b] | 503.44 |

TABLE A-continued

| Ex. | Z | R⁵ | Name | HPLC Retention (min) | MS Reported |
|---|---|---|---|---|---|
| A16 | 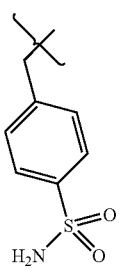 | 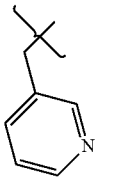 | 4-Methyl-2-[4-(3-oxo-piperazin-1-yl)-7-(4-sulfamoyl-benzyl)-5,6-dihydro-pyrrolo[2,3-d]pyrimidin-2-ylamino]-thiazole-5-carboxylic acid ethyl ester | 2.78$^b$ | 573.20 |
| A17 | 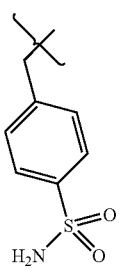 | 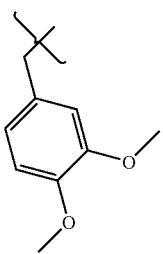 | 4-Methyl-2-[4-(3-oxo-piperazin-1-yl)-7-pyridin-3-ylmethyl-5,6-dihydro-pyrrolo[2,3-d]pyrimidin-2-ylamino]-thiazole-5-carboxylic acid ethyl ester | 2.29$^b$ | 495.25 |
| A18 | 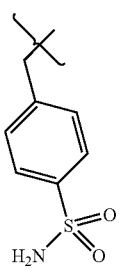 | 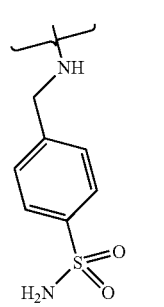 | 2-[7-(3,4-Dimethoxy-benzyl)-4-(3-oxo-piperazin-1-yl)-5,6-dihydro-pyrrolo[2,3-d]pyrimidin-2-ylamino]-4-methyl-thiazole-5-carboxylic acid ethyl ester | 3.24$^b$ | 554.51 |
| A19 | 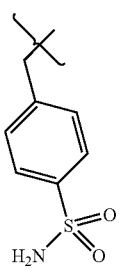 | Et | 2-[7-Ethyl-4-(3-oxo-piperazin-1-yl)-5,6-dihydro-pyrrolo[2,3-d]pyrimidin-2-ylamino]-4-methyl-thiazole-5-carboxylic acid ethyl ester | 2.86$^b$ | 432.26 |
| A20 | 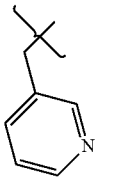 | Et | 2-[7-Ethyl-4-(4-sulfamoyl-benzylamino)-5,6-dihydro-pyrrolo[2,3-d]pyrimidin-2-ylamino]-4-methyl-thiazole-5-carboxylic acid ethyl ester | 2.77$^b$ | 518.21 |
| A21 | 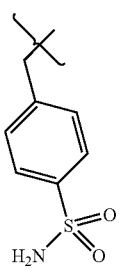 | 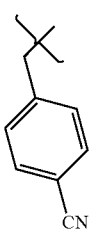 | 2-[7-(4-Cyano-benzyl)-4-(3-oxo-piperazin-1-yl)5,6-dihydro-pyrrolo[2,3-d]pyrimidin-2-ylamino]-4-methyl-thiazole-5-carboxylic acid ethyl ester | 3.31$^b$ | 519.20 |

TABLE A-continued

| Ex. | Z | R[5] | Name | HPLC Retention (min) | MS Reported |
|---|---|---|---|---|---|
| A22 | 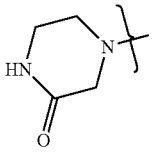 | 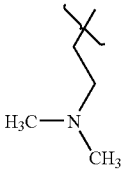 | 2-[7-(2-Dimethylamino-ethyl)-4-(3-oxo-piperazin-1-yl)-5,6-dihydro-pyrrolo[2,3-d]pyrimidin-2-ylamino]-4-methyl-thiazole-5-carboxylic acid ethyl ester | 2.21[b] | 475.28 |
| A23 | 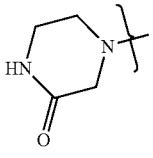 | 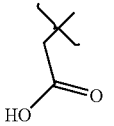 | 2-[7-Carboxymethyl-4-(3-oxo-piperazin-1-yl)-5,6-dihydro-pyrrolo[2,3-d]pyrimidin-2-ylamino]-4-methyl-thiazole-5-carboxylic acid ethyl ester | 2.65[b] | 462.22 |
| A24 | 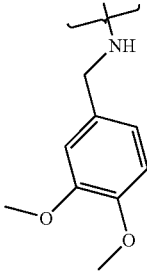 | 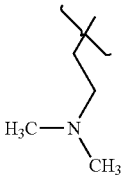 | 2-[7-(2-Dimethylamino-ethyl)-4-(3,4,5-trimethoxy-benzylamino)-5,6-dihydro-pyrrolo[2,3-d]pyrimidin-2-ylamino]-4-methyl-thiazole-5-carboxylic acid ethyl ester | 2.52[b] | 572.32 |
| A25 | 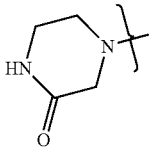 | 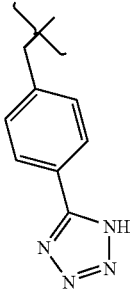 | 4-Methyl-2-{4-(3-oxo-piperazin-1-yl)-7-[4-(1H-tetrazol-5-yl)-benzyl]-5,6-dihydro-pyrrolo[2,3-d]pyrimidin-2-ylamino}-thiazole-5-carboxylic acid ethyl ester | 3.07[b] | 562.23 |
| A26 | 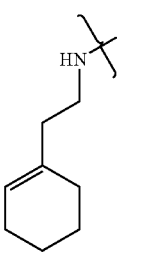 | 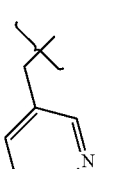 | 2-[4-(2-Cyclohex-1-enyl-ethylamino)-7-pyridin-3-ylmethyl-5,6-dihydro-pyrrolo[2,3-d]pyrimidin-2-ylamino]-4-methyl-thiazole-5-carboxylic acid ethyl ester | 1.69[c] | 520.25 |
| A27 | 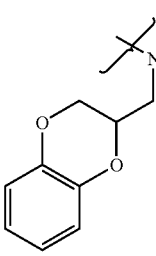 |  | 2-{4-[(2,3-Dihydro-benzo[1,4]dioxin-2-ylmethyl)-amino]-7-pyridin-3-ylmethyl-5,6-dihydro-pyrrolo[2,3-d]pyrimidin-2-ylamino}-4-methyl-thiazole-5-carboxylic acid ethyl ester | 1.61[c] | 560.24 |

TABLE A-continued

| Ex. | Z | R⁵ | Name | HPLC Retention (min) | MS Reported |
|---|---|---|---|---|---|
| A28 | 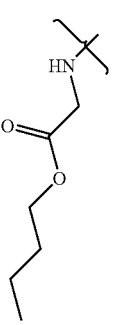 | 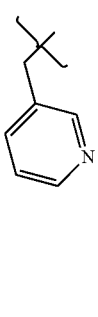 | 2-[4-(Butoxycarbonylmethyl-amino)-7-pyridin-3-ylmethyl-5,6-dihydro-pyrrolo[2,3-d]pyrimidin-2-ylamino]-4-methyl-thiazole-5-carboxylic acid ethyl ester | 1.49ᶜ | 526.27 |
| A29 | 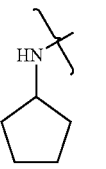 | 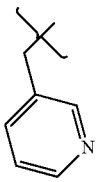 | 2-(4-Cyclopentylamino-7-pyridin-3-ylmethyl-5,6-dihydro-pyrrolo[2,3-d]pyrimidin-2-ylamino)-4-methyl-thiazole-5-carboxylic acid ethyl ester | 1.46ᶜ | 480.26 |
| A30 | 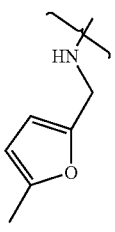 | 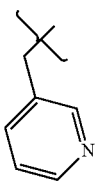 | 4-Methyl-2-{4-[(5-methyl-furan-2-ylmethyl)-amino]-7-pyridin-3-ylmethyl-5,6-dihydro-pyrrolo[2,3-d]pyrimidin-2-ylamino}-thiazole-5-carboxylic acid ethyl ester | 1.47ᶜ | 506.25 |
| A31 | 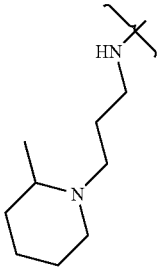 | 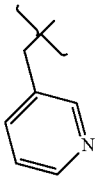 | 4-Methyl-2-{4-[3-(2-methyl-piperidin-1-yl)-propylamino]-7-pyridin-3-ylmethyl-5,6-dihydro-pyrrolo[2,3-d]pyrimidin-2-ylamino}-thiazole-5-carboxylic acid ethyl ester | 1.17ᶜ | 551.31 |
| A32 | 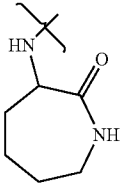 | 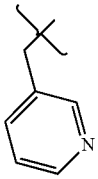 | 4-Methyl-2-[4-(2-oxo-azepan-3-ylamino)-7-pyridin-3-ylmethyl-5,6-dihydro-pyrrolo[2,3-d]pyrimidin-2-ylamino]-thiazole-5-carboxylic acid ethyl ester | 1.38ᶜ | 523.27 |
| A33 | 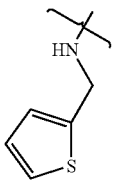 | 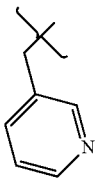 | 4-Methyl-2-{7-pyridin-3-ylmethyl-4-[(thiophen-2-ylmethyl)-amino]-5,6-dihydro-pyrrolo[2,3-d]pyrimidin-2-ylamino}-thiazole-5-carboxylic acid ethyl ester | 1.46ᶜ | 508.19 |

TABLE A-continued

| Ex. | Z | R⁵ | Name | HPLC Retention (min) | MS Reported |
|---|---|---|---|---|---|
| 34 | 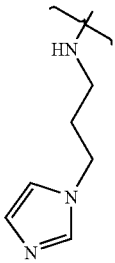 | 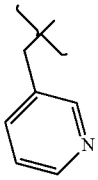 | 2-[4-(3-Imidazol-1-yl-propylamino)-7-pyridin-3-ylmethyl-5,6-dihydro-pyrrolo[2,3-d]pyrimidin-2-ylamino]-4-methyl-thiazole-5-carboxylic acid ethyl ester | 1.08$^c$ | 520.25 |
| A35 | 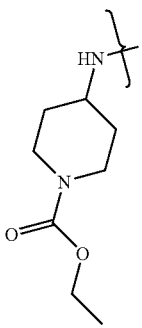 | 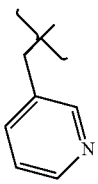 | 4-Methyl-2-[4-(1-carboxyethyl-piperidin-4-ylamino)-7-pyridin-3-ylmethyl-5,6-dihydro-pyrrolo[2,3-d]pyrimidin-2-ylamino]-thiazole-5-carboxylic acid ethyl ester | 1.53$^c$ | 567.29 |
| A36 | 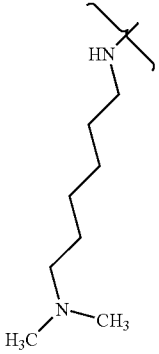 | 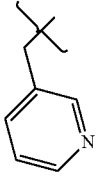 | 2-[4-(6-Dimethylamino-hexylamino)-7-pyridin-3-ylmethyl-5,6-dihydro-pyrrolo[2,3-d]pyrimidin-2-ylamino]-4-methyl-thiazole-5-carboxylic acid ethyl ester | 1.19$^c$ | 539.33 |
| A37 | 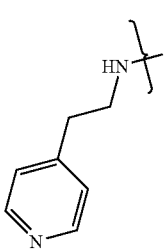 | 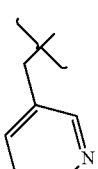 | 4-Methyl-2-[4-(2-pyridin-4-yl-ethylamino)-7-pyridin-3-ylmethyl-5,6-dihydro-pyrrolo[2,3-d]pyrimidin-2-ylamino]-thiazole-5-carboxylic acid ethyl ester | 1.10$^c$ | 517.24 |
| A38 | 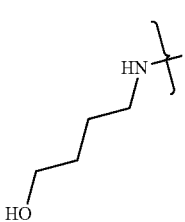 | 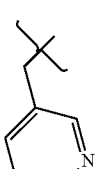 | 2-[4-(4-Hydroxy-butylamino)-7-pyridin-3-ylmethyl-5,6-dihydro-pyrrolo[2,3-d]pyrimidin-2-ylamino]-4-methyl-thiazole-5-carboxylic acid ethyl ester | 1.22$^c$ | 484.25 |

TABLE A-continued

| Ex. | Z | R⁵ | Name | HPLC Retention (min) | MS Reported |
|---|---|---|---|---|---|
| A39 | 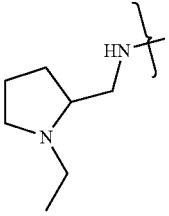 | 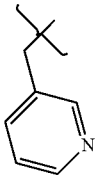 | 2-{4-[(1-Ethyl-pyrrolidin-2-ylmethyl)-amino]-7-pyridin-3-ylmethyl-5,6-dihydro-pyrrolo[2,3-d]pyrimidin-2-ylamino}-4-methyl-thiazole-5-carboxylic acid ethyl ester | 1.20$^c$ | 523.24 |
| A40 | 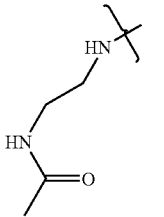 | 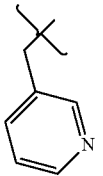 | 2-[4-(2-Acetylamino-ethylamino)-7-pyridin-3-ylmethyl-5,6-dihydro-pyrrolo[2,3-d]pyrimidin-2-ylamino]-4-methyl-thiazole-5-carboxylic acid ethyl ester | 1.19$^c$ | 497.24 |
| A41 | 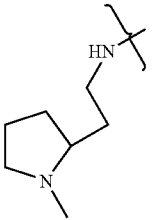 | 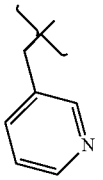 | 4-Methyl-2-{4-[2-(1-methyl-pyrrolidin-2-yl)-ethylamino]-7-pyridin-3-ylmethyl-5,6-dihydro-pyrrolo[2,3-d]pyrimidin-2-ylamino}-thiazole-5-carboxylic acid ethyl ester | 1.13$^c$ | 523.30 |
| A42 | 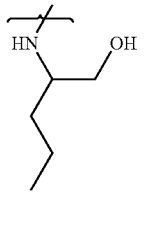 | 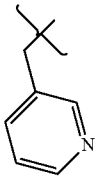 | 2-[4-(1-Hydroxymethyl-butylamino)-7-pyridin-3-ylmethyl-5,6-dihydro-pyrrolo[2,3-d]pyrimidin-2-ylamino]-4-methyl-thiazole-5-carboxylic acid ethyl ester | 1.40$^c$ | 498.27 |
| A43 | 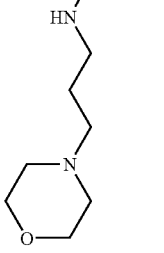 | 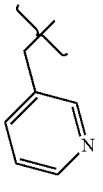 | 4-Methyl-2-[4-(3-morpholin-4-yl-propylamino)-7-pyridin-3-ylmethyl-5,6-dihydro-pyrrolo[2,3-d]pyrimidin-2-ylamino]-thiazole-5-carboxylic acid ethyl ester | 1.10$^c$ | 539.30 |
| A44 | 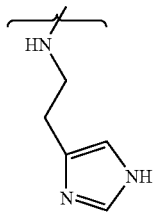 | 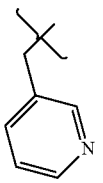 | 2-{4-[2-(1H-Imidazol-4-yl)-ethylamino]-7-pyridin-3-ylmethyl-5,6-dihydro-pyrrolo[2,3-d]pyrimidin-2-ylamino}-4-methyl-thiazole-5-carboxylic acid ethyl ester | 1.11$^c$ | 506.26 |

TABLE A-continued

| Ex. | Z | R⁵ | Name | HPLC Retention (min) | MS Reported |
|---|---|---|---|---|---|
| A45 |  | 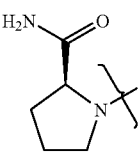 | 2-[4-{(S)-2-Carbamoyl-pyrrolidin-1-yl}-7-pyridin-3-ylmethyl-5,6-dihydro-pyrrolo[2,3-d]pyrimidin-2-ylamino]-4-methyl-thiazole-5-carboxylic acid ethyl ester | 1.19$^c$ | 509.22 |
| A46 |  | 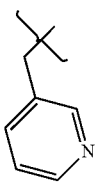 | 2-[4-(3-Hydroxy-pyrrolidin-1-yl)-7-pyridin-3-ylmethyl-5,6-dihydro-pyrrolo[2,3-d]pyrimidin-2-ylamino]-4-methyl-thiazole-5-carboxylic acid ethyl ester | 1.16$^c$ | 482.25 |
| A47 |  | 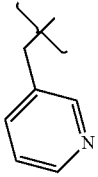 | 4-Methyl-2-(4-morpholin-4-yl-7-pyridin-3-ylmethyl-5,6-dihydro-pyrrolo[2,3-d]pyrimidin-2-ylamino)-thiazole-5-carboxylic acid ethyl ester | 1.32$^c$ | 482.23 |
| A48 |  | 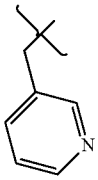 | 4-Methyl-2-{4-[methyl-(1-methyl-piperidin-4-yl)-amino]-7-pyridin-3-ylmethyl-5,6-dihydro-pyrrolo[2,3-d]pyrimidin-2-ylamino}-thiazole-5-carboxylic acid ethyl ester | 1.14$^c$ | 523.31 |
| A49 |  | 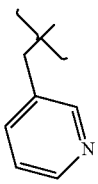 | 2-[4-(3-Diethylcarbamoyl-piperidin-1-yl)-7-pyridin-3-ylmethyl-5,6-dihydro-pyrrolo[2,3-d]pyrimidin-2-ylamino]-4-methyl-thiazole-5-carboxylic acid ethyl ester | 1.63$^c$ | 577.27 |
| A50 |  | 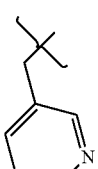 | 2-{4-[4-(2-Hydroxy-ethyl)-piperidin-1-yl]-7-pyridin-3-ylmethyl-5,6-dihydro-pyrrolo[2,3-d]pyrimidin-2-ylamino}-4-methyl-thiazole-5-carboxylic acid ethyl ester | 1.35$^c$ | 524.26 |

TABLE A-continued

| Ex. | Z | R⁵ | Name | HPLC Retention (min) | MS Reported |
|---|---|---|---|---|---|
| A51 | 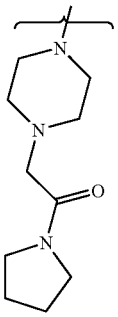 | 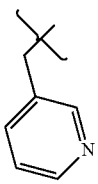 | 4-Methyl-2-{4-[4-(2-oxo-2-pyrrolidin-1-yl-ethyl)-piperazin-1-yl]-7-pyridin-3-ylmethyl-5,6-dihydro-pyrrolo[2,3-d]pyrimidin-2-ylamino}-thiazole-5-carboxylic acid ethyl ester | 1.18[c] | 592.30 |
| A52 | 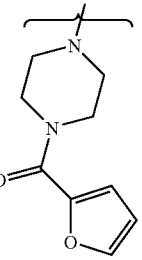 | 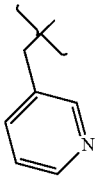 | 2-{4-[4-(Furan-2-carbonyl)-piperazin-1-yl]-7-pyridin-3-ylmethyl-5,6-dihydro-pyrrolo[2,3-d]pyrimidin-2-ylamino}-4-methyl-thiazole-5-carboxylic acid ethyl ester | 1.48[c] | 575.25 |
| A53 | 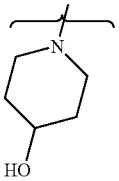 | 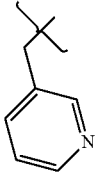 | 2-[4-(4-Hydroxy-piperidin-1-yl)-7-pyridin-3-ylmethyl-5,6-dihydro-pyrrolo[2,3-d]pyrimidin-2-ylamino]-4-methyl-thiazole-5-carboxylic acid ethyl ester | 1.23[c] | 496.26 |
| A54 | 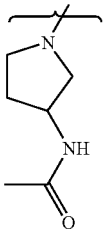 | 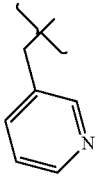 | 2-[4-(3-Acetylamino-pyrrolidin-1-yl)-7-pyridin-3-ylmethyl-5,6-dihydro-pyrrolo[2,3-d]pyrimidin-2-ylamino]-4-methyl-thiazole-5-carboxylic acid ethyl ester | 1.17[c] | 523.28 |
| A55 | 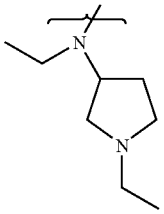 | 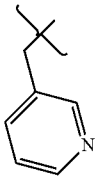 | 2-{4-[Ethyl-(1-ethyl-pyrrolidin-3-yl)-amino]-7-pyridin-3-ylmethyl-5,6-dihydro-pyrrolo[2,3-d]pyrimidin-2-ylamino}-4-methyl-thiazole-5-carboxylic acid ethyl ester | 1.09[c] | 537.31 |
| A56 |  | 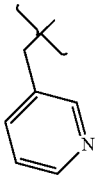 | 2-[4-(4-Carbamoyl-piperidin-1-yl)-7-pyridin-3-ylmethyl-5,6-dihydro-pyrrolo[2,3-d]pyrimidin-2-ylamino]-4-methyl-thiazole-5-carboxylic acid ethyl ester | 1.18[c] | 523.25 |

TABLE A-continued

| Ex. | Z | R⁵ | Name | HPLC Retention (min) | MS Reported |
|---|---|---|---|---|---|
| A57 | 4-ethoxycarbonyl-piperidin-1-yl | pyridin-3-ylmethyl | 4-Methyl-2-[4-(4-carboxyethyl-piperidin-1-yl)-7-pyridin-3-ylmethyl-5,6-dihydro-pyrrolo[2,3-d]pyrimidin-2-ylamino]-thiazole-5-carboxylic acid ethyl ester | 1.54$^c$ | 552.28 |
| A58 | 4-acetyl-piperazin-1-yl | pyridin-3-ylmethyl | 2-[4-(4-Acetyl-piperazin-1-yl)-7-pyridin-3-ylmethyl-5,6-dihydro-pyrrolo[2,3-d]pyrimidin-2-ylamino]-4-methyl-thiazole-5-carboxylic acid ethyl ester | 1.28$^c$ | 523.27 |
| A59 | 3-oxo-piperazin-1-yl | 2-benzyloxy-ethyl | 2-[7-(2-Benzyloxy-ethyl)-4-(3-oxo-piperazin-1-yl)-5,6-dihydro-pyrrolo[2,3-d]pyrimidin-2-ylamino]-4-methyl-thiazole-5-carboxylic acid ethyl ester | 3.39$^b$ | 538.22 |
| A60 | 3-oxo-piperazin-1-yl | 2-hydroxy-ethyl | 2-[7-(2-Hydroxy-ethyl)-4-(3-oxo-piperazin-1-yl)-5,6-dihydro-pyrrolo[2,3-d]pyrimidin-2-ylamino]-4-methyl-thiazole-5-carboxylic acid ethyl ester | 2.44$^b$ | 448.06 |
| A61 | 4-hydroxy-piperidin-1-yl | 4-(1H-tetrazol-5-yl)-benzyl | 2-{4-(4-Hydroxy-piperidin-1-yl)-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester | 1.50$^c$ | 563.27 |

TABLE A-continued

| Ex. | Z | R⁵ | Name | HPLC Retention (min) | MS Reported |
|---|---|---|---|---|---|
| A62 | 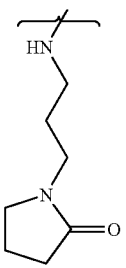 | 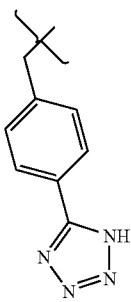 | 4-Methyl-2-{4-[3-(2-oxo-pyrrolidin-1-yl)-propylamino]-7-[4-(1H-tetrazol-5-yl)-benzyl]-5,6-dihydro-pyrrolo[2,3-d]pyrimidin-2-ylamino}-thiazole-5-carboxylic acid ethyl ester | 1.54$^c$ | 604.33 |
| A63 | 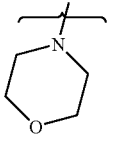 | 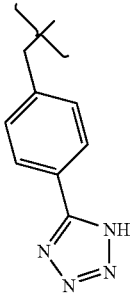 | 4-Methyl-2-{4-morpholin-4-yl-7-[4-(1H-tetrazol-5-yl)-benzyl]-5,6-dihydro-pyrrolo[2,3-d]pyrimidin-2-ylamino}-thiazole-5-carboxylic acid ethyl ester | 1.48$^c$ | 549.32 |
| A64 | 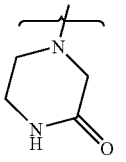 | 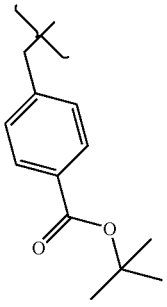 | 2-[7-(4-tert-Butoxycarbonyl-benzyl)-4-(3-oxo-piperazin-1-yl)-5,6-dihydro-pyrrolo[2,3-d]pyrimidin-2-ylamino]-4-methyl-thiazole-5-carboxylic acid ethyl ester | 3.95$^b$ | 594.07 |
| A65 | 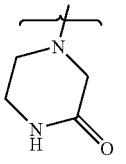 | 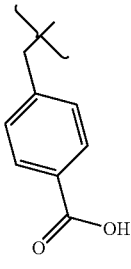 | 2-[7-(4-Carboxy-benzyl)-4-(3-oxo-piperazin-1-yl)-5,6-dihydro-pyrrolo[2,3-d]pyrimidin-2-ylamino]-4-methyl-thiazole-5-carboxylic acid ethyl ester | 3.18$^b$ | 538.21 |
| A66 | 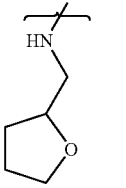 | 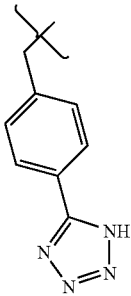 | 4-Methyl-2-{4-[(tetrahydro-furan-2-ylmethyl)-amino]-7-[4-(1H-tetrazol-5-yl)-benzyl]-5,6-dihydro-pyrrolo[2,3-d]pyrimidin-2-ylamino}-thiazole-5-carboxylic acid ethyl ester | 1.64$^c$ | 563.20 |

TABLE A-continued

| Ex. | Z | R⁵ | Name | HPLC Retention (min) | MS Reported |
|---|---|---|---|---|---|
| A67 | HN-cyclopentyl | 4-(1H-tetrazol-5-yl)-benzyl | 2-{4-Cyclopentylamino-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester | 1.76ᶜ | 547.15 |
| A68 | HN-(CH₂)₄-OH | 4-(1H-tetrazol-5-yl)-benzyl | 2-{4-(4-Hydroxy-butylamino)-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester | 1.56ᶜ | 551.62 |
| A69 | HN-CH₂CH₂-(thiophen-2-yl) | 4-(1H-tetrazol-5-yl)-benzyl | 4-Methyl-2-[7-[4-(1H-tetrazol-5-yl)-benzyl]-4-(2-thiophen-2-yl-ethylamino)-5,6-dihydro-pyrrolo[2,3-d]pyrimidin-2-ylamino]-thiazole-5-carboxylic acid ethyl ester | 1.76ᶜ | 589.15 |
| A70 | HN-CH₂CH₂-CH(CH₃)₂ | 4-(1H-tetrazol-5-yl)-benzyl | 4-Methyl-2-{4-(3-methyl-butylamino)-7-[4-(1H-tetrazol-5-yl)-benzyl]-5,6-dihydro-pyrrolo[2,3-d]pyrimidin-2-ylamino}-thiazole-5-carboxylic acid ethyl ester | 1.76ᶜ | 549.23 |
| A71 | HN-CH₂CH₂-O-CH₃ | 4-(1H-tetrazol-5-yl)-benzyl | 2-{4-(2-Ethoxy-ethylamino)-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester | 1.64ᶜ | 551.19 |

TABLE A-continued

| Ex. | Z | R⁵ | Name | HPLC Retention (min) | MS Reported |
|---|---|---|---|---|---|
| A72 | 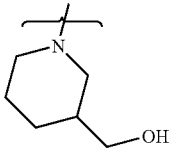 | 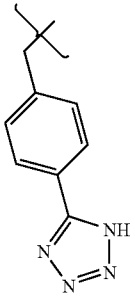 | 2-{4-(3-Hydroxymethyl-piperidin-1-yl)-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester | 1.59$^c$ | 577.22 |

HPLC conditions used to determine retention times::
$^a$Xterra 5 μm C18 column 4.6 × 30 mm, 10-90% aqueous methanol over 2 min containing 0.2% H$_3$PO$_4$, 5 mL/min, monitoring at 220 nm or 254 nm.
$^b$YMC CombiScreen 5 μm C18 column 4.6 × 50 mm, 10-90% aqueous methanol over 4 min containing 0.1% TFA, 4 mL/min, monitoring at 220 nm or 254 nm.
$^c$Phenomenex 5 μm C18 column 4.6 × 30 mm, 10-90% aqueous methanol over 2 min containing 0.2% H$_3$PO$_4$, 5 mL/min, monitoring at 220 nm or 254 nm

Example B1

4-Methyl-2-[4-morpholin-4-yl-6-oxo-7-(3,4,5-trimethoxy-benzyl)-5,6-dihydro-pyrrolo[2,3-d]pyrimidin-2-ylamino]-thiazole-5-carboxylic acid ethyl ester

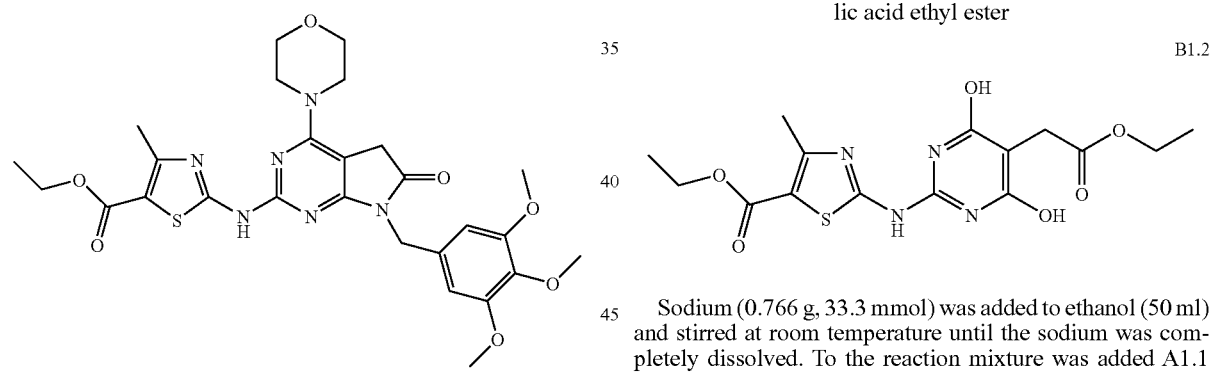

B1.1: 2-Ethoxycarbonyl-succinic acid diethyl ester

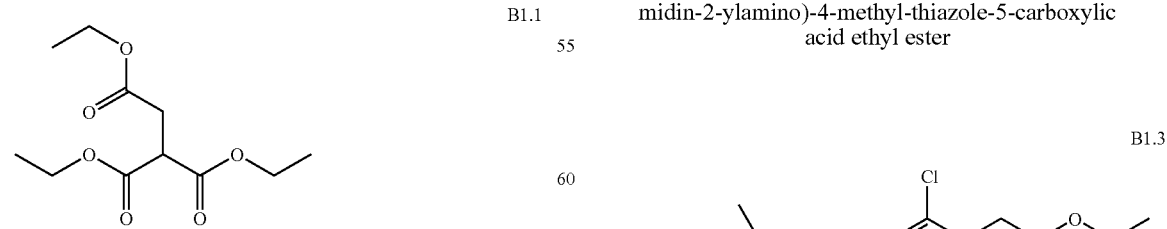

To a suspension of NaH (1.58 g, 62.5 mmol) in THF (100 mL) was added diethylmalonate (10 g, 62.5 mmol), followed by ethyl bromoacetate (8.18 g, 48 mmol) under nitrogen. The reaction mixture was stirred at room temperature for 4 hours and then poured into saturated ammonium chloride solution (200 ml). It was extracted with three potions of ethyl acetate (100 ml). The combined organic phases were washed with brine (100 ml), dried over sodium sulfate and the solvent was removed to yield B1.1 (13.94 g, 91%). $^1$H-NMR (CDCl$_3$) δ: 4.13-4.28 (6H, m), 3.84 (H, t, J=7 Hz), 2.94 (2H, d, J=7 Hz), 1.24-1.33 (9H, m).

B1.2: 2-(5-Ethoxycarbonylmethyl-4,6-dihydroxy-pyrimidin-2-ylamino)-4-methyl-thiazole-5-carboxylic acid ethyl ester Sodium (0.766 g, 33.3 mmol) was added to ethanol (50 ml) and stirred at room temperature until the sodium was completely dissolved. To the reaction mixture was added A1.1 (2.53 g, 11.1 mmol) and B1.1 (3.0 g, 12.2 mmol) which was heated to 100° C. for 7 hrs and then it was cooled to RT. The solid was collected as the desired product B1.2 (3.234 g, 76%). HPLC: 85%, ret. time=3.457 min., LC/MS (M+H)$^+$= 383.03.

B1.3: 2-(4,6-Dichloro-5-ethoxycarbonylmethyl-pyrimidin-2-ylamino)-4-methyl-thiazole-5-carboxylic acid ethyl ester A solution of B1.2 (1.07 g, 0.28 mmol) in POCl₃ (3 ml) was heated to 100° C. for 4 hours and then it was cooled to RT and poured into 50 ml of ice-water. It was neutralized with NaOH/water (1/1) to approximately pH 7. The solid was collected by filtration and then it was added to 10 ml of methanol and stirred about 10 minutes. The solid was collected to yield the desired product B1.3 (590 mg, 50%). HPLC: 82%, ret. time=3.903 min., LC/MS (M+H)⁺=418.96.

B1.4: 4-Methyl-2-[4-morpholin-4-yl-6-oxo-7-(3,4,5-trimethoxy-benzyl)-5,6-dihydro-pyrrolo[2,3-d]pyrimidin-2-ylamino]-thiazole-5-carboxylic acid ethyl ester A solution of B1.3 (50 mg, 0.12 mmol), 3,4,5-trimethoxybenzylamine (24 mg, 0.12 mmol), and diisopropylethylamine (17 mg, 0.13 mmol) in N-methyl-2-pyrrolidine (0.5 ml) was heated to 100° C. for 25 minutes under microwave irradiation. Morpholine (22.5 mg, 0.258 mmol) was then added and the reaction mixture was heated to 180° C. for 15 minutes under microwave irradiation. Methanol (2 ml) was added and the mixture was stirred at room temperature for 30 minutes. The solid was collected to afford B1 (19 mg, 27%). ¹H-NMR (DMSO) δ: 11.65 (1H, s), 6.66 (2H, s), 4.65 (2H, s), 4.09 (2H, q, JJ=7 Hz), 3.73 (2H, s), 3.55-3.65 (14H, m), 3.50 (3H, s), 2.42 (3H, s), 1.12 (3H, t, J=7 Hz). HPLC: 96%, ret. time=3.810 min., LC/MS (M+H)⁺=585.49.

Example B2-B32

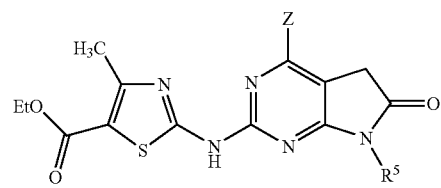

Examples B2 to B32 were prepared in a similar manner to that used for Example B1 utilizing the appropriate amine replacements.

TABLE B1

| Ex. | Z | R⁵ | Name | HPLC Retention[a] (min) | MS Reported |
|---|---|---|---|---|---|
| B2 | piperazin-2-one (HN, O) | 4-sulfamoylbenzyl (H₂N-SO₂-C₆H₄-CH₂-) | 4-Methyl-2-[6-oxo-4-(3-oxo-piperazin-1-yl)-7-(4-sulfamoyl-benzyl)-5,6-dihydro-pyrrolo[2,3-d]pyrimidin-2-ylamino]-thiazole-5-carboxylic acid ethyl ester | 3.01 | 586.98 |
| B3 | piperazin-2-one (HN, O) | 4-methanesulfonylbenzyl (H₃C-SO₂-C₆H₄-CH₂-) | 2-[7-(4-Methanesulfonyl-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester | 3.10 | 586.20 |
| B4 | 4-hydroxypiperidin-1-yl (HO) | 3,4,5-trimethoxybenzyl (MeO, OMe, OMe) | 2[4-(4-Hydroxy-piperidin-1-yl)-6-oxo-7-(3,4,5-trimethoxy-benzyl)-5,6-dihydro-pyrrolo[2,3-d]pyrimidin-2-ylamino]-4-methyl-thiazole-5-carboxylic acid ethyl ester | 3.72 | 599.41 |
| B5 | piperazin-2-one (HN, O) | 3,4,5-trimethoxybenzyl (MeO, OMe, OMe) | 4-Methyl-2-[6-oxo-4-(3-oxo-piperazin-1-yl)-7-(3,4,5-trimethoxy-benzyl)-5,6-dihydro-pyrrolo[2,3-d]pyrimidin-2-ylamino]-thiazole-5-carboxylic acid ethyl ester | 3.52 | 598.38 |

TABLE B1-continued

| Ex. | Z | R⁵ | Name | HPLC Retention[a] (min) | MS Reported |
|---|---|---|---|---|---|
| B6 | 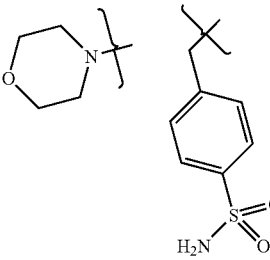 | 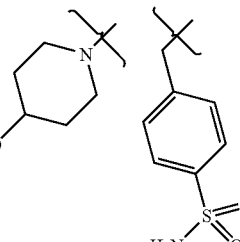 | 4-Methyl-2-[4-morpholin-4-yl-6-oxo-7-(4-sulfamoyl-benzyl)-5,6-dihydro-pyrrolo[2,3-d]pyrimidin-2-ylamino]-thiazole-5-carboxylic acid ethyl ester | 3.32 | 574.38 |
| B7 | 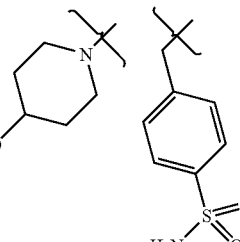 | 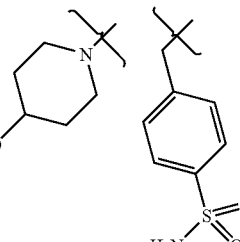 | 2-[4-(4-Hydroxy-piperidin-1-yl)-6-oxo-7-(4-sulfamoyl-benzyl)-5,6-dihydro-pyrrolo[2,3-d]pyrimidin-2-ylamino]-4-methyl-thiazole-5-carboxylic acid ethyl ester | 3.21 | 588.36 |
| B8 | 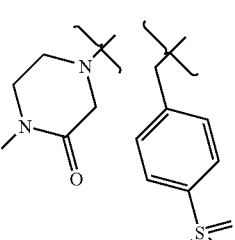 | 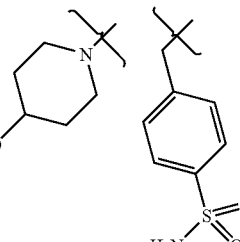 | 4-Methyl-2-[4-(4-methyl-3-oxo-piperazin-1-yl)-6-oxo-7-(4-sulfamoyl-benzyl)-5,6-dihydro-pyrrolo[2,3-d]pyrimidin-2-ylamino]-thiazole-5-carboxylic acid ethyl ester | 3.15 | 601.35 |
| B9 | 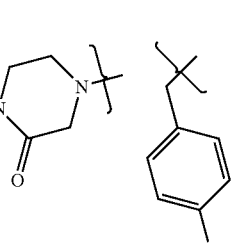 | 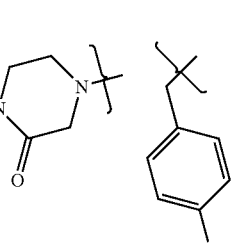 | 4-Methyl-2-[6-oxo-4-(3-oxo-piperazin-1-yl)-7-(4-[1,2,4]triazol-4-yl-benzyl)-5,6-dihydro-pyrrolo [2,3-d]pyrimidin-2-ylamino]-thiazole-5-carboxylic acid ethyl ester | 3.11 | 575.40 |
| B10 | 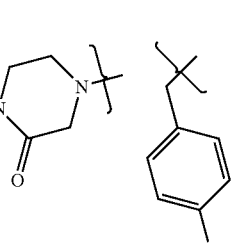 | 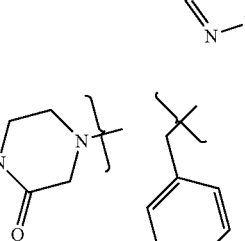 | 2-[7-(4-Imidazol-1-yl-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester | 2.66 | 574.41 |

TABLE B1-continued

| Ex. | Z | R⁵ | Name | HPLC Retention[a] (min) | MS Reported |
|---|---|---|---|---|---|
| B11 | 3-oxo-piperazinyl | 2-(1H-tetrazol-5-yl)benzyl | 4-Methyl-2-{6-oxo-4-(3-oxo-piperazin-1-yl)-7-[2-(1H-tetrazol-5-yl)-benzyl]-5,6-dihydro-pyrrolo[2,3-d]pyrimidin-2-ylamino}-thiazole-5-carboxylic acid ethyl ester | 3.16 | 576.40 |
| B12 | 4-hydroxy-piperidinyl | 2-(1H-tetrazol-5-yl)benzyl | 2-{4-(4-Hydroxy-piperidin-1-yl)-6-oxo-7-[2-(1H-tetrazol-5-yl)-benzyl]-5,6-dihydro-pyrrolo[2,3-d]pyrimidin-2-ylamino}-4-methyl-thiazole-5-carboxylic acid ethyl ester | 3.39 | 577.45 |
| B13 | 3-oxo-piperazinyl | 3-(1H-tetrazol-5-yl)benzyl | 4-Methyl-2-{6-oxo-4-(3-oxo-piperazin-1-yl)-7-[3-(1H-tetrazol-5-yl)-benzyl]-5,6-dihydro-pyrrolo[2,3-d]pyrimidin-2-ylamino}-thiazole-5-carboxylic acid ethyl ester | 3.34 | 576.43 |
| B14 | 3-oxo-piperazinyl | pyridin-3-ylmethyl | 4-Methyl-2-[6-oxo-4-(3-oxo-piperazin-1-yl)-7-pyridin-3-ylmethyl-5,6-dihydro-pyrrolo[2,3-d]pyrimidin-2-ylamino]-thiazole-5-carboxylic acid ethyl ester | 2.47 | 509.43 |
| B15 | 4-hydroxy-piperidinyl | 3-(1H-tetrazol-5-yl)benzyl | 2-{4-(4-Hydroxy-piperidin-1-yl)-6-oxo-7-[3-(1H-tetrazol-5-yl)-benzyl]-5,6-dihydro-pyrrolo[2,3-d]pyrimidin-2-ylamino}-4-methyl-thiazole-5-carboxylic acid ethyl ester | 3.53 | 577.41 |
| B16 | 3-oxo-piperazinyl | pyridin-2-ylmethyl | 4-Methyl-2-[6-oxo-4-(3-oxo-piperazin-1-yl)-7-pyridin-2-ylmethyl-5,6-dihydro-pyrrolo[2,3-d]pyrimidin-2-ylamino]-thiazole-5-carboxylic acid ethyl ester | 2.83 | 509.43 |
| B17 | 4-hydroxy-piperidinyl | pyridin-3-ylmethyl | 2-[4-(4-Hydroxy-piperidin-1-yl)-6-oxo-7-pyridin-3-ylmethyl-5,6-dihydro-pyrrolo[2,3-d]pyrimidin-2-ylamino]-4-methyl-thiazole-5-carboxylic acid ethyl ester | 2.76 | 510.26 |

TABLE B1-continued

| Ex. | Z | R⁵ | Name | HPLC Retention[a] (min) | MS Reported |
|---|---|---|---|---|---|
| B18 | 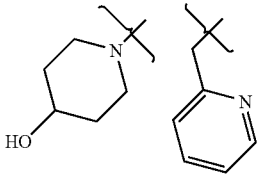 | 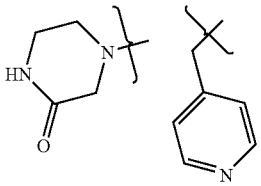 | 2-[4-(4-Hydroxy-piperidin-1-yl)-6-oxo-7-pyridin-2-ylmethyl-5,6-dihydro-pyrrolo[2,3-d]pyrimidin-2-ylamino]-4-methyl-thiazole-5-carboxylic acid ethyl ester | 3.01 | 510.24 |
| B19 | 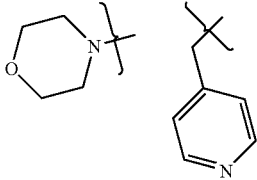 | 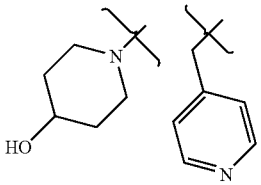 | 4-Methyl-2-[6-oxo-4-(3-oxo-piperazin-1-yl)-7-pyridin-4-ylmethyl-5,6-dihydro-pyrrolo[2,3-d]pyrimidin-2-ylamino]-thiazole-5-carboxylic acid ethyl ester | 2.34 | 509.37 |
| B20 | 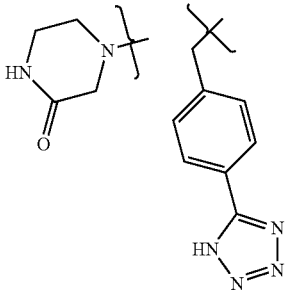 | 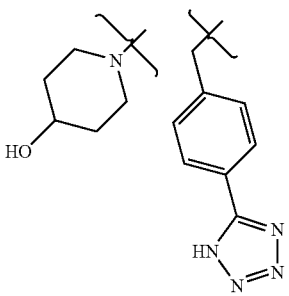 | 4-Methyl-2-(4-morpholin-4-yl-6-oxo-7-pyridin-4-ylmethyl-5,6-dihydro-pyrrolo[2,3-d]pyrimidin-2-ylamino)-thiazole-5-carboxylic acid ethyl ester | 2.69 | 496.38 |
| B21 | | | 2-[4-(4-Hydroxy-piperidin-1-yl)-6-oxo-7-pyridin-4-ylmethyl-5,6-dihydro-pyrrolo[2,3-d]pyrimidin-2-ylamino]-4-methyl-thiazole-5-carboxylic acid ethyl ester | 2.63 | 510.27 |
| B22 | | | 4-Methyl-2-{6-oxo-4-(3-oxo-piperazin-1-yl)-7-[4-(1H-tetrazol-5-yl)-benzyl]-5,6-dihydro-pyrrolo[2,3-d]pyrimidin-2-ylamino}-thiazole-5-carboxylic acid ethyl ester | 3.30 | 576.16 |
| B23 | | | 2-{4-(4-Hydroxy-piperidin-1-yl)-6-oxo-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester | 3.47 | 577.19 |

TABLE B1-continued

| Ex. | Z | R⁵ | Name | HPLC Retention$^a$ (min) | MS Reported |
|---|---|---|---|---|---|
| B24 | morpholine attached via N | 4-(1H-tetrazol-5-yl)benzyl | 4-Methyl-2-{4-morpholin-4-yl-6-oxo-7-[4-(1H-tetrazol-5-yl)-benzyl]-5,6-dihydro-pyrrolo[2,3-d]pyrimidin-2-ylamino}-thiazole-5-carboxylic acid ethyl ester | 3.62 | 563.26 |
| B25 | 4-hydroxypiperidin-1-yl | 4-cyanobenzyl | 2-[7-(4-Cyano-benzyl)-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester | 3.55 | 534.13 |
| B26 | 4-hydroxypiperidin-1-yl | 4-methylbenzyl | 2-[4-(4-Hydroxy-piperidin-1-yl)-7-(4-methyl-benzyl)-6-oxo-5,6-dihydro-pyrrolo[2,3-d]pyrimidin-2-ylamino]-4-methyl-thiazole-5-carboxylic acid ethyl ester | 3.95 | 523.15 |
| B27 | 4-hydroxypiperidin-1-yl | benzyl | 2-[7-Benzyl-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester | 3.78 | 509.14 |
| B28 | 4-hydroxypiperidin-1-yl | 3-fluorobenzyl | 2-[7-(3-Fluoro-benzyl)-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester | 3.82 | 527.17 |

TABLE B1-continued

| Ex. | Z | R⁵ | Name | HPLC Retention[a] (min) | MS Reported |
|---|---|---|---|---|---|
| B29 | 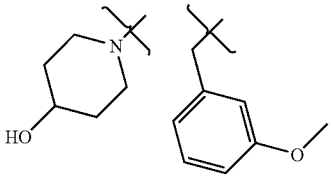 | | 2-[4-(4-Hydroxy-piperidin-1-yl)-7-(3-methoxy-benzyl)-6-oxo-5,6-dihydro-pyrrolo[2,3-d]pyrimidin-2-ylamino]-4-methyl-thiazole-5-carboxylic acid ethyl ester | 3.80 | 539.17 |
| B30 | 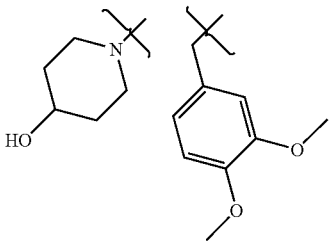 | | 2-[7-(3,4-Dimethoxy-benzyl)-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester | 3.61 | 569.16 |
| B31 | 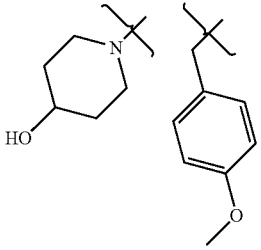 | | 2-[4-(4-Hydroxy-piperidin-1-yl)-7-(4-methoxy-benzyl)-6-oxo-5,6-dihydro-pyrrolo[2,3-d]pyrimidin-2-ylamino]-4-methyl-thiazole-5-carboxylic acid ethyl ester | 3.76 | 539.17 |
| B32 | 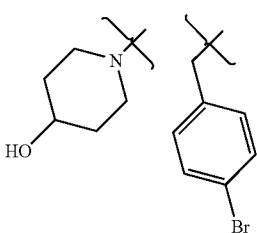 | | 2-[7-(4-Bromo-benzyl)-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester | 4.10 | 587.02 |

HPLC conditions used to determined retention times:

[a]YMC CombiScreen 5 μm C18 column 4.6 × 50 mm, 10-90% aqueous methanol over 4 min containing 0.1% TFA, 4 mL/min, monitoring at 220 nm or 254 nm

Example B33

2-[4-(4-Hydroxy-piperidin-1-yl)-6-oxo-7-(4-thiophen-3-yl-benzyl)-5,6-dihydro-pyrrolo[2,3-d]pyrimidin-2-ylamino]-4-methyl-thiazole-5-carboxylic acid ethyl ester

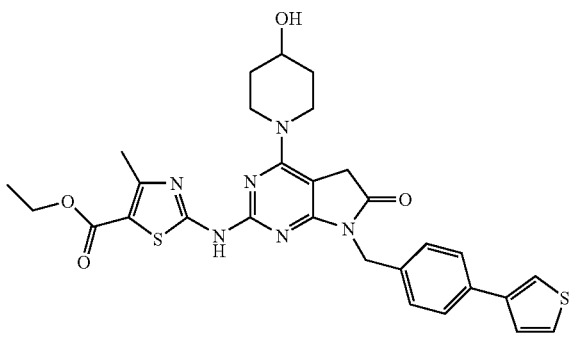

B33

A degassed solution of 3-thiopheneboronic acid (4.4 mg, 0.034 mmol) in 0.4 M sodium carbonate solution (0.5 ml) was added dropwise to the degassed suspension of B32 (20 mg, 0.034 mmol) and tetrakis(triphenylphosphine)palladium(0) (20 mg, 0.017 mmol) in acetonitrile (0.5 ml) at 90° C. under nitrogen. The reaction mixture was heated at 90° C. for 30 minutes. The hot suspension was filtered to remove the catalyst and the filtrate was concentrated to afford the crude product which was purified by preparative TLC (silica, 2:1 EtOAc:hexanes) to yield B33 (6.2 mg, 31%). $^1$H-NMR (DMSO) δ: 11.68 (1H, s), 7.82-7.86 (1H, m), 7.61-7.69 (3H, M), 7.51-7.54 (1H, m), 7.43 (2H, d, J=8 Hz), 4.86 (2H, s), 4.22 (2H, q, JJ=7 Hz), 4.08-4.18 (2H, m), 3.84 (2H, s), 3.74-3.81 (1H, m), 3.33-3.35 (2H, m, merge with water), 2.51 (3H, s, merge with DMSO), 1.78-1.87 (2H, m), 1.36-1.48 (2H, m), 1.27 (3H, t, J=7 Hz). HPLC: >95%, ret. time=4.120 min., LC/MS (M+H)$^+$=591.11.

Example B34-B36

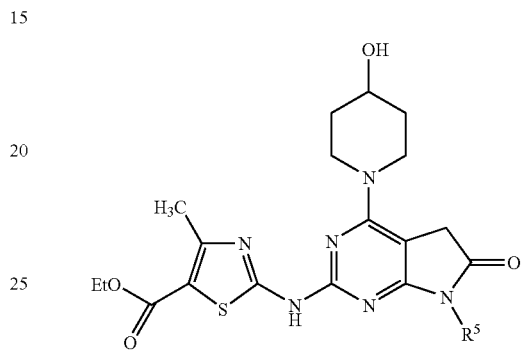

Examples B34 and B35 were prepared in a similar manner to that used for Example B33 utilizing the appropriate heteroarylboronic acid replacement. Example B36 was isolated as a side product during the preparation of Example B35.

TABLE B2

| Ex. | R$^5$ | Name | HPLC Retention$^a$ (min) | MS Reported |
|---|---|---|---|---|
| B34 | (3,5-dimethylisoxazol-4-yl-benzyl group) | 2-[7-[4-(3,5-Dimethyl-isoxazol-4-yl)-benzyl]-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester | 3.81 | 604.14 |
| B35 | (1-Boc-pyrrol-2-yl-benzyl group) | 2-[7-[4-(1-tert-Butoxycarbonyl-1H-pyrrol-2-yl)-benzyl]-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester | 4.25 | 674.14 |

TABLE B2-continued

| Ex. | R⁵ | Name | HPLC Retention[a] (min) | MS Reported |
|---|---|---|---|---|
| B36 | 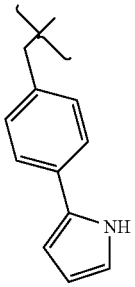 | 2-{4-(4-Hydroxy-piperidin-1-yl)-6-oxo-7-[4-(1H-pyrrol-2-yl)-benzyl]-5,6-dihydro-pyrrolo[2,3-d]pyrimidin-2-ylamino}-4-methyl-thiazole-5-carboxylic acid ethyl ester | 3.80 | 574.16 |

HPLC conditions used to determined retention times:
[a]YMC CombiScreen 5 μm C18 column 4.6 × 50 mm, 10-90% aqueous methanol over 4 min containing 0.1% TFA, 4 mL/min, monitoring at 220 nm or 254 nm

Example B37

2-[7-(4-Carboxy-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester

B37

A solution of B1.3 (223 mg, 053 mmol), t-butyl(4-aminomethyl)benzoate (110 mg, 0.53 mmol), and diisopropylethylamine (108 uL, 0.56 mmol) in N-methyl-2-pyrrolidine (2 ml) was heated to 100° C. for 20 minutes under microwave irradiation. Piperazin-2-one (113 mg, 1.12 mmol) was then added. The reaction mixture was heated to 180° C. for 10 minutes under microwave irradiation, 10 ml of methanol was added and the mixture stirred for 5 minutes. The solid which was collected was dissolved in dichloromethane (0.5 ml) and TFA (0.5 ml) at 0-5° C. The reaction mixture was warmed to RT, stirred for 30 minutes and concentrated. Methanol (2 ml) was added and the mixture stirred for 10 minutes. The solid was collected to afford B37 (97.3 mg, 73%). ¹H-NMR (DMSO) δ: 11.84 (1H, s), 8.28 (1H, s), 7.99 (2H, d, J=8 Hz), 7.57 (2H, d, J=8 Hz), 5.04 (2H, s), 4.42 (2H, s), 4.32 (2H, q, J=7 Hz), 4.07 (2H, s), 3.96-4.02 (2H, m), 3.55-3.75 (2H, m), 2.61 (3H, s, merge with DMSO), 1.38 (3H, t, J=7 Hz). HPLC: 89%, ret. time=3.31 min., LC/MS (M+H)⁺=552.05.

Example B38

2-[7-(4-Dimethylcarbamoyl-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester

B38

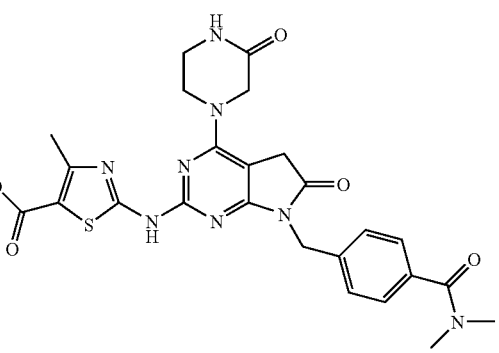

A solution of B37 (15 mg, 0.027 mmol) dimethylamine hydrochloride (2.66 mg, 0.0326 mmol) and diisopropylethylamine (11.5 mg, 0.114 mmol) in DMF (1 ml) was treated with bis(oxo-3-oxazolidinyl) phosphinic chloride (21 mg, 0.081 mmol) and the reaction mixture was stirred at RT for 1 h. The reaction mixture was purified by preparative HPLC to afford B38 (7.3 mg, 47%). ¹H-NMR (CDCl₃) δ: 7.41 (2H, d, J=8 Hz), 7.18 (2H, d, J=8 Hz), 6.47 (1H, s), 4.16-4.25 (4H, m), 3.83-3.90 (2H, m), 3.56 (2H, s), 3.35-3.41 (2H, m), 2.92

(3H, s), 2.78 (3H, s), 2.52 (3H, s), 1.22 (3H, t, J=7 Hz). HPLC: >90%, ret. time=3.160 min., LC/MS (M+H)+=579.15.

Example B39-B43

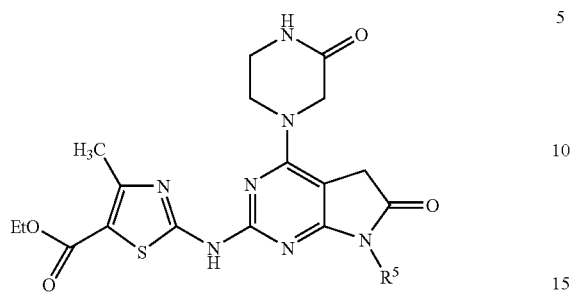

Examples B39 to B43 were prepared in a similar manner to that used for Example B38 utilizing the appropriate amine replacement.

TABLE B3

| Ex. | R[5] | Name | HPLC Retention[a] (min) | MS Reported |
|---|---|---|---|---|
| B39 | | 2-[7-[4-(4-Hydroxy-piperidine-1-carbonyl)-benzyl]-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester | 3.12 | 635.12 |
| B40 | | 4-Methyl-2-[7-[4-(morpholine-4-carbonyl)-benzyl]-6-oxo-4-(3-oxo-piperazin-1-yl)-5,6-dihydro-pyrrolo[2,3-d]pyrimidin-2-ylamino]-thiazole-5-carboxylic acid ethyl ester | 3.15 | 621.12 |
| B41 | | 2-[7-(4-Isobutylcarbamoyl-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester | 3.45 | 607.19 |

TABLE B3-continued

| Ex. | R⁵ | Name | HPLC Retention[a] (min) | MS Reported |
|---|---|---|---|---|
| B42 |  | 2-[7-[4-(3-Hydroxy-pyrrolidine-1-carbonyl)-benzyl]-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester | 3.05 | 621.13 |
| B43 |  | 2-[7-{4-[(2-Hydroxy-ethyl)-methyl-carbamoyl]-benzyl}-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester | 3.07 | 609.19 |

HPLC conditions used to determine retention times:
[a]YMC CombiScreen 5 μm C18 column 4.6 × 50 mm, 10-90% aqueous methanol over 4 min containing 0.1% TFA, 4 mL/min, monitoring at 220 nm or 254 nm Example C1

2-[8-(4-Methanesulfonyl-benzyl)-4-(1-tert-butoxy-carbonyl-piperazin-4-yl)-5,6,7,8-tetrahydro-pyrido[2,3-d]pyrimidin-2-ylamino]-4-methyl-thiazole-5-carboxylic acid ethyl ester

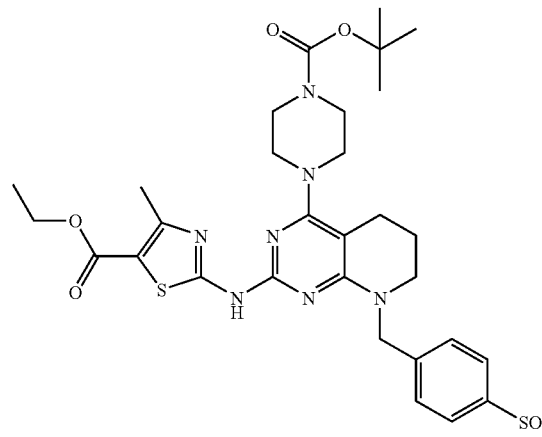

C1.1: 4-(2-Chloro-pyrido[2,3-d]pyrimidin-4-yl)-piperazine-1-carboxylic acid tert-butyl ester

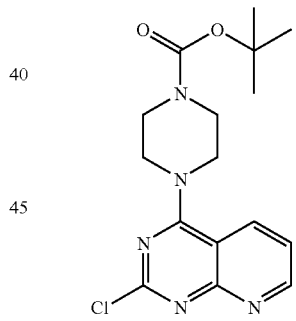

C1.1

A mixture of 2,4-dichloro-pyrido[2,3-d]pyrimidine (150 mg, 0.75 mmol, 1 eq) [prepared from 2-aminonicotinic acid by the methods of Robins et al. (*J. Am. Chem. Soc.* 1955, 77, 1045.) and Oakes et al. (*J. Chem. Soc.* 1956, 1045.)], N-t-butoxycarbonyl piperazine (147 mg, 0.787 mmol, 1.05 eq) and Hunig's base (0.39 mL, 2.25 mmol, 3 eq) in ethanol (2.5 mL) was stirred at rt for 17 hr. The white solid was collected by filtration, washed with water and cold ethanol, and dried to afford C1.1 (105 mg, 40% yield). LC/MS: 350.41 [M+H]⁺; HPLC: >95% at 1.44 min (Xterra 5 μm C18 column 4.6×30 mm, 10-90% aqueous methanol over 2 min containing 0.2% phosphoric acid, 5 mL/min, monitoring at 254 nm).

C1.2: C4-(2-Chloro-5,6,7,8-tetrahydro-pyrido[2,3-d]pyrimidin-4-yl)-piperazine-1-carboxylic acid tert-butyl ester

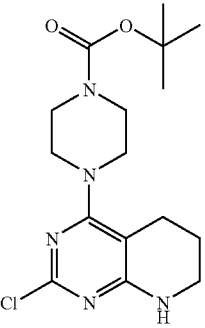

C1.2

A mixture of C1.1 (41 mg, 0.117 mmol, 1 eq), PtO$_2$ (2.7 mg, 0.0117 mmol, 0.1 eq) and ethanol (1 mL) was stirred under a H$_2$ atmosphere (1 atm) for 4.5 h. The mixture was filtered through celite and the filtrate was concentrated to afford C1.2 (41 mg, quant.) as a white solid. LC/MS: 354.42 [M+H]$^+$; HPLC: 96% at 3.43 min (Phenomenex Luna 5 μm C18 column 4.6×50 mm, 10-90% aqueous methanol over 4 min containing 0.2% phosphoric acid, 4 mL/min, monitoring at 254 nm). $^1$H NMR (400 MHz, CD$_3$OD): δ 3.41 (m, 4H), 3.24 (m, 2H), 3.16 (m, 4H), 2.46 (m, 2H), 1.70 (m, 2H), 1.37 (s, 9H).

C1.3: 2-[8-(4-Methanesulfonyl-benzyl)-4-(1-tert-butoxycarbonyl-piperazin-4-yl)-5,6,7,8-tetrahydro-pyrido[2,3-d]pyrimidin-2-ylamino]-4-methyl-thiazole-5-carboxylic acid ethyl ester A solution of C1.2 (40 mg, 0.113 mmol, 1 eq) in DMF (1 mL) at 0° C. was treated with NaH (60% in mineral oil, 5 mg, 0.124 mmol, 1.1 eq). After stirring at 0° C. for 10 min, 4-methylsulfonylbenzyl chloride (25 mg, 0.124 mmol, 1.1 eq) was added, the reaction mixture was warmed to rt, stirred for 1.5 h and then poured onto ice. The solid was collected by filtration, washed with water and dried to afford (42 mg, 71% yield) a light yellow solid. HPLC: >95% at 1.81 min (Xterra 5 μm C18 column 4.6×30 mm, 10-90% aqueous methanol over 2 min containing 0.2% phosphoric acid, 5 mL/min, monitoring at 254 nm).

To a mixture of this product (40 mg, 0.0766 mmol, 1 eq) and ethyl 2-amino-4-methylthiazole-5-carboxylate (28.5 mg, 0.153 mmol, 2 eq) in N,N-dimethylacetamide (0.8 mL) in a 2-dram vial was added tris(dibenzylideneacetone)dipalladium(0) (7 mg, 0.0077 mmol, 0.1 eq), 2-(di-t-butylphosphino)biphenyl (6.9 mg, 0.023 mmol, 0.3 eq) and potassium phosphate (33 mg, 0.153 mmol, 2 eq). The vial was purged with N$_2$, sealed and heated in a 105° C. oil bath for 2.5 h. The reaction mixture was cooled to rt, filtered and concentrated in vacuo. Column chromatography (SiO$_2$, 60% ethyl acetate/heptane→ethyl acetate) gave C1 (35 mg, 68% yield) as a yellow solid. LC/MS: 672.44 [M+H]$^+$; HPLC: 96% at 1.87 min (Xterra 5 μm C18 column 4.6×30 mm, 10-90% aqueous methanol over 2 min containing 0.2% phosphoric acid, 5 mL/min, monitoring at 254 nm). $^1$H NMR (500 MHz, DMSO-d$_6$): δ 11.26 (br s, 1H), 7.87 (d, J=8.2 Hz, 2H), 7.57 (d, J=8.2 Hz, 2H), 4.99 (s, 2H), 4.15 (q, J=6.6 Hz, 2H), 3.45 (m, 4H), 3.36 (m, 2H), 3.24 (m, 4H), 3.17 (s, 3H), 2.54 (m, 2H), 2.47 (s, 3H), 1.79 (m, 2H), 1.42 (s, 9H), 1.21 (m, 3H).

Example C2

2-[8-(4-Methanesulfonyl-benzyl)-4-piperazin-1-yl-5,6,7,8-tetrahydro-pyrido[2,3-d]pyrimidin-2-ylamino]-4-methyl-thiazole-5-carboxylic acid ethyl ester

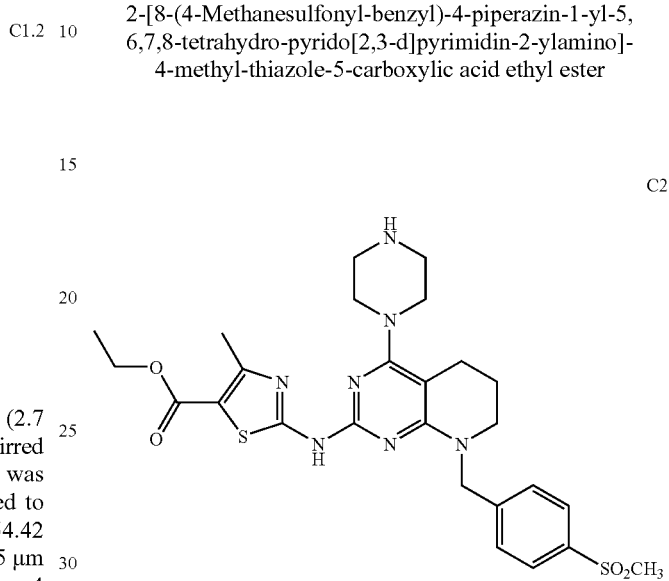

C2

A solution of C1 (17.6 mg, 0.026 mmol, 1 eq) in dichloromethane (1.5 mL) was cooled to 0° C. and trifluoroacetic acid (0.2 mL) was added dropwise. The reaction mixture was stirred at 0° C. for 4.5 h and then ether (ca. 2 mL) was added. The precipitated beige solid was collected by filtration and dried to afford C2 (7.5 mg, 42% yield) as the trifluoroacetic acid salt. LC/MS: 572.44 [M+H]$^+$; HPLC: >95% at 1.24 min (Xterra 5 μm C18 column 4.6×30 mm, 10-90% aqueous methanol over 2 min containing 0.2% phosphoric acid, 5 mL/min, monitoring at 254 nm).

Example C3-C7

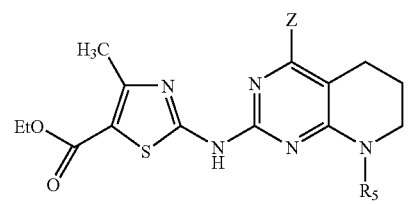

Example C3 was prepared in a similar manner to that used for Example C2 utilizing dimethylamine in place of N-t-butoxycarbonyl piperazine in step C1.1. Examples C4 to C7 were prepared in a similar manner to that used for Example C2 utilizing the appropriate replacement for 4-methylsulfonylbenzyl chloride in step C1.3.

TABLE C1

| Ex. | Z | R⁵ | Name | HPLC Retention (min)ᵃ | MS Reported |
|---|---|---|---|---|---|
| C3 | (H₃C)(H₃C)N– | 4-(methanesulfonyl)benzyl | 2-[4-Dimethylamino-8-(4-methanesulfonyl-benzyl)-5,6,7,8-tetrahydro-pyrido[2,3-d]pyrimidin-2-ylamino]-4-methyl-thiazole-5-carboxylic acid ethyl ester | 1.37 | 531.55 |
| C4 | piperazin-1-yl | benzyl | 2-(8-Benzyl-4-piperazin-1-yl-5,6,7,8-tetrahydro-pyrido[2,3-d]pyrimidin-2-ylamino)-4-methyl-thiazole-5-carboxylic acid ethyl ester | 1.55 | 494.35 |
| C5 | piperazin-1-yl | 4-fluorobenzyl | 2-[8-(4-Fluoro-benzyl)-4-piperazin-1-yl-5,6,7,8-tetrahydro-pyrido[2,3-d]pyrimidin-2-ylamino]-4-methyl-thiazole-5-carboxylic acid ethyl ester | 1.57 | 512.27 |
| C6 | piperazin-1-yl | pyridin-3-ylmethyl | 4-Methyl-2-(4-piperazin-1-yl-8-pyridin-3-ylmethyl-5,6,7,8-tetrahydro-pyrido[2,3-d]pyrimidin-2-ylamino)-thiazole-5-carboxylic acid ethyl ester | 0.95 | 495.37 |
| C7 | piperazin-1-yl | 3,4,5-trimethoxybenzyl | 4-Methyl-2-[4-piperazin-1-yl-8-(3,4,5-trimethoxy-benzyl)-5,6,7,8-tetrahydro-pyrido[2,3-d]pyrimidin-2-ylamino]-thiazole-5-carboxylic acid ethyl ester | 1.40 | 584.05 |

HPLC conditions used to determine retention times:

ᵃXterra 5 μm C18 column 4.6 × 30 mm, 10-90% aqueous methanol over 2 min containing 0.2% H₃PO₄, 5 mL/min, monitoring at 220 nm or 254 nm.

Example C8

2-[4-(4-Hydroxy-piperidin-1-yl)-8-(3,4,5-tri-methoxy-benzyl)-5,6,7,8-tetrahydro-pyrido[2,3-d]pyrimidin-2-ylamino]-4-methyl-thiazole-5-carboxylic acid ethyl ester

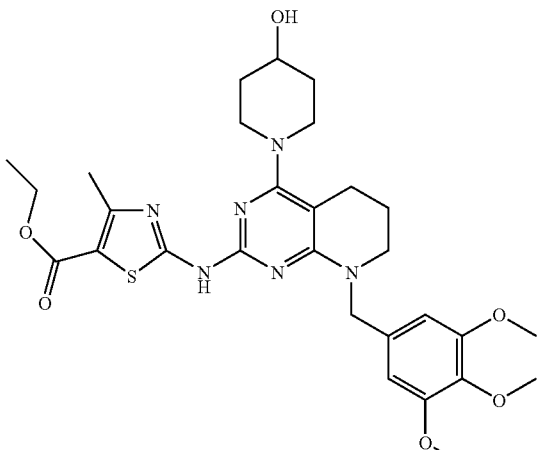

C8.1: 2-But-3-enyl-malonic acid diethyl ester

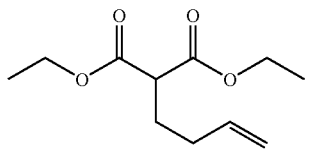

A mixture of sodium hydride (60% in mineral oil, 435 mg, 10.87 mmol, 1.1 eq) in DMF (20 mL) was treated dropwise with diethyl malonate (1.5 mL, 9.88 mmol, 1.0 eq). The reaction mixture was then cooled to 0° C. and 4-bromo-1-butene (1.0 mL, 9.88 mmol, 1 eq) was added dropwise. The reaction mixture was warmed to rt, stirred for 3 days and then partitioned between ether and water. The layers were separated, the aqueous layer was extracted with ether (2×50 mL) and the combined organic phases were washed with water (2×) and brine, dried over MgSO$_4$ and concentrated. Column chromatography (SiO$_2$, 5% ether/heptane) gave C8.1 (1.51 g, 71% yield) as a colorless oil. $^1$H NMR (400 MHz, DMSO-d$_6$): δ 5.77 (m, 1H), 5.00 (m, 2H), 4.13 (q, J=7.1 Hz, 4H), 3.43 (t, J=7.4 Hz, 1H), 2.02 (m, 2H), 1.84 (m, 2H), 1.17 (t, J=7.1 Hz, 6H).

C8.2: 2-(5-But-3-enyl-4,6-dioxo-1,4,5,6-tetrahydro-pyrimidin-2-ylamino)-4-methyl-thiazole-5-carboxylic acid ethyl ester

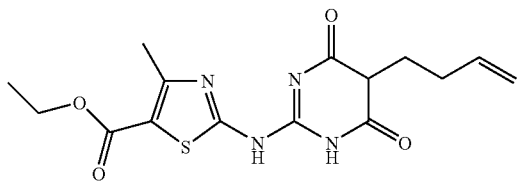

To a solution of NaOEt in EtOH [prepared by dissolving Na (101 mg, 4.38 mmol, 2.5 eq) in 12 mL of absolute ethanol] was added A1.1 (400 mg, 1.75 mmol, 1 eq) and the mixture was stirred at rt for 10 min. A solution of C8.1 (376 mg, 1.75 mmol, 1 eq) in ethanol (5 mL) was added dropwise, the reaction mixture was heated at reflux for 20.5 h and then cooled and poured onto a mixture of ice and 10% aq H$_2$SO$_4$. The solid was collected by filtration, washed with water and dried to afford C8.2 (430 mg, 70% yield) as a white solid. LC/MS: 351.57 [M+H]$^+$; HPLC: >95% at 1.74 min (Xterra 5 μm C18 column 4.6×30 mm, 10-90% aqueous methanol over 2 min containing 0.2% phosphoric acid, 5 mL/min, monitoring at 254 nm).

C8.3: 2-(5-But-3-enyl-4,6-dichloro-pyrimidin-2-ylamino)-4-methyl-thiazole-5-carboxylic acid ethyl ester

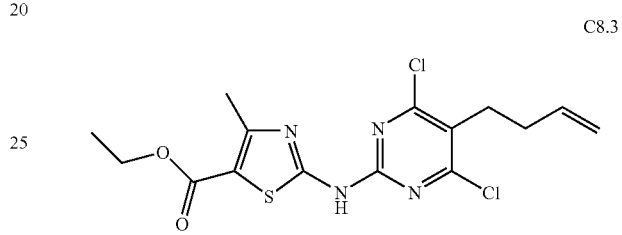

A mixture of C8.2 (430 mg, 1.23 mmol, 1 eq) and POCl$_3$ (4 mL) was heated in a 100° C. oil bath for 28 h. The reaction mixture was poured onto ice, neutralized with 2 N NaOH, and extracted with ethyl acetate. The organic phase was washed with sat. NaHCO$_3$ and brine, dried over MgSO$_4$ and concentrated to afford C8.3 (383 mg, 80% yield) as a beige solid. LC/MS: 387.22 [M+H]$^+$; HPLC: >95% at 2.15 min (Xterra 5 μm C18 column 4.6×30 mm, 10-90% aqueous methanol over 2 min containing 0.2% phosphoric acid, 5 mL/min, monitoring at 254 nm). $^1$H NMR (400 MHz, DMSO-d$_6$): δ 12.65 (br s, 1H), 5.90 (m, 1H), 5.03 (m, 2H), 4.27 (q, J=7.1 Hz, 2 H), 2.85 (m, 2H), 2.54 (s, 3H), 2.31 (m, 2H), 1.29 (t, J=7.1 Hz, 3H).

C8.4: 2-[4,6-Dichloro-5-(3,4-dihydroxy-butyl)-pyrimidin-2-ylamino]-4-methyl-thiazole-5-carboxylic acid ethyl ester

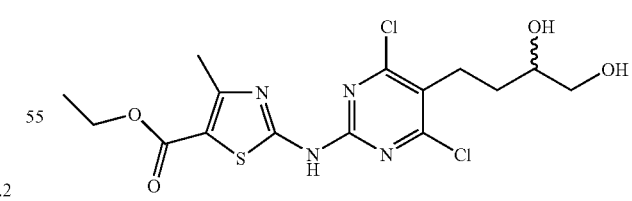

To a mixture of C8.3 (383 mg, 0.988 mmol, 1 eq) and NMO monohydrate (267 mg, 1.976 mmol, 2 eq) in THF/water (9:1, 10 mL) at 0° C. was added a solution of OsO$_4$ in water (4 wt %, 0.61 mL, 0.0988 mmol, 0.1 eq). The reaction mixture was warmed to rt, stirred for 16.5 h and then quenched with a solution of 300 mg of NaHSO$_3$ in 20 mL of water. The off-white solid was collected by filtration, washed with water and ether, and dried to afford C8.4 (280 mg, 67% yield).

LC/MS: 421.42 [M+H]+; HPLC: 96% at 1.66 min (Xterra 5 μm C18 column 4.6×30 mm, 10-90% aqueous methanol over 2 min containing 0.2% phosphoric acid, 5 mL/min, monitoring at 254 nm).

C8.5: 2-[4,6-Dichloro-5-(3-oxo-propyl)-pyrimidin-2-ylamino]-4-methyl-thiazole-5-carboxylic acid ethyl ester

C8.5

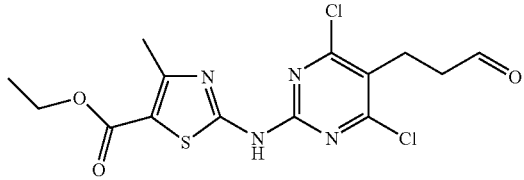

A mixture of C8.4 (30 mg, 0.0712 mmol, 1 eq) in THF/methanol (1:1, 1 mL) at 0° C. was treated with Pb(OAc)$_4$ (35 mg, 0.0783 mmol, 1.1 eq). After 3 h at 0° C., the reaction mixture was diluted with ethyl acetate, washed with water and brine, dried over Na$_2$SO$_4$ and concentrated to afford C8.5 (28 mg, quantitative yield) as a white solid. HPLC: >95% at 1.80 min (Xterra 5 μm C18 column 4.6×30 mm, 10-90% aqueous methanol over 2 min containing 0.2% phosphoric acid, 5 mL/min, monitoring at 254 nm). $^1$H NMR (400 MHz, CDCl$_3$): δ 9.88 (s, 1H), 4.36 (q, J=7.1 Hz, 2H), 3.17 (m, 2H), 2.78 (m, 2H), 2.73 (s, 3H), 1.40 (t, J=7.1 Hz, 3H).

C8.6: 2-[4-Chloro-8-(3,4,5-trimethoxy-benzyl)-5,6,7,8-tetrahydro-pyrido[2,3-d]pyrimidin-2-ylamino]-4-methyl-thiazole-5-carboxylic acid ethyl ester

C8.6

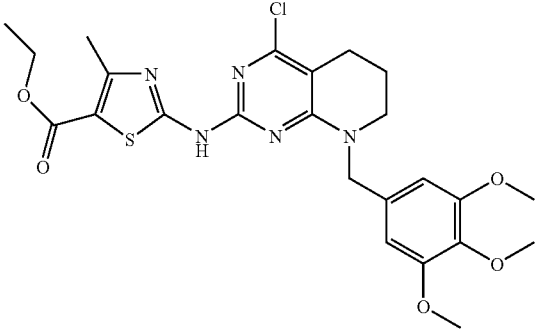

To a solution of C8.5 (500 mg, 1.28 mmol) in THF (14 mL), was added 3,4,5-trimethoxybenzylamine (0.230 mL, 1.35 mmol), Na(OAc)$_3$BH (407 mg, 1.92 mmol) and AcOH (0.073 mL, 1.28 mmol). The reaction was stirred at room temperature for 1 hr, and then quenched with NaHCO$_3$ and extracted with EtOAc. The organic layer was washed with 1N HCl and brine, dried (Na$_2$SO$_4$), filtered and concentrated in vacuo to yield 641 mg (94% yield) of C8.6 as a dark tan solid. MS, (ES), m/e: 535 (MH+). 1H NMR (DMSO-d$_6$): 1.11 (t, 3H, J=7.0 Hz), 1.88 (m, 2H), 2.52 (s, 3H), 2.66 (t, 2H, J=6.0 Hz), 3.40 (t, 2H, J=5.0 Hz), 3.65 (s, 2H), 3.73 (s, 9H), 4.13 (q, 2H, J=7.0 Hz), 6.69 (s, 2H), 11.7 (s, 1H).

C8.7: 2-[4-(4-Hydroxy-piperidin-1-yl)-8-(3,4,5-trimethoxy-benzyl)-5,6,7,8-tetrahydro-pyrido[2,3-d]pyrimidin-2-ylamino]-4-methyl-thiazole-5-carboxylic acid ethyl ester To a solution of C8.6 (500 mg, 0.940 mmol) in n-BuOH (2 mL), was added 4-hydroxypiperidine (208 mg, 2.1 mmol), and Hunig's base (738 mL, 4.1 mmol). The reaction mixture was heated at 200° C. under microwave irradiation for 30 min and then diluted with MeOH and purified by preparative HPLC to afford C8. MS, (ES), m/e: 598.73 (MH+). HPLC: 1.59 min (Phenomenex 5 μm C18 column 4.6×30 mm, 10-90% aqueous methanol over 2 min containing 0.2% phosphoric acid, 5 mL/min, monitoring at 254 nm).

Example C9-C82

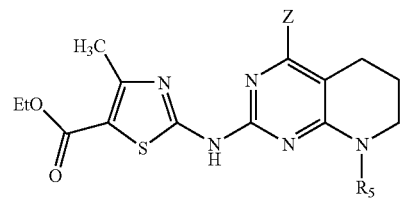

Examples C9 to C82 were prepared in a similar manner to that used for Example C8 utilizing the appropriate amine replacements.

TABLE C2

| Ex. | Z | R$^5$ | Name | HPLC Retention (min) | MS Reported |
|---|---|---|---|---|---|
| C9 | ![piperazine] | ![trimethoxybenzyl] | 4-Methyl-2-[4-(4-methyl-piperazin-1-yl)-8-(3,4,5-trimethoxy-benzyl)-5,6,7,8-tetrahydro-pyrido[2,3-d]pyrimidin-2-ylamino]-thiazole-5-carboxylic acid ethyl ester | 1.38$^a$ | 598.55 |

TABLE C2-continued

| Ex. | Z | R⁵ | Name | HPLC Retention (min) | MS Reported |
|---|---|---|---|---|---|
| C10 | 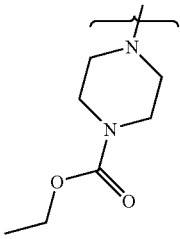 | 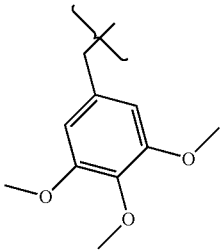 | 2-[4-(1-carboxyethyl-piperazin-4-yl)-8-(3,4,5-trimethoxy-benzyl)-5,6,7,8-tetrahydro-pyrido[2,3-d]pyrimidin-2-ylamino]-4-methyl-thiazole-5-carboxylic acid ethyl ester | 1.77[b] | 655.78 |
| C11 | 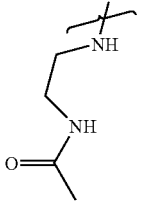 | 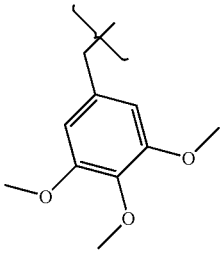 | 2-[4-(2-Acetylamino-ethylamino)-8-(3,4,5-trimethoxy-benzyl)-5,6,7,8-tetrahydro-pyrido[2,3-d]pyrimidin-2-ylamino]-4-methyl-thiazole-5-carboxylic acid ethyl ester | 1.63[b] | 599.71 |
| C12 | 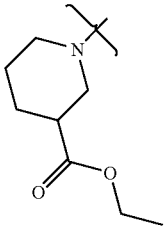 | 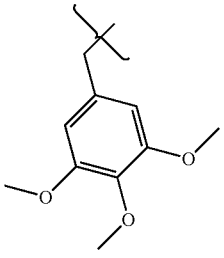 | 2-[4-(3-carboxyethyl-piperidin-1-yl)-8-(3,4,5-trimethoxy-benzyl)-5,6,7,8-tetrahydro-pyrido[2,3-d]pyrimidin-2-ylamino]-4-methyl-thiazole-5-carboxylic acid ethyl ester | 1.85[b] | 654.79 |
| C13 | 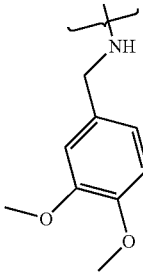 | 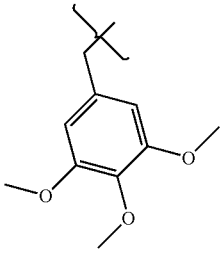 | 4-Methyl-2-[8-(3,4,5-trimethoxy-benzyl)-4-(3,4,5-trimethoxy-benzylamino)-5,6,7,8-tetrahydro-pyrido[2,3-d]pyrimidin-2-ylamino]-thiazole-5-carboyxlic acid ethyl ester | 1.67[a] | 694.81 |
| C14 | 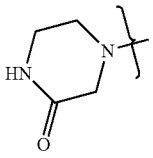 | 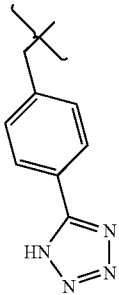 | 4-Methyl-2-{4-(3-oxo-piperazin-1-yl)-8-[4-(1H-tetrazol-5-yl)-benzyl]-5,6,7,8-tetrahydro-pyrido[2,3-d]pyrimidin-2-ylamino}-thiazole-5-carboxylic acid ethyl ester | 1.53[b] | 577.23 |

TABLE C2-continued

| Ex. | Z | R⁵ | Name | HPLC Retention (min) | MS Reported |
|---|---|---|---|---|---|
| C15 | 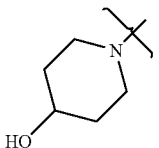 | 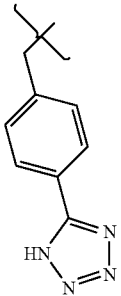 | 2-{4-(4-Hydroxy-piperidin-1-yl)-8-[4-(1H-tetrazol-5-yl)-benzyl]-5,6,7,8-tetrahydro-pyrido[2,3-d]pyrimidin-2-ylamino}-4-methyl-thiazole-5-carboxylic acid ethyl ester | 1.55[b] | 576.22 |
| C16 | 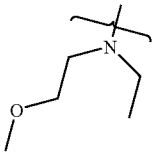 | 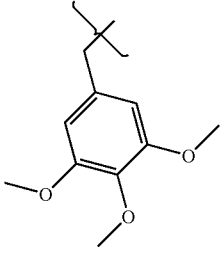 | 2-[4-[Ethyl-(2-methoxy-ethyl)-amino]-8-(3,4,5-trimethoxy-benzyl)-5,6,7,8-tetrahydro-pyrido[2,3-d]pyrimidin-2-ylamino]-4-methyl-thiazole-5-carboxylic acid ethyl ester | 1.53[b] | 600.74 |
| C17 | 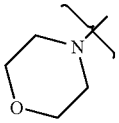 | 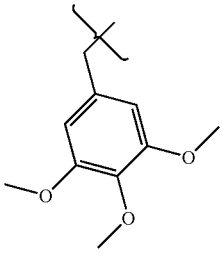 | 4-Methyl-2-[4-morpholin-4-yl-8-(3,4,5-trimethoxy-benzyl)-5,6,7,8-tetrahydro-pyrido[2,3-d]pyrimidin-2-ylamino]-thiazole-5-carboxylic acid ethyl ester | 1.68[b] | 584.70 |
| C18 | 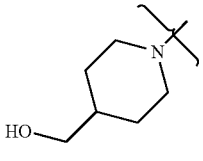 | 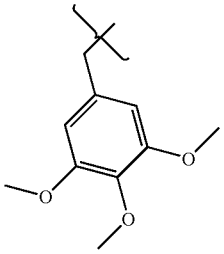 | 2-[4-(4-Hydroxymethyl-piperidin-1-yl)-8-(3,4,5-trimethoxy-benzyl)-5,6,7,8-tetrahydro-pyrido[2,3-d]pyrimidin-2-ylamino]-4-methyl-thiazole-5-carboxylic acid ethyl ester | 1.63[b] | 612.75 |
| C19 | 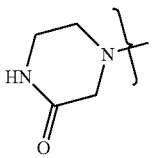 | 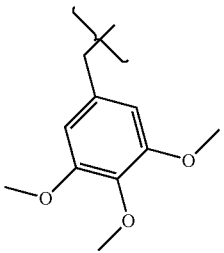 | 4-Methyl-2-[4-(3-oxo-piperazin-1-yl)-8-(3,4,5-trimethoxy-benzyl)-5,6,7,8-tetrahydro-pyrido[2,3-d]pyrimidin-2-ylamino]-thiazole-5-carboxylic acid ethyl ester | 1.62[b] | 597.70 |

TABLE C2-continued

| Ex. | Z | R⁵ | Name | HPLC Retention (min) | MS Reported |
|---|---|---|---|---|---|
| C20 | Cl | 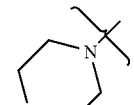 | 2-[4-Chloro-8-(1,1,3-trioxo-2,3-dihydro-1H-1λ⁶-benzyl[d]isothiazol-5-ylmethyl)-5,6,7,8-tetrahydro-pyrido[2,3-d]pyrimidin-2-ylamino]-4-methyl-thiazole-5-carboxylic acid ethyl ester | 1.67$^c$ | 550.14 |
| C21 | 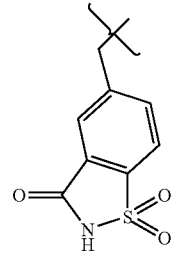 | 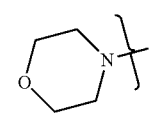 | 4-Methyl-2-[4-morpholin-4-yl-8-(1,1,3-trioxo-2,3-dihydro-1H-1λ⁶-benzo[d]isothiazol-5-ylmethyl)-5,6,7,8-tetrahydro-pyrido[2,3-d]pyrimidin-2-ylamino]-thiazole-5-carboxylic acid ethyl ester | 1.43$^b$ | 600.27 |
| C22 | 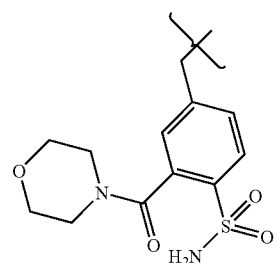 | 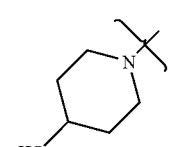 | 4-Methyl-2-{8-[3-(morpholine-4-carbonyl)-4-sulfamoyl-benzyl]-4-morpholin-4-yl-5,6,7,8-tetrahydro-pyrido[2,3-d]pyrimidin-2-ylamino}-thiazole-5-carboxylic acid ethyl ester | 1.43$^b$ | 687.32 |
| C23 | 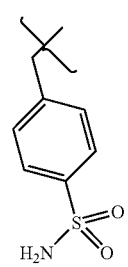 | 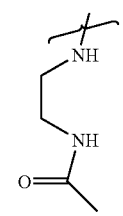 | 2-[4-(4-Hydroxy-piperidin-1-yl)-8-(4-sulfamoyl-benzyl)-5,6,7,8-tetrahydro-pyrido[2,3-d]pyrimidin-2-ylamino]-4-methyl-thiazole-5-carboxylic acid ethyl ester | 1.22$^c$ | 588.28 |
| C24 | 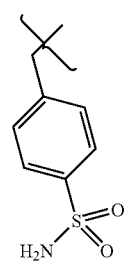 | | 2-[4-(2-Acetylamino-ethylamino)-8-(4-sulfamoyl-benzyl)-5,6,7,8-tetrahydro-pyrido[2,3-d]pyrimidin-2-ylamino]-4-methyl-thiazole-5-carboxylic acid ethyl ester | 1.24$^c$ | 589.25 |

TABLE C2-continued

| Ex. | Z | R⁵ | Name | HPLC Retention (min) | MS Reported |
|---|---|---|---|---|---|
| C25 | morpholin-4-yl | 4-sulfamoyl-benzyl | 4-Methyl-2-[4-morpholin-4-yl-8-(4-sulfamoyl-benzyl)-5,6,7,8-tetrahydro-pyrido[2,3-d]pyrimidin-2-ylamino]-thiazole-5-carboxylic acid ethyl ester | 1.46[b] | 574.20 |
| C26 | 3,4,5-trimethoxy-benzylamino | 4-sulfamoyl-benzyl | 4-Methyl-2-[8-(4-sulfamoyl-benzyl)-4-(3,4,5-trimethoxy-benzylamino)-5,6,7,8-tetrahydro-pyrido[2,3-d]pyrimidin-2-ylamino]-thiazole-5-carboxylic acid ethyl ester | 1.58[b] | 684.22 |
| C27 | CH₃NH | 4-sulfamoyl-benzyl | 4-Methyl-2-[4-methylamino-8-(4-sulfamoyl-benzyl)-5,6,7,8-tetrahydro-pyrido[2,3-d]pyrimidin-2-ylamino]-thiazole-5-carboxylic acid ethyl ester | 1.44[b] | 518.19 |
| C28 | 3-oxo-piperazin-1-yl | 4-sulfamoyl-benzyl | 4-Methyl-2-[4-(3-oxo-piperazin-1-yl)-8-(4-sulfamoyl-benzyl)-5,6,7,8-tetrahydro-pyrido[2,3-d]pyrimidin-2-ylamino]-thiazole-5-carboxylic acid ethyl ester | 1.45[b] | 587.15 |
| C29 | Cl | 4-(5-oxo-4,5-dihydro-[1,2,4]oxadiazol-3-yl)-benzyl | 2-{4-Chloro-8-[4-(5-oxo-4,5-dihydro-[1,2,4]oxadiazol-3-yl)-benzyl]-5,6,7,8-tetrahydro-pyrido[2,3-d]pyrimidin-2-ylamino}-4-methyl-thiazole-5-carboxylic acid ethyl ester | 1.76[b] | 528.94 |

TABLE C2-continued

| Ex. | Z | R[5] | Name | HPLC Retention (min) | MS Reported |
|---|---|---|---|---|---|
| C30 | 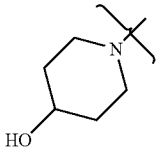 | 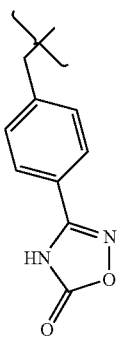 | 2-{4-(4-Hydroxy-piperidin-1-yl)-8-[4-(5-oxo-4,5-dihydro-[1,2,4]oxadiazol-3-yl)-benzyl]-5,6,7,8-tetrahydro-pyrido[2,3-d]pyrimidin-2-ylamino}-4-methyl-thiazole-5-carboxylic acid ethyl ester | 1.61[b] | 593.49 |
| C31 | 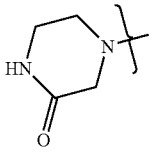 | 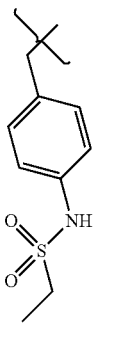 | 2-[8-(4-Ethanesulfonylamino-benzyl)-4-(3-oxo-piperazin-1-yl)-5,6,7,8-tetrahydro-pyrido[2,3-d]pyrimidin-2-ylamino]-4-methyl-thiazole-5-carboxylic acid ethyl ester | 1.59[b] | 614.75 |
| C32 | 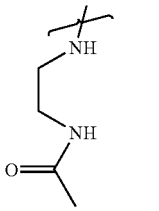 | 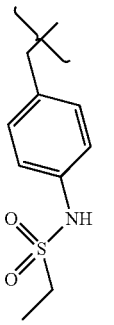 | 2-[4-(2-Acetylamino-ethylamino)-8-(4-ethanesulfonylamino-benzyl)-5,6,7,8-tetrahydro-pyrido[2,3-d]pyrimidin-2-ylamino]-4-methyl-thiazole-5-carboxylic acid ethyl ester | 1.59[b] | 616.77 |
| C33 | 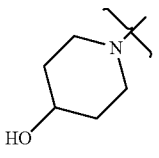 | 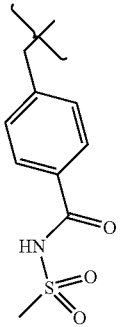 | 2-[4-(4-Hydroxy-piperidin-1-yl)-8-(4-methanesulfonylamino carbonyl-benzyl)-5,6,7,8-tetrahydro-pyrido[2,3-d]pyrimidin-2-ylamino]-4-methyl-thiazole-5-carboxylic acid ethyl ester | 1.42[c] | 629.76 |

TABLE C2-continued

| Ex. | Z | R⁵ | Name | HPLC Retention (min) | MS Reported |
|---|---|---|---|---|---|
| C34 | 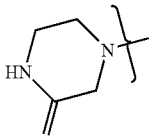 | 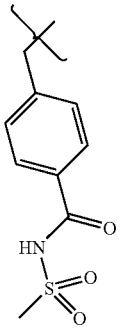 | 2-[8-(4-Methanesulfonylamino carbonyl-benzyl)-4-(3-oxo-piperazin-1-yl)-5,6,7,8-tetrahydro-pyrido[2,3-d]pyrimidin-2-ylamino]-4-methyl-thiazole-5-carboxylic acid ethyl ester | 1.50[b] | 628.73 |
| C35 | 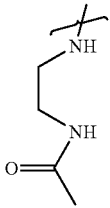 | 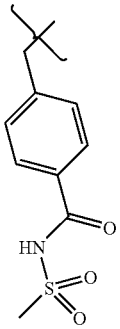 | 2-[4-(2-Acetylamino-ethylamino)-8-(4-methanesulfonylamino carbonyl-benzyl)-5,6,7,8-tetrahydro-pyrido[2,3-d]pyrimidin-2-ylamino]-4-methyl-thiazole-5-carboxylic acid ethyl ester | 1.54[b] | 630.75 |
| C36 | 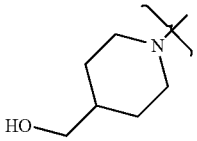 | 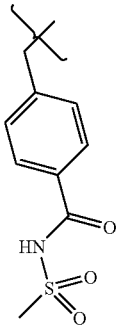 | 2-[4-(4-Hydroxymethyl-piperidin-1-yl)-8-(4-methanesulfonylamino carbonyl-benzyl)-5,6,7,8-tetrahydro-pyrido[2,3-d]pyrimidin-2-ylamino]-4-methyl-thiazole-5-carboxylic acid ethyl ester | 1.55[b] | 643.79 |
| C37 | 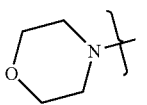 | 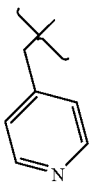 | 4-Methyl-2-(4-morpholin-4-yl-8-pyridin-4-ylmethyl-5,6,7,8-tetrahydro-pyrido[2,3-d]pyrimidin-2-ylamino)-thiazole-5-carboxylic acid ethyl ester | 1.37[b] | 495.61 |
| C38 | 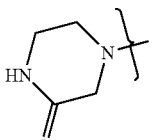 | 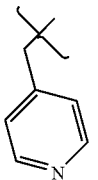 | 4-Methyl-2-[4-(3-oxo-piperazin-1-yl)-8-pyridin-4-ylmethyl-5,6,7,8-tetrahydro-pyrido[2,3-d]pyrimidin-2-ylamino]-thiazole-5-carboxylic acid ethyl ester | 1.32[b] | 508.61 |

TABLE C2-continued

| Ex. | Z | R⁵ | Name | HPLC Retention (min) | MS Reported |
|---|---|---|---|---|---|
| C39 | 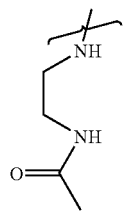 | 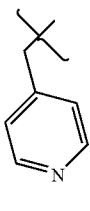 | 2-[4-(2-Acetylamino-ethylamino)-8-pyridin-4-ylmethyl-5,6,7,8-tetrahydro-pyrido[2,3-d]pyrimidin-2-ylamino]-4-methyl-thiazole-5-carboxylic acid ethyl ester | 1.25[b] | 510.62 |
| C40 | 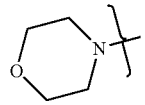 | 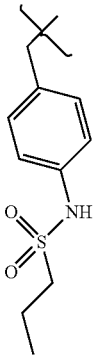 | 4-Mehtyl-2-{4-morpholin-4-yl-8-[4-(propane-1-sulfonylamino)-benzyl]-5,6,7,8-tetrahydro-pyrido[2,3-d]pyrimidin-2-ylamino}-thiazole-5-carboxylic acid ethyl ester | 1.68[b] | 615.78 |
| C41 | 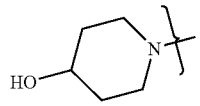 | 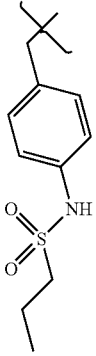 | 2-{4-(4-Hydroxy-piperidin-1-yl)-8-[4-(propane-1-sulfonylamino)-benzyl]-5,6,7,8-tetrahydro-pyrido[2,3-d]pyrimidin-2-ylamino}-4-methyl-thiazole-5-carboxylic acid ethyl ester | 1.64[b] | 629.81 |
| C42 | 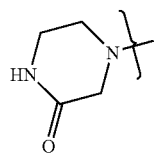 | 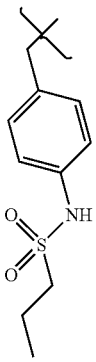 | 4-Methyl-2-{4-(3-oxo-piperazin-1-yl)-8-[4-(propane-1-sulfonylamino)-benzyl]-5,6,7,8-tetrahydro-pyrido[2,3-d]pyrimidin-2-ylamino}-thiazole-5-carboxylic acid ethyl ester | 1.66[b] | 628.78 |

TABLE C2-continued

| Ex. | Z | R⁵ | Name | HPLC Retention (min) | MS Reported |
|---|---|---|---|---|---|
| C43 | 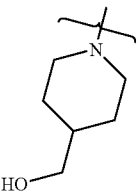 | 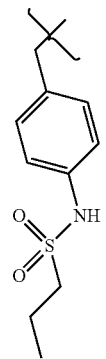 | 2-{4-(4-Hydroxymethyl-piperidin-1-yl)-8-[4-(propane-1-sulfonylamino)-benzyl]-5,6,7,8-tetrahydro-pyrido[2,3-d]pyrimidin-2-ylamino}-4-methyl-thiazole-5-carboxylic acid ethyl ester | 1.68[b] | 643.83 |
| C44 | 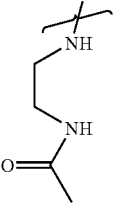 | 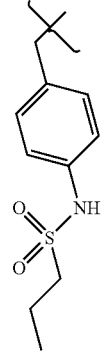 | 2-{4-(2-Acetylamino-ethylamino)-8-[4-(propane-1-sulfonylamino)-benzyl]-5,6,7,8-tetrahydro-pyrido[2,3-d]pyrimidin-2-ylamino}-4-methyl-thiazole-5-carboxylic acid ethyl ester | 1.66[b] | 630.79 |
| C45 | 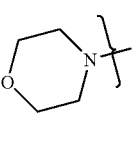 | 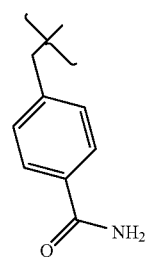 | 2-[8-(4-Carbamoyl-benzyl)-4-morpholin-4-yl-5,6,7,8-tetrahydro-pyrido[2,3-d]pyrimidin-2-ylamino]-4-methyl-thiazole-5-carboxylic acid ethyl ester | 1.51[b] | 537.65 |
| C46 | 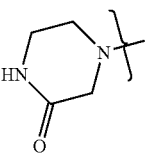 | 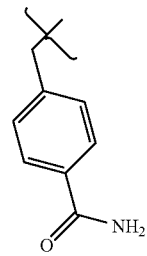 | 2-[8-(4-Carbamoyl-benzyl)-4-(3-oxo-piperazin-1-yl)-5,6,7,8-tetrahydro-pyrido[2,3-d]pyrimidin-2-ylamino]-4-methyl-thiazole-5-carboxylic acid ethyl ester | 1.49[b] | 550.64 |
| C47 | 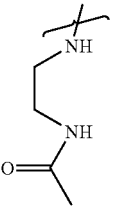 | 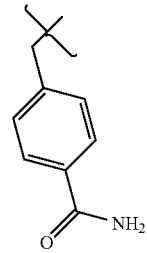 | 2-[4-(2-Acetylamino-ethylamino)-8-(4-carbamoyl-benzyl)-5,6,7,8-tetrahydro-pyrido[2,3-d]pyrimidin-2-ylamino]-4-methyl-thiazole-5-carboxylic acid ethyl ester | 1.52[b] | 552.66 |

TABLE C2-continued

| Ex. | Z | R⁵ | Name | HPLC Retention (min) | MS Reported |
|---|---|---|---|---|---|
| C48 | 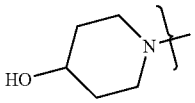 | 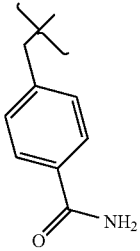 | 2-[8-(4-Carbamoyl-benzyl)-4-(4-hydroxy-piperidin-1-yl)-5,6,7,8-tetrahydro-pyrido[2,3-d]pyrimidin-2-ylamino]-4-methyl-thiazole-5-carboxylic acid ethyl ester | 1.57[b] | 551.67 |
| C49 | 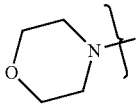 | 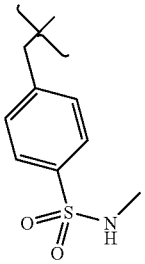 | 4-Methyl-2-[8-(4-methylsulfamoyl-benzyl)-morpholin-4-yl-5,6,7,8-tetrahydro-pyrido[2,3-d]pyrimidin-2-ylamino]-thiazole-5-carboxylic acid ethyl ester | 1.55[b] | 587.72 |
| C50 | 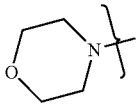 | 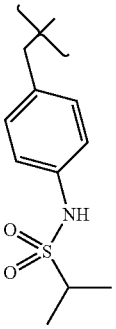 | 4-Methyl-2-{4-morpholin-4-yl-8-[4-(propane-2-sulfonylamino)-benzyl]-5,6,7,8-tetrahydro-pyrido[2,3-d]pyrimidin-2-ylamino}-thiazole-5-carboxylic acid ethyl ester | 1.67[b] | 615.78 |
| C51 | 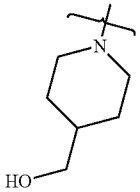 | 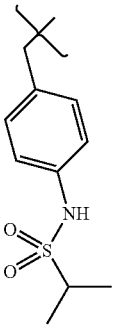 | 2-{4-(4-Hydroxymethyl-piperidin-1-yl)-8-[4-(propane-2-sulfonylamino)-benzyl]-5,6,7,8-tetrahydro-pyrido[2,3-d]pyrimidin-2-ylamino}-4-methyl-thiazole-5-carboxylic acid ethyl ester | 1.66[b] | 643.83 |
| C52 | 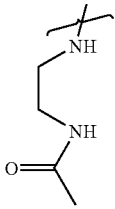 | 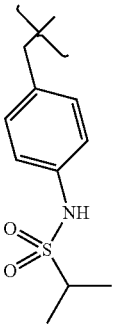 | 2-{4-(2-Acetylamino-ethylamino)-8-[4-(propane-2-sulfonylamino)-benzyl]-5,6,7,8-tetrahydro-pyrido[2,3-d]pyrimidin-2-ylamino}-4-methyl-thiazole-5-carboxylic acid ethyl ester | 1.64[b] | 630.79 |

TABLE C2-continued

| Ex. | Z | R⁵ | Name | HPLC Retention (min) | MS Reported |
|---|---|---|---|---|---|
| C53 | 3-oxopiperazin-1-yl | 4-(propane-2-sulfonylamino)benzyl | 4-Methyl-2-{4-(3-oxo-piperazin-1-yl)-8-[4-(propane-2-sulfonylamino)-benzyl]-5,6,7,8-tetrahydro-pyrido[2,3-d]pyrimidin-2-ylamino}-thiazole-5-carboxylic acid ethyl ester | 1.63[b] | 628.78 |
| C54 | 4-hydroxypiperidin-1-yl | 4-(propane-2-sulfonylamino)benzyl | 2-{4-(4-Hydroxy-piperidin-1-yl)-8-[4-(propane-2-sulfonylamino)-benzyl]-5,6,7,8-tetrahydro-pyrido[2,3-d]pyrimidin-2-ylamino}-4-methyl-thiazole-5-carboxylic acid ethyl ester | 1.66[b] | 629.81 |
| C55 | 4-hydroxypiperidin-1-yl | 4-isobutylcarbamoylbenzyl | 2-[4-(4-Hydroxy-piperidin-1-yl)-8-(4-isobutylcarbamoyl-benzyl)-5,6,7,8-tetrahydro-pyrido[2,3-d]pyrimidin-2-ylamino]-4-methyl-thiazole-5-carboxylic acid ethyl ester | 1.68[d] | 607.78 |
| C56 | 2-acetylaminoethylamino | 4-isobutylcarbamoylbenzyl | 2-[4-(2-Acetylamino-ethylamino)-8-(4-isobutylcarbamoyl-benzyl)-5,6,7,8-tetrahydro-pyrido[2,3-d]pyrimidin-2-ylamino]-4-methyl-thiazole-5-carboxylic acid ethyl ester | 1.73[b] | 608.77 |

TABLE C2-continued

| Ex. | Z | R⁵ | Name | HPLC Retention (min) | MS Reported |
|---|---|---|---|---|---|
| C57 | isobutylamino | 4-(isobutylcarbamoyl)benzyl | 2-[4-Isobutylamino-8-(4-isobutylcarbamoyl-benzyl)-5,6,7,8-tetrahydro-pyrido[2,3-d]pyrimidin-2-ylamino]-4-methyl-thiazole-5-carboxylic acid ethyl ester | 1.88[b] | 579.77 |
| C58 | morpholin-4-yl | 4-(isobutylcarbamoyl)benzyl | 2-[8-(4-Isobutylcarbamoyl-benzyl)-4-morpholin-4-yl-5,6,7,8-tetrahydro-pyrido[2,3-d]pyrimidin-2-ylamino]-4-methyl-thiazole-5-carboxylic acid ethyl ester | 1.74[b] | 593.75 |
| C59 | 4-hydroxy-piperidin-1-yl | 4-(ethanesulfonylamino)benzyl | 2-[8-(4-Ethanesulfonylamino-benzyl)-4-(4-hydroxy-piperidin-1-yl)-5,6,7,8-tetrahydro-pyrido[2,3-d]pyrimidin-2-ylamino]-4-methyl-thiazole-5-carboxylic acid ethyl ester | 1.61[b] | 615.78 |
| C60 | morpholin-4-yl | 4-(ethanesulfonylamino)benzyl | 2-[8-(4-Ethanesulfonylamino-benzyl)-4-morpholin-4-yl-5,6,7,8-tetrahydro-pyrido[2,3-d]pyrimidin-2-ylamino]-4-methyl-thiazole-5-carboxylic acid ethyl ester | 1.63[b] | 601.75 |

TABLE C2-continued

| Ex. | Z | R[5] | Name | HPLC Retention (min) | MS Reported |
|---|---|---|---|---|---|
| C61 |  | 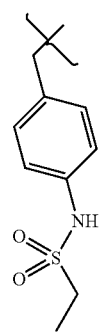 | 2-[8-(4-Ethanesulfonylamino-benzyl)-4-isobutylamino-5,6,7,8-tetrahydro-pyrido[2,3-d]pyrimidin-2-ylamino]-4-methyl-thiazole-5-carboxylic acid ethyl ester | 1.81[b] | 587.77 |
| C62 |  | 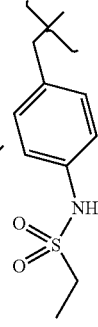 | 2-[8-(4-Ethanesulfonylamino-benzyl)-4-(3,4,5-trimethoxy-benzylamino)-5,6,7,8-tetrahydro-pyrido[2,3-d]pyrimidin-2-ylamino]-4-methyl-thiazole-5-carboxylic acid ethyl ester | 1.72[b] | 711.87 |
| C63 |  | 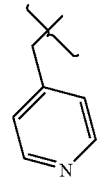 | 2-(4-Isobutylamino-8-pyridin-4-ylmethyl-5,6,7,8-tetrahydro-pyrido[2,3-d]pyrimidin-2-ylamino)-4-methyl-thiazole-5-carboxylic acid ethyl ester | 1.50[b] | 481.62 |
| C64 |  | 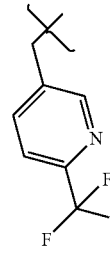 | 2-[4-(4-Hydroxy-piperidin-1-yl)-8-(6-trifluoromethyl-pyridin-3-ylmethyl)-5,6,7,8-tetrahydro-pyrido[2,3-d]pyrimidin-2-ylamino]-4-methyl-thiazole-5-carboxylic acid ethyl ester | 1.76[b] | 578.71 |
| C65 |  | 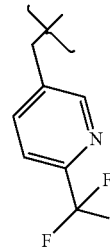 | 2-[4-(2-Acetylamino-ethylamino)-8-(6-trifluoromethyl-pyridin-3-ylmethyl)-5,6,7,8-tetrahydro-pyrido[2,3-d]pyrimidin-2-ylamino]-4-methyl-thiazole-5-carboxylic acid ethyl ester | 1.68[b] | 579.15 |

TABLE C2-continued

| Ex. | Z | R⁵ | Name | HPLC Retention (min) | MS Reported |
|---|---|---|---|---|---|
| C66 | 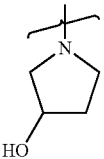 | 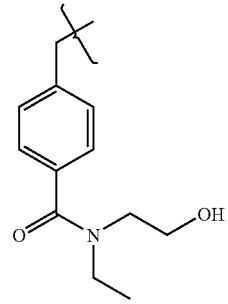 | 2-[8-{4-[Ethyl-(2-hydroxy-ethyl)-carbamoyl]-benzyl}-4-(3-hydroxy-pyrrolidin-1-yl)-5,6,7,8-tetrahydro-pyrido[2,3-d]pyrimidin-2-ylamino]-4-methyl-thiazole-5-carboxylic acid ethyl ester | 1.47[b] | 609.75 |
| C67 | 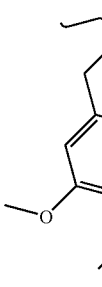 | 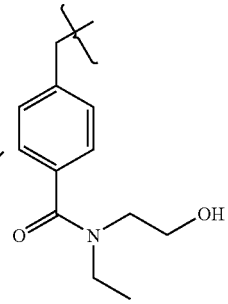 | 2-[8-{4-[Ethyl-(2-hydroxy-ethyl)-carbamoyl]-benzyl}-4-(3,4,5-trimethoxy-benzylamino)-5,6,7,8-tetrahydro-pyrido[2,3-d]pyrimidin-2-ylamino]-4-methyl-thiazole-5-carboxylic acid ethyl ester | 1.58[c] | 719.87 |
| C68 | 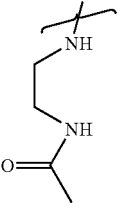 | 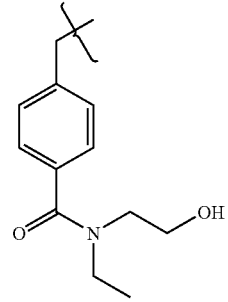 | 2-(4-(2-Acetylamino-ethylamino)-8-{4-[ethyl-(2-hydroxy-ethyl)-carbamoyl]-benzyl}-5,6,7,8-tetrahydro-pyrido[2,3-d]pyrimidin-2-ylamino)-4-methyl-thiazole-5-carboxylic acid ethyl ester | 1.48[c] | 624.77 |
| C69 | 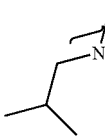 | 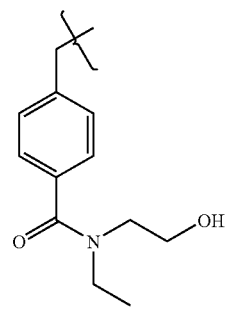 | 2-(8-{4-[Ethyl-(2-hydroxy-ethyl)-carbamoyl]-benzyl}-4-isobutylamino-5,6,7,8-tetrahydro-pyrido[2,3-d]pyrimidin-2-ylamino)-4-methyl-thiazole-5-carboxylic acid ethyl ester | 1.62[b] | 595.77 |

TABLE C2-continued

| Ex. | Z | R⁵ | Name | HPLC Retention (min) | MS Reported |
|---|---|---|---|---|---|
| C70 | 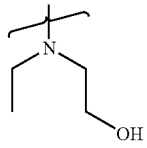 | 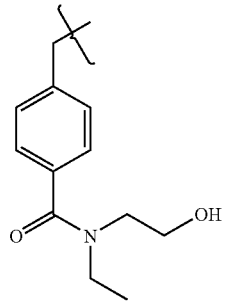 | 2-(4-[Ethyl-(2-hydroxy-ethyl)-amino]-8-{4-[ethyl-(2-hydroxy-ethyl)-carbamoyl]-benzyl}-5,6,7,8-tetrahydro-pyrido[2,3-d]pyrimidin-2-ylamino)-4-methyl-thiazole-5-carboxylic acid ethyl ester | 1.58[b] | 611.77 |
| C71 | 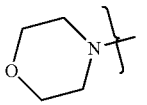 | 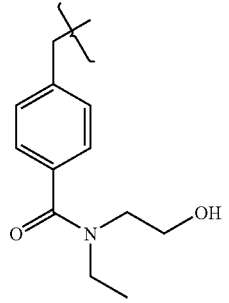 | 2-(8-{4-[Ethyl-(2-hydroxy-ethyl)-carbamoyl]-benzyl}-4-morpholin-4-yl-5,6,7,8-tetrahydro-pyrido[2,3-d]pyrimidin-2-ylamino)-4-methyl-thiazole-5-carboxylic acid ethyl ester | 1.58[b] | 609.75 |
| C72 | 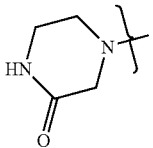 | 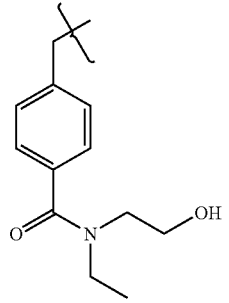 | 2-[8-{4-[Ethyl-(2-hydroxy-ethyl)-carbamoyl]-benzyl}-4-(3-oxo-piperazin-1-yl)-5,6,7,8-tetrahydro-pyrido[2,3-d]pyrimidin-2-ylamino]-4-methyl-thiazole-5-carboxylic acid ethyl ester | 1.57[b] | 622.75 |
| C73 | 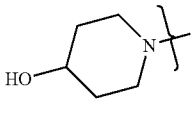 | 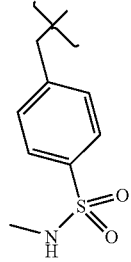 | 2-[4-(4-Hydroxy-piperidin-1-yl)-8-(4-methylsulfamoyl-benzyl)-5,6,7,8-tetrahydro-pyrido[2,3-d]pyrimidin-2-ylamino]-4-methyl-thiazole-5-carboxylic acid ethyl ester | 1.51[b] | 601.75 |
| C74 | 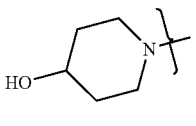 | 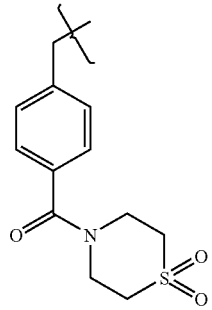 | 2-[8-[4-(1,1-Dioxo-1λ⁶-thiomorpholine-4-carbonyl)-benzyl]-4-(4-hydroxy-piperidin-1-yl)-5,6,7,8-tetrahydro-pyrido[2,3-d]pyrimidin-2-ylamino]-4-methyl-thiazole-5-carboxylic acid ethyl ester | 1.49[b] | 669.83 |

TABLE C2-continued

| Ex. | Z | R⁵ | Name | HPLC Retention (min) | MS Reported |
|---|---|---|---|---|---|
| C75 | (piperazin-2-one, N-linked) | (4-(N-methylsulfamoyl)benzyl) | 4-Methyl-2-[8-(4-methylsulfamoyl-benzyl)-4-(3-oxo-piperazin-1-yl)-5,6,7,8-tetrahydro-pyrido[2,3-d]pyrimidin-2-ylamino]-thiazole-5-carboxylic acid ethyl ester | 1.54$^b$ | 600.72 |
| C76 | (1-hydroxymethyl-2-methyl-propylamino) | (4-(N-methylsulfamoyl)benzyl) | 2-[4-(1-Hydroxymethyl-2-methyl-propylamino)-8-(4-methylsulfamoyl-benzyl)-5,6,7,8-tetrahydro-pyrido[2,3-d]pyrimidin-2-ylamino]-4-methyl-thiazole-5-carboxylic acid ethyl ester | 1.68$^b$ | 603.77 |
| C77 | (2-acetylamino-ethylamino) | (4-(N-methylsulfamoyl)benzyl) | 2-[4-(2-Acetylamino-ethylamino)-8-(4-methylsulfamoyl-benzyl)-5,6,7,8-tetrahydro-pyrido[2,3-d]pyrimidin-2-ylamino]-4-methyl-thiazole-5-carboxylic acid ethyl ester | 1.55$^b$ | 602.74 |
| C78 | (2-hydroxy-ethylamino) | (4-(N-methylsulfamoyl)benzyl) | 2-[4-(2-Hydroxy-ethylamino)-8-(4-methylsulfamoyl-benzyl)-5,6,7,8-tetrahydro-pyrido[2,3-d]pyrimidin-2-ylamino]-4-methyl-thiazole-5-carboxylic acid ethyl ester | 1.51$^b$ | 561.69 |
| C79 | (ethyl-(2-hydroxy-ethyl)-amino) | (4-(N-methylsulfamoyl)benzyl) | 2-[4-[Ethyl-(2-hydroxy-ethyl)-amino]-8-(4-methylsulfamoyl-benzyl)-5,6,7,8-tetrahydro-pyrido[2,3-d]pyrimidin-2-ylamino]-4-methyl-thiazole-5-carboxylic acid ethyl ester | 1.53$^b$ | 589.74 |

TABLE C2-continued

| Ex. | Z | R⁵ | Name | HPLC Retention (min) | MS Reported |
|---|---|---|---|---|---|
| C80 | 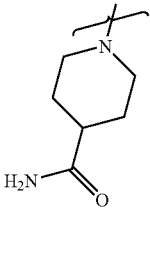 | 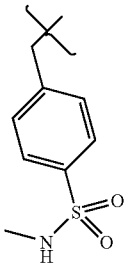 | 2-[4-(4-Carbamoyl-piperidin-1-yl)-8-(4-methylsulfamoyl-benzyl)-5,6,7,8-tetrahydro-pyrido[2,3-d]pyrimidin-2-ylamino]-4-methyl-thiazole-5-carboxylic acid ethyl ester | 1.47$^d$ | 628.78 |
| C81 | 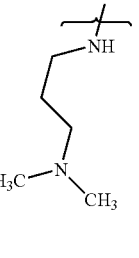 | 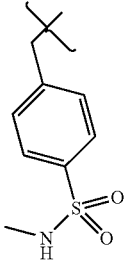 | 2-[4-(3-Dimethylamino-propylamino)-8-(4-methylsulfamoyl-benzyl)-5,6,7,8-tetrahydro-pyrido[2,3-d]pyrimidin-2-ylamino]-4-methyl-thiazole-5-carboxylic acid ethyl ester | 1.42$^b$ | 602.78 |
| C82 | 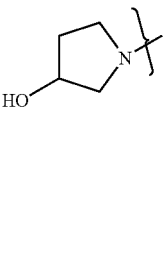 | 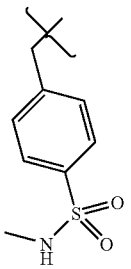 | 2-[4-(3-Hydroxy-pyrrolidin-1-yl)-8-(4-methylsulfamoyl-benzyl)-5,6,7,8-tetrahydro-pyrido[2,3-d]pyrimidin-2-ylamino]-4-methyl-thiazole-5-carboxylic acid ethyl ester | 1.48$^b$ | 587.72 |

HPLC conditions used to determined retention times:

$^a$Xterra 5 μm C18 column 4.6 × 30 mm, 10-90% aqueous methanol over 2 min containing 0.2% H$_3$PO$_4$, 5 mL/min, monitoring at 220 nm or 254 nm.

$^b$Phenomenex 5 μm C18 column 4.6 × 30 mm, 10-90% aqueous methanol over 2 min containing 0.2% H$_3$PO$_4$, 5 mL/min, monitoring at 220 nm or 254 nm.

$^c$YMC CombiScreen 5 μm C18 column 4.6 × 50 mm, 10-90% aqueous methanol over 4 min containing 0.1% TFA, 4 mL/min, monitoring at 220 nm or 254 nm.

$^d$Phenomenex 5 μm C18 column 4.6 × 30 mm, 10-90% aqueous methanol over 2 min containing 0.1% TFA, 5 mL/min, monitoring at 220 nm or 254 nm

Example C83

4-Methyl-2-(4-morpholin-4-yl-8-(2-sulfamoylaminoethyl)-5,6,7,8-tetrahydro-pyrido[2,3-d]pyrimidin-2-ylamino)-thiazole-5-carboxylic acid ethyl ester

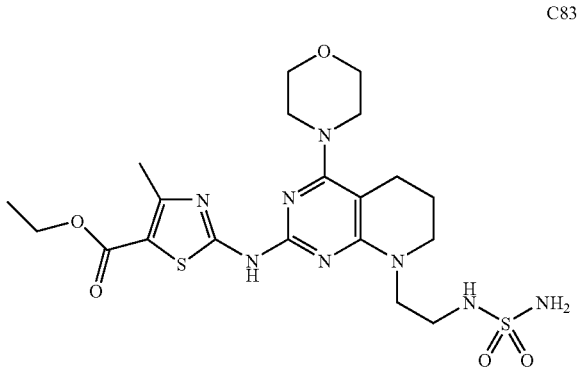

C83

C83.1: 2-[8-(2-tert-Butoxycarbonylamino-ethyl)-4-chloro-5,6,7,8-tetrahydro-pyrido[2,3-d]pyrimidin-2-ylamino]-4-methyl-thiazole-5-carboxylic acid ethyl ester

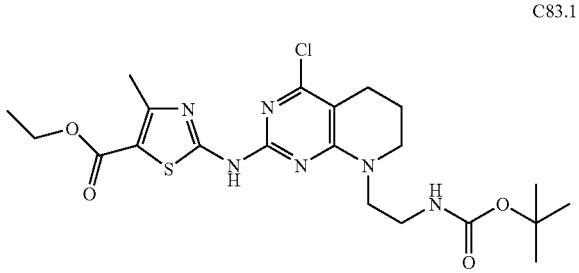

C83.1

Intermediate C83.1 was prepared in an analogous manner to C8.6 with the exception that 3,4,5-trimethoxybenzylamine was replaced by t-butyl N-(2-aminoethyl)carbamate. HPLC: >95% (Phenomenex 5 µm C18 column 4.6×30 mm, 10-90% aqueous methanol over 2 min containing 0.1% TFA, 5 mL/min, monitoring at 254 nm) ret. time=1.43 min., LC/MS (M+H)$^+$=498.16.

C83.2: 2-[8-(2-amino-ethyl)-4-chloro-5,6,7,8-tetrahydro-pyrido[2,3-d]pyrimidin-2-ylamino]-4-methyl-thiazole-5-carboxylic acid ethyl ester

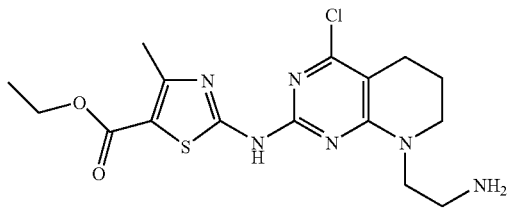

C83.2

Trifluoroacetic acid (20% solution in dichloromethane, 10 mL) was added in one portion to C83.1 (250 mg, 0.42 mmol) at room temperature under a nitrogen atmosphere. After stirring overnight, toluene (1 mL) was added and the solution was concentrated in vacuo. Two subsequent additions of toluene (2×5 mL) followed by concentration in vacuo left the crude trifluoroacetic acid salt of C83.2 as a yellow residue (210 mg, 98%), which was used immediately without characterisation.

C83.3: 2-[8-(2-t-Butoxycarbonyl sulfamoylamino-ethyl) 4-chloro-5,6,7,8-tetrahydro-pyrido[2,3-d]pyrimidin-2-ylamino]-4-methyl-thiazole-5-carboxylic acid ethyl ester

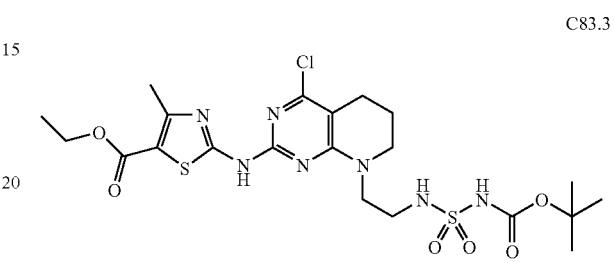

C83.3

Chlorosulfonyl isocyanate (0.076 mL, 0.87 mmol) was dissolved in dry dichloromethane (5 mL) and cooled in an ice-bath, and tert-butyl alcohol (0.064 g, 0.87 mmol) added dropwise. This solution was allowed to stir for 1 hr and was then added to a mixture of the TFA salt of C83.2 (0.39 g, 0.79 mmol) and triethylamine (0.24 mL, 1.7 mmol) in THF (10 mL) under a nitrogen atmosphere. After stirring at room temperature overnight, the reaction mixture was quenched by the addition of water (10 mL). The aqueous phase was extracted with ethyl acetate (3×15 mL), and the combined organics were then dried (MgSO$_4$) and evaporated in vacuo. The crude product was purified by column chromatography using 1:1 hexane:ethyl acetate as eluent to give C83.3 (0.26 g, 56%) as a white solid. $^1$H-NMR (DMSO-d$_6$) δ: 4.23 (2H, q, J=8 Hz), 3.78-3.69 (2H, m), 3.50-3.36 (4H, m), 2.64-2.58 (2H, m), 2.56 (3H, s), 1.56-1.43 (2H, m), 1.39 (9H, s), 1.35 (3H, t, J=8 Hz). HPLC: 95%, ret. time=1.627 min., LC/MS (M+H)$^+$=577.17.

C83.4: 2-[4-Chloro-8-(2-sulfamoylamino-ethyl)-5,6,7,8-tetrahydro-pyrido[2,3-d]pyrimidin-2-ylamino]-4-methyl-thiazole-5-carboxylic acid ethyl ester

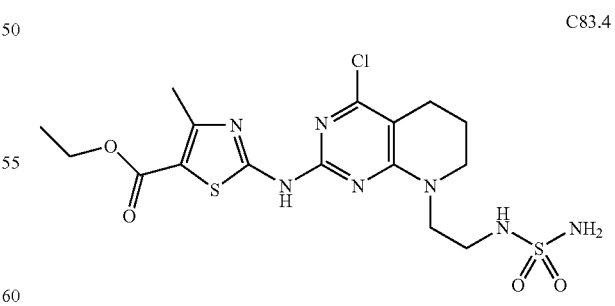

C83.4

Trifluoroacetic acid (20% solution in dichloromethane, 10 mL) was added in one portion to C83.3 (100 mg, 0.17 mmol) at room temperature under a nitrogen atmosphere. After stirring overnight, toluene (1 mL) was added and the solution was concentrated in vacuo. Two subsequent additions of toluene (2×5 mL) followed by concentration in vacuo left the crude trifluoroacetic acid salt of C83.4 as a white residue (98 mg, 100%). $^1$H-NMR (DMSO-$d_6$) δ: 4.23 (2H, q, J=8 Hz), 3.90-3.84 (2H, m), 3.50-3.46 (2H, m), 3.44-3.40 (2H, m), 2.64-2.58 (2H, m), 2.56 (3H, s), 1.56-1.43 (2H, m), 1.35 (3H, t, J=8 Hz). HPLC: 95%, ret. time=1.432 min., LC/MS (M+H)$^+$=476.14.

C83.5: 4-Methyl-2-(4-morpholin-4-yl-8-(2-sulfamoylamino-ethyl)-5,6,7,8-tetrahydro-pyrido[2,3-d]pyrimidin-2-ylamino)-thiazole-5-carboxylic acid ethyl ester Example C83 was prepared in an analogous manner to Example C8 from intermediate C83.4 and morpholine. HPLC: ret. time=1.63 min. (Phenomenex 5 μm C18 column 4.6×30 mm, 10-90% aqueous methanol over 2 min containing 0.2% $H_3PO_4$, 5 mL/min, monitoring at 220 nm or 254 nm), LC/MS (M+H)$^+$=527.72.

Example C84-C86

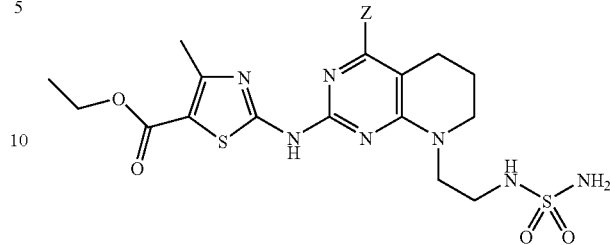

Examples C84 to C86 were prepared in a similar manner to that used for Example C83 utilizing the appropriate amine replacement for morpholine in step C83.5.

TABLE C3

| Ex. | Z | Name | HPLC Retention (min)$^a$ | MS Reported |
| --- | --- | --- | --- | --- |
| C84 | | 2-[4-(2-Acetylamino-ethylamino)-8-(2-sulfamoylamino-ethyl)-5,6,7,8-tetrahydro-pyrido[2,3-d]pyrimidin-2-ylamino]-4-methyl-thiazole-5-carboxylic acid ethyl ester | 1.57 | 542.71 |
| C85 | | 4-Methyl-2-[4-(3-oxo-piperazin-1-yl)-8-(2-sulfamoylamino-ethyl)-5,6,7,8-tetrahydro-pyrido[2,3-d]pyrimidin-2-ylamino]-thiazole-5-carboxylic acid ethyl ester | 1.58 | 540.73 |
| C86 | | 2-[4-(4-Hydroxy-piperidin-1-yl)-8-(2-sulfamoylamino-ethyl)-5,6,7,8-tetrahydro-pyrido[2,3-d]pyrimidin-2-ylamino]-4-methyl-thiazole-5-carboxylic acid ethyl ester | 1.56 | 541.74 |

$^a$Phenomenex 5 μm C18 column 4.6 × 30 mm, 10-90% aqueous methanol over 2 min containing 0.2% $H_3PO_4$, 5 mL/min, monitoring at 220 nm or 254 nm

Example D1

2-[8-(4-Methanesulfonyl-benzyl)-4-(3-oxo-piperazin-1-yl)-6,7-dihydro-pyrimido[5,4-b][1,4]oxazin-2-ylamino]-4-methyl-thiazole-5-carboxylic acid ethyl ester

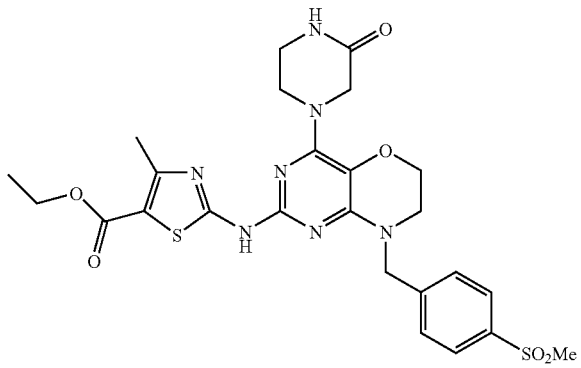

D1.1: 2-Diazo-malonic acid diethyl ester

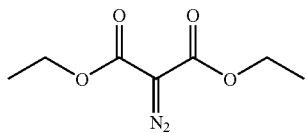

A solution of diethylmalonate (13.9 g, 87 mmol) in acetonitrile (150 ml) at 0-5° C. was added triethylamine (10.5 g, 104 mmol), followed by tosyl azide (20.5 g, 104 mmol) in acetonitrile (100 ml). The reaction mixture was warmed up to room temperature and stirred for 16 hours which was concentrated to afford a crude product. It was diluted with diethyl ether (100 ml) and stirred for 10 minutes. The white solid was removed with filtration. The organic phase was washed with 1 N NaOH solution (50 ml), water (50 ml), brine (50 ml), and dried over sodium sulfate. The solution was filtered through florisil and concentrated in vacuo. The crude product mixture was purified by silica gel column chromatography with hexanes:EtOAc (100:15) to yield D1.1 (16.38 g, 100%). $^1$H-NMR (CDCl$_3$) δ: 4.35 (4H, q, J=7 Hz), 1.37 (3H, t, J=7 Hz). HPLC: 92.6%, ret. time=2.220 min., LC/MS (M+H)$^+$=187.

D1.2: 2-(2,2-Diethoxy-ethoxy)-malonic acid diethyl ester

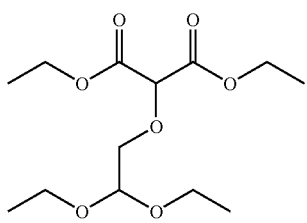

A solution of D1.1 (16.3 g, 87.5 mmol), glycoldehyde diethyl acetal (10.2 g, 76.2 mmol) and rhodium(II) acetate dimer (0.674 g, 1.52 mmol) in toluene (250 ml) was heated to 65° C. for 2 hours and then it was cooled to room temperature. The catalyst was removed by filtration. The filtrate was concentrated to yield a crude product which was purified by silica gel column chromatography with hexanes: EtOAc (7:3) to yield D1.2 (14.86 g, 67%). $^1$H-NMR (CDCl$_3$) δ: 4.79 (1H, s), 4.77 (1H, t, J=5 Hz), 4.30-4.40 (4H, m), 3.75-3.84 (4H, m), 3.61-3.69 (2H, m), 1.38 (6H, t, J=7 Hz), 1.30 (6H, t, J=7 Hz).

D1.3: 2-[5-(2,2-Diethoxy-ethoxy)-4,6-dihydroxy-pyrimidin-2-ylamino]-4-methyl-thiazole-5-carboxylic acid ethyl ester

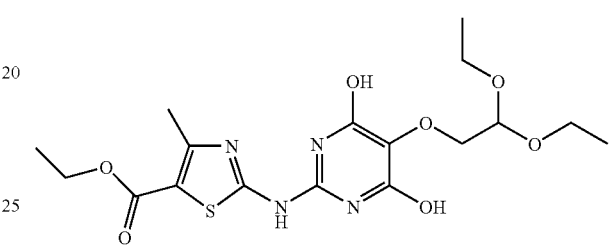

Sodium (2.23 g, 97 mmol) in ethanol (170 ml) was stirred at room temperature until the sodium dissolved. The reaction mixture was treated with A1.1 (7.37 g, 32.3 mmol), followed by D1.2 (11.8 g, 40.4 mmol) and then heated at 100° C. for 3 hours. The reaction mixture was cooled to RT and the solid was collected by filtration to afforded D1.3 (14.8 g, 100%). LC/MS (M+H)$^+$=429.31.

D1.4: 2-[4,6-Dichloro-5-(2,2-diethoxy-ethoxy)-pyrimidin-2-ylamino]-4-methyl-thiazole-5-carboxylic acid ethyl ester

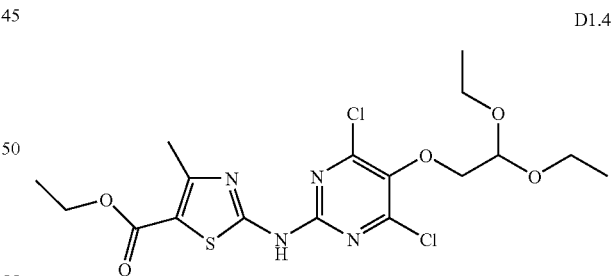

To a solution of diisopropylethylamine (5.46 g, 42 mmol) in POCl$_3$ (12 ml) at 0-5° was added D1.3 (6 g, 14 mmol) in portions. The reaction mixture was warmed up to room temperature and then it was heated to 100° C. for 90 minutes. The reaction mixture was distilled to remove POCl$_3$ to yield a dark crude product which was added to ice water (100 ml) and neutralized with 1 N NaOH to pH 7. The solid was collected to afford D1.4 (4.97 g, 76%). HPLC: 90%, ret. time=4.230 min., LC/MS (M+H)$^+$=465.07.

D1.5: 2-[4-Chloro-7-hydroxy-8-(4-methanesulfonyl-benzyl)-6,7-dihydro-pyrimido[5,4-b][1,4]oxazin-2-ylamino]-4-methyl-thiazole-5-carboxylic acid ethyl ester

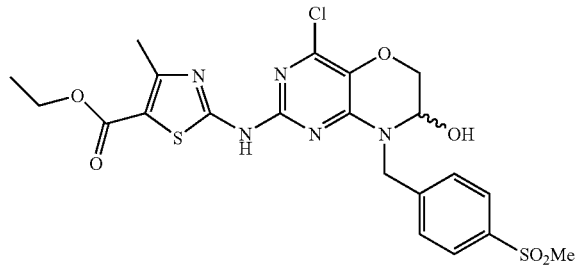

A solution of D1.4 (90 mg, 0.194 mmol), 4-methylsufonylbenzylamine.HCl (45.3 mg, 0.194 mmol) and diisopropylethylamine (56.2 mg, 0.388 mmol) in N-methyl-2-pyrrolidinone (0.5 ml) was heated to 120° C. for 15 minutes under microwave irradiation and then it was cooled down to RT. The reaction mixture was treated with 1N HCl solution (0.225 ml, 0.25 mmol), heated to 120° C. for 15 minutes under microwave irradiation and then it was neutralized with saturated NaHCO$_3$ solution and diluted with water (5 ml). The solid was collected by filtration to yield D1.5 (89 mg, 85%). $^1$H-NMR (DMSO-d$_6$) δ: 11.74 (1H, s), 7.79 (2H, d, J=8 Hz), 7.58 (2H, d, J=8 Hz), 6.73 (1H, d, J=7 Hz), 5.27 (1H, d, J=16 Hz), 5.02 (1H, d, J=7 Hz), 4.82 (1H, d, J=16 Hz), 4.05-4.22 (4H, m), 3.11 (3H, s), 2.40 (3H, s), 1.12 (3H, t, J=7 Hz). HPLC: 87.4%, ret. time=3.120 min., LC/MS (M+H)$^+$=540.02.

D1.6: 2-[4-Chloro-8-(4-methanesulfonyl-benzyl)-6,7-dihydro-pyrimido[5,4-b][1,4]oxazin-2-ylamino]-4-methyl-thiazole-5-carboxylic acid ethyl ester

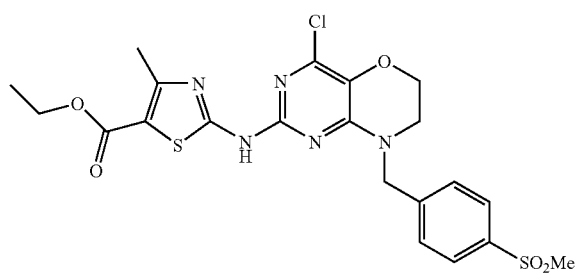

A solution of D1.5 (88 mg, 0.163 mmol) and sodium cyanoborohydride (105 mg, 1.59 mmol) in acetic acid (5 ml) was stirred at RT for three days. The reaction mixture was concentrated to yield a crude product which was treated with water (5 ml) and stirred for 5 minutes. The solid was collected by filtration to afford D1.6 (79.5 mg, 93%). $^1$H-NMR (DMSO-d$_6$) δ: 11.71 (1H, s), 7.83 (2H, d, J=8 Hz), 7.56 (2H, d, J=8 Hz), 7.28 (2H, s), 5.03 (1H, s), 4.19-4.25 (2H, m), 4.07 (2H, q, J=7 Hz), 3.52-3.58 (2H, m), 3.12 (3H, s), 2.40 (3H, s), 1.08 (3H, t, J=7 Hz). HPLC: 80%, ret. time=3.367 min., LC/MS (M+H)$^+$=524.01.

D1.7: 2-[8-(4-Methanesulfonyl-benzyl)-4-(3-oxo-piperazin-1-yl)-6,7-dihydro-pyrimido[5,4-b][1,4]oxazin-2-ylamino]-4-methyl-thiazole-5-carboxylic acid ethyl ester A solution of D1.6 (20 mg, 0.0381 mmol), piperazin-2-one (16 mg, 0.159 mmol) and diisopropylethylamine (20.4 mg, 0.159 mmol) in N-methyl-2-pyrrolidinone (0.5 ml) was heated to 220° C. for 20 minutes under microwave irradiation and then it was cooled down to RT. The reaction mixture was purified by preparative HPLC to yield D1 (13 mg, 58%). $^1$H-NMR (DMSO-d$_6$) δ: 11.14 (1H, s), 7.85 (1H, s), 7.73 (2H, d, J=8 Hz), 7.44 (2H, d, J=8 Hz), 4.84 (2H, s), 3.94-4.04 (6H, m), 3.64-3.70 (2H, m), 3.33-3.37 (2H, m), 3.11-3.17 (2H, m), 3.03 (3H, s), 2.31 (3H, s), 1.02 (3H, t, J=7 Hz). HPLC: >97%, ret. time=3.117 min., LCAMS (M+H)$^+$=588.07.

Example D2 to D7

Examples D2 to D7 were prepared in a similar manner to that used for Example D1 utilizing the appropriate amine replacements.

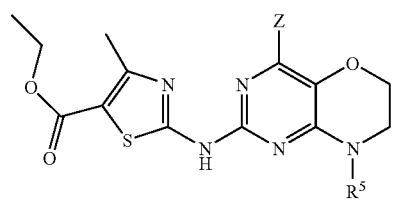

TABLE D

| Ex. | Z | R⁵ | Name | HPLC Retention (min)ᵃ | MS Reported (M + H)⁺ |
|---|---|---|---|---|---|
| D2 |  |  | 4-Methyl-2-[4-morpholin-4-yl-8-(3,4,5-trimethoxy-benzyl)-6,7-dihydro-pyrimido[5,4-b][1,4]oxazin-2-ylamino]-thiazole-5-carboxylic acid ethyl ester | 3.65 | 587.16 |
| D3 |  |  | 4-Methyl-2-[4-morpholin-4-yl-8-(4-sulfamoyl-benzyl)-6,7-dihydro-pyrimido[5,4-b][1,4]oxazin-2-ylamino]-thiazole-5-carboxylic acid ethyl ester | 3.68 | 576.09 |
| D4 | 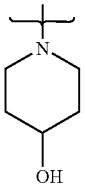 |  | 2-[4-(4-Hydroxy-piperidin-1-yl)-8-(4-sulfamoyl-benzyl)-6,7-dihydro-pyrimido[5,4-b][1,4]oxazin-2-ylamino]-4-methyl-thiazole-5-carboxylic acid ethyl ester | 2.95 | 590.08 |
| D5 | 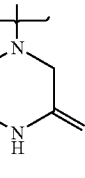 |  | 4-Methyl-2-[4-(3-oxo-piperazin-1-yl)-8-(4-sulfamoyl-benzyl)-6,7-dihydro-pyrimido[5,4-b][1,4]oxazin-2-ylamino]-thiazole-5-carboxylic acid ethyl ester | 3.01 | 589.08 |
| D6 |  |  | 2-[8-(4-Methanesulfonyl-benzyl)-4-morpholin-4-yl-6,7-dihydro-pyrimido[5,4-b][1,4]oxazin-2-ylamino]-4-methyl-thiazole-5-carboxylic acid ethyl ester | 3.39 | 575.09 |

TABLE D-continued

| Ex. | Z | R⁵ | Name | HPLC Retention (min)[a] | MS Reported (M + H)⁺ |
|---|---|---|---|---|---|
| D7 | 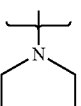 | 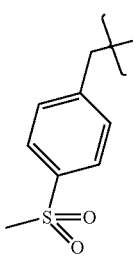 | 2-[4-(4-Hydroxy-piperidin-1-yl)-8-(4-methanesulfonyl-benzyl)-6,7-dihydro-pyrimido[5,4-b][1,4]oxazin-2-ylamino]-4-methyl-thiazole-5-carboxylic acid ethyl ester | 3.08 | 589.10 |

[a]YMC CombiScreen 5 μm C18 column 4.6 × 50 mm, 10-90% aqueous methanol over 4 min containing 0.1% TFA, 4 mL/min, monitoring at 220 nm or 254 nm

Example E1

2-[4-(4-Hydroxy-piperidin-1-yl)-9-(3,4,5-trimethoxy-benzyl)-5,6,7,8-tetrahydro-pyrimido[4,5-b]azepin-2-ylamino]-4-methyl-thiazole-5-carboxylic acid ethyl ester

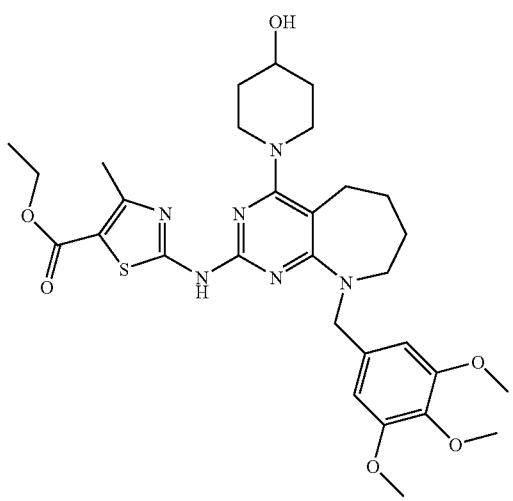

E1

E1.1: 2-Pent-4-enyl-malonic acid diethyl ester

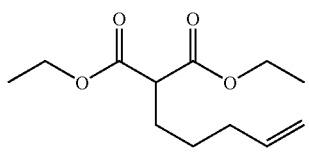

E1.1

A mixture of sodium hydride (60% in mineral oil, 2.4 g, 60.5 mmol, 1.1 eq) and diethyl malonate (8.34 mL, 55 mmol, 1 eq) in DMF (200 mL) was cooled to 0° C. and 5-bromo-1-pentene (6.5 mL, 55 mmol, 1 eq) was added dropwise. The reaction mixture was warmed to rt, stirred for 14 hours and then partitioned between ether and water. The layers were separated, the aqueous layer was extracted with ether (2×250 mL) and the combined organic phases were washed with water (2×) and brine, dried over MgSO₄ and concentrated to give E1.1 as a colorless oil (12.7 g, 100% yield). ¹H NMR (400 MHz, CDCl₃): δ 5.71 (m, 1H), 4.92 (m, 2H), 4.12 (q, J=7.1 Hz, 4H), 3.25 (t, J=7.58 Hz, 1H), 2.01 (m, 2H), 1.83 (m, 2H), 1.36 (m, 2H), 1.20 (t, J=7.1 Hz, 6H).

E1.2: 2-(4,6-Dichloro-5-pent-4-enyl-pyrimidin-2-ylamino)-4-methyl-thiazole-5-carboxylic acid ethyl ester

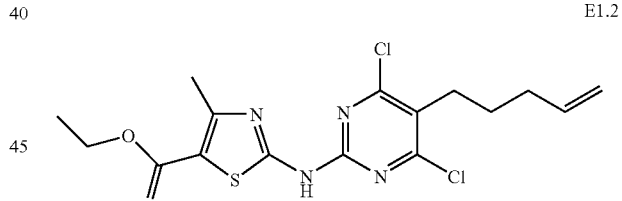

E1.2

To a solution of NaOEt in EtOH [prepared by dissolving Na (1.61 g, 70 mmol, 3.5 eq) in 150 mL of absolute ethanol] was added dropwise E1.1 (5.0 g, 22 mmol, 1.1 eq) and the mixture was stirred at rt for 1 h. A1.1 (4.54 g, 20 mmol, 1 eq) was added, the reaction mixture was heated at reflux for 16 h and then cooled, concentrated to 1/3 of the original volume, diluted with water (200 mL) and acidified with acetic acid. After stirring for 1 h, the solid was collected by filtration, washed with water and dried to afford a light pink solid. The resulting solid was suspended in phosphorous oxychloride (25 mL) and stirred at 95° C. for 2 hours. The reaction mixture was poured onto ice, neutralized with NaOH (pellets) and the solid was collected by filtration and vacuum dried to afford E1.2 as a light brown solid (5.83 g, 66% yield). LC/MS: 401 [M+H]$^+$.

E1.3: 2-[4,6-Dichloro-5-(4-oxo-butyl)-pyrimidin-2-ylamino]-4-methyl-thiazole-5-carboxylic acid ethyl ester

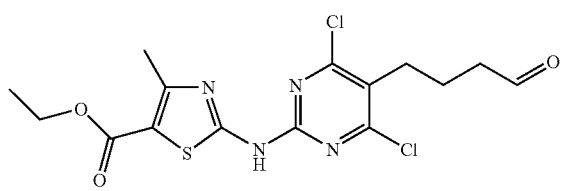

E1.3

To a mixture of E1.2 (2.0 g, 4.98 mmol, 1 eq) and NMO (1.16 g, 9.97 mmol, 2 eq) in THF/water (3:2, 60 mL) at 0° C. was added a solution of OsO$_4$ in 2-methyl-2-propanol (2.5 wt %, 2.0 mL, 0.19 mmol, 0.04 eq). The reaction mixture was warmed to rt, stirred for 168 h and then quenched with a solution of 500 mg of NaHSO$_3$ in 30 mL of water, extracted with AcOEt and dried with MgSO$_4$. The resulting brown solid was dissolved in THF:MeOH (1:1, 60 mL), cooled to 0° C. and treated with Pb(OAc)$_4$ (1.87 g, 4.21 mmol, 1.1 eq). The resulting mixture was warmed to 23° C. and stirred 18 h, then diluted with ethyl acetate, washed with water and brine, dried over MgSO$_4$ and concentrated. The residue was purified by flash chromatography (hexane/ethyl acetate 30% to 50%) to yield E1.3 as a white solid (422 mg, 10% yield). $^1$H NMR (400 MHz, DMSO-d$_6$): δ 9.50 (s, 1H), 4.07 (q, J=7.1 Hz, 2H), 2.58 (m, 2H), 2.39 (m, 2H), 2.35 (s, 3H), 1.61 (m, 2H), 1.09 (t, J=7.1 Hz, 3H). LC/MS: 403 [M+H]$^+$.

E1.4: 2-[4-Chloro-9-(3,4,5-trimethoxy-benzyl)-5,6,7,8-tetrahydro-pyrimido[4,5-b]azepin-2-ylamino]-4-methyl-thiazole-5-carboxylic acid ethyl ester

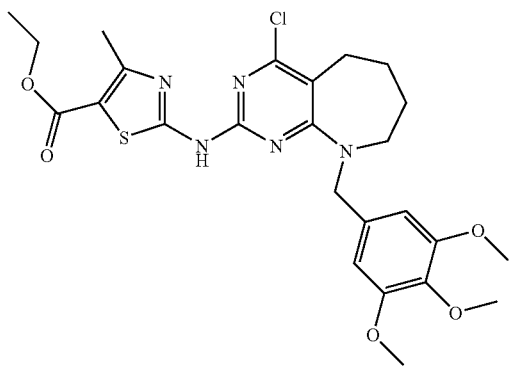

E1.4

To a solution of E1.3 (27 mg, 0.067 mmol, 1.0 eq) and acetic acid (4 µL, 0.067 mmol, 1.0 eq) in THF (3 mL), was added 3,4,5-trimethoxybenzylamine (14 mg, 0.070 mmol, 1.05 eq) and the mixture was stirred for 15 min. Then Na(OAc)$_3$BH (21 mg, 0.1 mmol, 1.5 eq) was added and the reaction was stirred at room temperature. After 45 min, it was quenched with NaHCO$_3$ and extracted with EtOAc, dried MgSO$_4$ and concentrated in vacuo to yield E1.4 (37 mg, 100% yield) as a white solid. $^1$H NMR (400 MHz, DMSO-d$_6$): δ 11.7 (s, 1H), 6.62 (s, 2H), 4.81 (br s, 2H), 4.04 (q, 2H, J=7.1 Hz), 3.65 (s, 6H), 3.56 (s, 3H), 3.46 (m, 2H), 2.79 (m, 2H), 2.42 (s, 3), 1.78 (m, 2H), 1.67 (m, 2H), 1.06 (t, 3H, J=7.1 Hz). LC/MS: 548 [M+H]$^+$.

E1.5: 2-[4-(4-Hydroxy-piperidin-1-yl)-9-(3,4,5-trimethoxy-benzyl)-5,6,7,8-tetrahydro-pyrimido[4,5-b]azepin-2-ylamino]-4-methyl-thiazole-5-carboxylic acid ethyl ester To a solution of E1.4 (30 mg, 0.055 mmol, 1.0 eq) in NMP (1.5 mL), was added 4-hydroxypiperidine (6.6 mg, 0.066 mmol, 1.2 eq), and triethylamine (10 µL). The reaction mixture was stirred at 100° C. for 7 h and then acidified with acetic acid, purified by Prep HPLC (acetonitrile/water/5 mM ammonium acetate, column Primesphere C18 21×100 mm) and freeze dried to give E1 as a white solid (18 mg, 55% yield). $^1$H NMR (400 MHz, DMSO-d$_6$): δ 11.17 (s, 1H), 6.67 (s, 2H), 4.68 (br s, 2H), 4.66 (d, 1H, J=4.3 Hz) 4.07 (q, 2H, J=7.0 Hz), 3.66 (s, 6H), 3.61 (m, 3H), 3.56 (s, 3H), 3.37 (m, 2H), 2.95 (m, 2H), 2.48 (m, 2H), 2.42 (s, 3H), 1.75 (m, 2H), 1.65 (m, 4H), 1.42 (m, 2H), 1.12 (t, 3H, J=7.0 Hz), HPLC: 100%, ret. time=2.017 min. (Acetonitrile/water/5 mM ammonium acetate, column Primesphere C18 4.6×30 mm), LC/MS: 613 [M+H]$^+$.

Example E2-E32

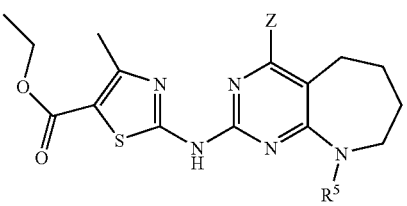

Examples E2 to E32 were prepared in a similar manner to that used for Example E1 utilizing the appropriate amine replacements.

TABLE E

| Ex. | Z | R⁵ | Name | HPLC Retention (min) | MS Reported (M + H)⁺ |
|---|---|---|---|---|---|
| E2 | 4-hydroxy-piperidin-1-yl | 4-sulfamoyl-benzyl | 2-[4-(4-Hydroxy-piperidin-1-yl)-9-(4-sulfamoyl-benzyl)-5,6,7,8-tetrahydro-pyrimido[4,5-b]azepin-2-ylamino]-4-methyl-thiazole-5-carboxylic acid ethyl ester | 1.68 $^a$ | 602 |
| E3 | 4-hydroxy-piperidin-1-yl | 2-(diisopropylamino)ethyl | 2-[9-(2-Diisopropylamino-ethyl)-4-(4-hydroxy-piperidin-1-yl)-5,6,7,8-tetrahydro-pyrimido[4,5-b]azepin-2-ylamino]-4-methyl-thiazole-5-carboxylic acid ethyl ester | 1.71 $^a$ | 560 |
| E4 | 4-hydroxy-piperidin-1-yl | 5-methyl-furan-2-ylmethyl | 2-[4-(4-Hydroxy-piperidin-1-yl)-9-(5-methyl-furan-2-ylmethyl)-5,6,7,8-tetrahydro-pyrimido[4,5-b]azepin-2-ylamino]-4-methyl-thiazole-5-carboxylic acid ethyl ester | 1.95 $^a$ | 527 |
| E5 | 4-hydroxy-piperidin-1-yl | 2-(4-chloro-phenyl)-ethyl | 2-[9-[2-(4-Chloro-phenyl)-ethyl]-4-(4-hydroxy-piperidin-1-yl)-5,6,7,8-tetrahydro-pyrimido[4,5-b]azepin-2-ylamino]-4-methyl-thiazole-5-carboxylic acid ethyl ester | 2.12 $^a$ | 571 |
| E6 | 4-hydroxy-piperidin-1-yl | 2-(4-methoxy-phenyl)-ethyl | 2-{4-(4-Hydroxy-piperidin-1-yl)-9-[2-(4-methoxy-phenyl)-ethyl]-5,6,7,8-tetrahydro-pyrimido[4,5-b]azepin-2-ylamino}-4-methyl-thiazole-5-carboxylic acid ethyl ester | 2.00 $^a$ | 567 |
| E7 | 4-hydroxy-piperidin-1-yl | indan-1-yl | 2-[4-(4-Hydroxy-piperidin-1-yl)-9-indan-1-yl-5,6,7,8-tetrahydro-pyrimido[4,5-b]azepin-2-ylamino]-4-methyl-thiazole-5-carboxylic acid ethyl ester | 2.07 $^a$ | 549 |
| E8 | 4-hydroxy-piperidin-1-yl | 4-nitro-benzyl | 2-[4-(4-Hydroxy-piperidin-1-yl)-9-(4-nitro-benzyl)-5,6,7,8-tetrahydro-pyrimido[4,5-b]azepin-2-ylamino]-4-methyl-thiazole-5-carboxylic acid ethyl ester | 1.92 $^a$ | 568 |

TABLE E-continued

| Ex. | Z | R[5] | Name | HPLC Retention (min) | MS Reported (M + H)[+] |
|---|---|---|---|---|---|
| E9 | 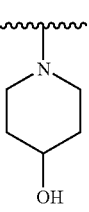 | 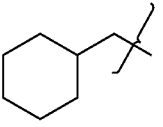 | 2-[9-Cyclohexylmethyl-4-(4-hydroxy-piperidin-1-yl)-5,6,7,8-tetrahydro-pyrimido[4,5-b]azepin-2-ylamino]-4-methyl-thiazole-5-carboxylic acid ethyl ester | 2.16 [a] | 529 |
| E10 | 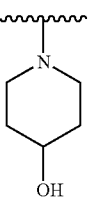 | 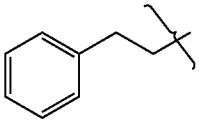 | 2-[4-(4-Hydroxy-piperidin-1-yl)-9-phenethyl-5,6,7,8-tetrahydro-pyrimido[4,5-b]azepin-2-ylamino]-4-methyl-thiazole-5-carboxylic acid ethyl ester | 1.80 [b] | 537 |
| E11 | 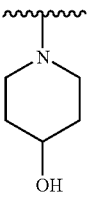 | 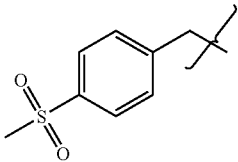 | 2-[4-(4-Hydroxy-piperidin-1-yl)-9-(4-methanesulfonyl-benzyl)-5,6,7,8-tetrahydro-pyrimido[4,5-b]azepin-2-ylamino]-4-methyl-thiazole-5-carboxylic acid ethyl ester | 1.74 [a] | 601 |
| E12 | 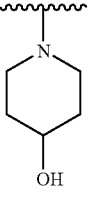 | 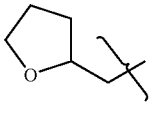 | 2-[4-(4-Hydroxy-piperidin-1-yl)-9-(tetrahydro-furan-2-yl-methyl)-5,6,7,8-tetrahydro-pyrimido[4,5-b]azepin-2-ylamino]-4-methyl-thiazole-5-carboxylic acid ethyl ester | 1.81 [a] | 517 |
| E13 | 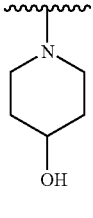 | 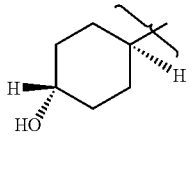 | 2-[9-(4-Hydroxy-cyclohexyl)-4-(4-hydroxy-piperidin-1-yl)-5,6,7,8-tetrahydro-pyrimido[4,5-b]azepin-2-ylamino]-4-methyl-thiazole-5-carboxylic acid ethyl ester | 1.61 [a] | 531 |
| E14 | 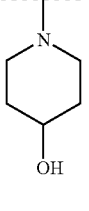 | 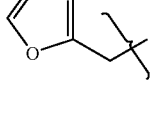 | 2-[9-Furan-2-yl-methyl-4-(4-hydroxy-piperidin-1-yl)-5,6,7,8-tetrahydro-pyrimido[4,5-b]azepin-2-ylamino]-4-methyl-thiazole-5-carboxylic acid | 1.88 [a] | 513 |
| E15 | 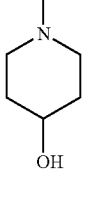 | 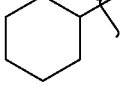 | 2-[9-cyclohexyl-4-(4-hydroxy-piperidin-1-yl)-5,6,7,8-tetrahydro-pyrimido[4,5-b]azepin-2-ylamino]-4-methyl-thiazole-5-carboxylic acid ethyl ester | 2.10 [a] | 515 |

TABLE E-continued

| Ex. | Z | R⁵ | Name | HPLC Retention (min) | MS Reported (M + H)+ |
|---|---|---|---|---|---|
| E16 | 4-hydroxypiperidin-1-yl | 2-methoxyethyl | 2-[4-(4-Hydroxy-piperidin-1-yl)-9-(2-methoxy-ethyl)-5,6,7,8-tetrahydro-pyrimido[4,5-b]azepin-2-ylamino]-4-methyl-thiazole-5-carboxylic acid ethyl ester | 1.75 [a] | 491 |
| E17 | 4-hydroxypiperidin-1-yl | thiophen-2-ylmethyl | 2-[4-(4-Hydroxy-piperidin-1-yl)-9-thiophen-2-yl-methyl-5,6,7,8-tetrahydro-pyrimido[4,5-b]azepin-2-ylamino]-4-methyl-thiazole-5-carboxylic acid ethyl ester | 1.67 [b] | 529 |
| E18 | 4-hydroxypiperidin-1-yl | 3-morpholin-4-yl-propyl | 2-[4-(4-Hydroxy-piperidin-1-yl)-9-(3-morpholin-4-yl-propyl)-5,6,7,8-tetrahydro-pyrimido[4,5-b]azepin-2-ylamino]-4-methyl-thiazole-5-carboxylic acid ethyl ester | 1.22 [b] | 560 |
| E19 | morpholin-4-yl | 4-sulfamoyl-benzyl | 4-Methyl-2-[4-morpholin-4-yl-9-(4-sulfamoyl-benzyl)-5,6,7,8-tetrahydro-pyrimido[4,5-b]azepin-2-ylamino]-thiazole-5-carboxylic acid ethyl ester | 1.55 [b] | 588 |
| E20 | thiomorpholin-4-yl | 4-sulfamoyl-benzyl | 4-Methyl-2-[9-(4-sulfamoyl-benzyl)-4-thiomorpholin-4-yl-5,6,7,8-tetrahydro-pyrimido[4,5-b]azepin-2-ylamino]-thiazole-5-carboxylic acid ethyl ester | 1.72 [b] | 604 |
| E21 | 3-hydroxymethyl-piperidin-1-yl | 4-sulfamoyl-benzyl | 2-[4-(3-Hydroxymethyl-piperidin-1-yl)-9-(4-sulfamoyl-benzyl)-5,6,7,8-tetrahydro-pyrimido[4,5-b]azepin-2-ylamino]-4-methyl-thiazole-5-carboxylic acid ethyl ester | 1.52 [b] | 616 |
| E22 | 2,6-dimethyl-morpholin-4-yl | 4-sulfamoyl-benzyl | 2-[4-(2,6-Dimethyl-morpholin-4-yl)-9-(4-sulfamoyl-benzyl)-5,6,7,8-tetrahydro-pyrimido[4,5-b]azepin-2-ylamino]-4-methyl-thiazole-5-carboxylic acid ethyl ester | 1.74 [b] | 616 |

TABLE E-continued

| Ex. | Z | R[5] | Name | HPLC Retention (min) | MS Reported (M + H)+ |
|---|---|---|---|---|---|
| E23 | 4-acetyl-[1,4]diazepan-1-yl | 4-sulfamoyl-benzyl | 2-[4-(4-Acetyl-[1,4]diazepan-1-yl)-9-(4-sulfamoyl-benzyl)-5,6,7,8-tetrahydro-pyrimido[4,5-b]azepin-2-ylamino]-4-methyl-thiazole-5-carboxylic acid ethyl ester | 1.69 [b] | 643 |
| E24 | 3,4,5-trimethoxy-benzylamino | 4-sulfamoyl-benzyl | 4-Methyl-2-[9-(4-sulfamoyl-benzyl)-4-(3,4,5-trimethoxy-benzylamino)-5,6,7,8-tetrahydro-pyrimido[4,5-b]azepin-2-ylamino]-thiazole-5-carboxylic acid ethyl ester | 1.66 [b] | 698 |
| E25 | 3-oxo-piperazin-1-yl | 4-sulfamoyl-benzyl | 4-Methyl-2-[4-(3-oxo-piperazin-1-yl)-9-(4-sulfamoyl-benzyl)-5,6,7,8-tetrahydro-pyrimido[4,5-b]azepin-2-ylamino]-thiazole-5-carboxylic acid ethyl ester | 1.43 [b] | 601 |
| E26 | morpholin-4-yl | 3,4,5-trimethoxy-benzyl | 4-Methyl-2-[4-morpholin-4-yl-9-(3,4,5-trimethoxy-benzyl)-5,6,7,8-tetrahydro-pyrimido[4,5-b]azepin-2-ylamino]-thiazole-5-carboxylic acid ethyl ester | 1.74 [b] | 599 |
| E27 | thiomorpholin-4-yl | 3,4,5-trimethoxy-benzyl | 4-Methyl-2-[4-thiomorpholin-4-yl-9-(3,4,5-trimethoxy-benzyl)-5,6,7,8-tetrahydro-pyrimido[4,5-b]azepin-2-ylamino]-thiazole-5-carboxylic acid ethyl ester | 1.92 [b] | 615 |
| E28 | 3-hydroxymethyl-piperidin-1-yl | 3,4,5-trimethoxy-benzyl | 2-[4-(3-Hydroxymethyl-piperidin-1-yl)-9-(3,4,5-trimethoxy-benzyl)-5,6,7,8-tetrahydro-pyrimido[4,5-b]azepin-2-ylamino]-4-methyl-thiazole-5-carboxylic acid ethyl ester | 1.71 [b] | 627 |
| E29 | 2,6-dimethyl-morpholin-4-yl | 3,4,5-trimethoxy-benzyl | 2-[4-(2,6-Dimethyl-morpholin-4-yl)-9-(3,4,5-trimethoxy-benzyl)-5,6,7,8-tetrahydro-pyrimido[4,5-b]azepin-2-ylamino]-4-methyl-thiazole-5-carboxylic acid ethyl ester | 1.95 [b] | 627 |

TABLE E-continued

| Ex. | Z | R⁵ | Name | HPLC Retention (min) | MS Reported (M + H)⁺ |
|---|---|---|---|---|---|
| E30 | 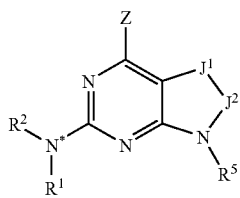 | (3,4,5-trimethoxybenzyl) | 2-[4-(4-Acetyl-[1,4]diazepan-1-yl)-9-(3,4,5-trimethoxy-benzyl)-5,6,7,8-tetrahydro-pyrimido[4,5-b]azepin-2-ylamino]-4-methyl-thiazole-5-carboxylic acid ethyl ester | 1.89 $^b$ | 654 |
| E31 | (3,4,5-trimethoxybenzyl)NH- | (3,4,5-trimethoxybenzyl) | 4-Methyl-2-[9-(3,4,5-trimethoxy-benzyl)-4-(3,4,5-trimethoxy-benzylamino)-5,6,7,8-tetrahydro-pyrimido[4,5-b]azepin-2-ylamino]-thiazole-5-carboxylic acid ethyl ester | 1.84 $^b$ | 709 |
| E32 | 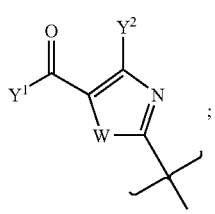 | (3,4,5-trimethoxybenzyl) | 4-Methyl-2-[4-(3-oxo-piperazin-1-yl)-9-(3,4,5-trimethoxy-benzyl)-5,6,7,8-tetrahydro-pyrimido[4,5-b]azepin-2-ylamino]-thiazole-5-carboxylic acid ethyl ester | 1.59 $^b$ | 612 |

HPLC conditions used to determine retention times:
$^a$ 2 min gradient 0-100% B in A; (A; 0.05% ammonium acetate in 90/10 water/acetonitrile; B; 0.05% ammonium acetate in 10/90 water/acetonitrile) using a Primesphere C-18 4.6 × 30 mm column at 254 nm.
$^b$ 2 min gradient 0-100% B in A: (A; 0.05% TFA in 90/10 water/acetonitrile; B; 0.05% TFA in 10/90 water/acetonitrile) using a Primesphere C-18 4.6 × 30 mm column at 254 nm

We claim:
1. A compound of Formula (I)

(I)

their enantiomers, diastereomers, and pharmaceutically acceptable salts thereof, wherein:
$R^1$ is hydrogen or alkyl;
$R^2$ is

;

W is O or S;
$Y^1$ is —$NHT^{15}$ or $OT^{10}$;
$Y^2$ is alkyl or haloalkyl;

Z is —$NR^3R^4$, —$NR^3SO_2R^6$, $OR^4$, $SR^4$, haloalkyl or halogen;
$J^1$ is optionally substituted $C_1$alkylene;
$J^2$ is optionally substituted $C_1$alkylene;
$R^3$ and $R^4$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which may be optionally independently substituted where valance allows with one to three groups $T^4$, $T^5$ and/or $T^6$;
or $R^3$ and $R^4$ may be taken together with the nitrogen atom to which they are attached to form a heterocyclo or heteroaryl ring, either of which is optionally independently substituted where valance allows with one to three groups independently selected from $T^4$, $T^5$ and/or $T^6$;
$R^5$ is
(i) H, cyano, alkyl, alkenyl, alkynyl, cycloalkyl, (cycloalkyl)alkyl, aryl, (aryl)alkyl, heterocyclo, (heterocyclo)alkyl, heteroaryl or (heteroaryl)alkyl, any of which may be independently substituted where valance allows with one to three groups $T^7$, $T^8$ and/or $T^9$; or
(ii) —$C(O)_rR^7$, —C(O)—C(O)—$C(O)OR^7$ or —$SO_2R^8$;
$R^6$ is alkyl, alkenyl, aryl, (aryl)alkyl, heteroaryl, (heteroaryl)alkyl, cycloalkyl, (cycloalkyl)alkyl, heterocyclo, or (heterocyclo)alkyl, any of which may be optionally independently substituted where valance allows with one to three groups $T^4$, $T^5$ and/or $T^6$;

R⁷ is
(i) H, alkyl, alkenyl, heterocyclo, (heterocyclo)alkyl, (hydroxy)alkyl, (alkoxy)alkyl, (aryloxy)alkyl, heteroaryl, aryl or (aryl)alkyl, any of which may be optionally independently substituted where valance allows with one to three groups $T^7$, $T^8$ and/or $T^9$; or
(ii) —$NR^9R^{10}$ or $(NR^9R^{10})$alkyl;

R⁸ is
(i) alkyl, alkenyl, heterocyclo, (heterocyclo)alkyl, (hydroxy)alkyl, (alkoxy)alkyl, (aryloxy)alkyl, heteroaryl, aryl or (aryl)alkyl, any of which may be optionally independently substituted where valance allows with one to three groups $T^7$, $T^8$ and/or $T^9$; or
(ii) —$NR^9R^{10}$ or $(NR^9R^{10})$alkyl;

$R^9$ and $R^{10}$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which may be optionally independently substituted where valance allows with one to three groups $T^7$, $T^8$ and/or $T^9$;

$T^4$, $T^5$, $T^6$, $T^7$, $T^8$ and $T^9$ are each independently
(i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, aryl, (aryl)alkyl, heterocyclo, (heterocyclo)alkyl, heteroaryl, (heteroaryl)alkyl, —$OT^{10}$, —SH, —$ST^{10}$, —C(O)H, —$C(O)_tT^{10}$, —O—$C(O)T^{10}$, -$T^{17}C(O)N(T^{11})T^{10}$, —$SO_3H$, —$S(O)_tT^{10}$, —$S(O)_tN(T^{11})T^{10}$, -$T^{12}$-$NT^{14}T^{15}$, -$T^{12}$-$N(T^{11})$-$T^{13}$-$NT^{14}T^{15}$, and -$T^{12}$-$N(T^{16})$-$T^{13}$-H; or
(ii) halo, cyano, nitro, OH, oxo, —SH, amino, —$OT^{10}$, —$ST^{10}$, —C(O)H, —$C(O)_tT^{10}$, —O—$C(O)T^{10}$, -$T^{17}C(O)N(T^{11})T^{10}$, —$SO_3H$, —$S(O)_tT^{10}$, —$S(O)_tN(T^{11})T^{10}$, -$T^{12}$-$NT^{14}T^{15}$, -$T^{12}$-$N(T^{11})$-$T^{13}$-$NT^{14}T^{15}$, or -$T^{12}$-$N(T^{16})$-$T^{13}$-H;

t is 1 or 2;

$T^{10}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{12}$ and $T^{13}$ are each independently a single bond, -$T^{17}$-S(O)$_t$-$T^{18}$-, -$T^{17}$-C(O)-$T^{18}$-, -$T^{17}$-C(S)-$T^{18}$-, -$T^{17}$-O-$T^{18}$-, -$T^{17}$-S-$T^{18}$-, -$T^{17}$-O—C(O)-$T^{18}$-, -$T^{17}$-C(O)$_tT^{18}$-, -$T^{17}$—C(=$NT^{19}$)-$T^{18}$- or -$T^{17}$-C(O)—C(O)-$T^{18}$-;

$T^{11}$, $T^{14}$, $T^{15}$, $T^{16}$ and $T^{19}$ are each independently
(i) hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —$ST^{22}$, —C(O)H, —$C(O)_tT^{22}$, —O—$C(O)T^{22}$ and —$S(O)_tT^{22}$; or
(ii) halo, cyano, nitro, OH, oxo, —SH, amino, —$OT^{22}$, —$ST^{22}$, —C(O)H, —$C(O)_tT^{22}$, —O—$C(O)T^{22}$, —$SO_3H$, or —$S(O)_tT^{22}$; or (iii) $T^{14}$ and $T^{15}$ may together be alkylene or alkenylene, completing a 3- to 8-membered saturated or unsaturated ring together with the atoms to which they are attached, which ring is substituted with one or more groups listed in the description of $T^{20}$; or
(iv) $T^{14}$ or $T^{15}$, together with $T^{11}$, may be alkylene or alkenylene completing a 3- to 8-membered saturated or unsaturated ring together with the nitrogen atoms to which they are attached, which ring is substituted with one or more groups listed in the description of $T^{20}$; or
(v) $T^{14}$ and $T^{15}$ or $T^{11}$ and $T^{16}$ together with the nitrogen atom to which they are attached may combine to form a group —N=$CT^{20}T^{21}$;

$T^{17}$ and $T^{18}$ are each independently a single bond, alkylene, alkenylene or alkynylene;

$T^{20}$ and $T^{21}$ are each
(i) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —$ST^{22}$, —C(O)H, —$C(O)_tT^{22}$, —O—$C(O)T^{22}$ and —$S(O)_tT^{22}$; or
(ii) halo, cyano, nitro, OH, oxo, —SH, amino, —$OT^{22}$, —$ST^{22}$, —C(O)H, —$C(O)_tT^{22}$, —O—$C(O)T^{22}$, —$SO_3H$, —$S(O)_tT^{22}$ or —$S(O)_tN(T^{11})T^{22}$; and $T^{22}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl.

2. A compound according to claim 1 having Formula (Ia)

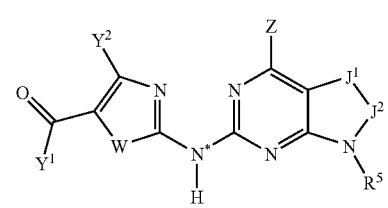

(Ia)

their enantiomers, diastereomers, and pharmaceutically acceptable salts thereof, wherein:
W is S;
$Y^1$ is —$NHT^{15}$ or $OT^{10}$;
$Y^2$ is alkyl or haloalkyl;
Z is —$NR^3R^4$ or halogen;
$J^1$ is optionally substituted $C_1$ alkylene;
$J^2$ is optionally substituted $C_1$ alkylene;
$R^3$ and $R^4$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which may be optionally independently substituted where valance allows with one to three groups $T^4$, $T^5$ and/or $T^6$;
or $R^3$ and $R^4$ may be taken together with the nitrogen atom to which they are attached to form a heterocyclo or heteroaryl ring, either of which is optionally independently substituted where valance allows with one to three groups independently selected from $T^4$, $T^5$ and/or $T^6$;

$R^5$ is
(i) H, cyano, alkyl, alkenyl, alkynyl, cycloalkyl, (cycloalkyl)alkyl, aryl, (aryl)alkyl, heterocyclo, (heterocyclo)alkyl, heteroaryl or (heteroaryl)alkyl, any of which may be independently substituted where valance allows with one to three groups $T^7$, $T^8$ and/or $T^9$; or
(ii) —C(O)$_t$R$^7$, —C(O)—C(O)—C(O)OR$^7$ or —SO$_2$R$^8$;

$R^7$ is
(i) H, alkyl, alkenyl, heterocyclo, (heterocyclo)alkyl, (hydroxy)alkyl, (alkoxy)alkyl, (aryloxy)alkyl, heteroaryl, aryl or (aryl)alkyl, any of which may be optionally independently substituted where valance allows with one to three groups $T^7$, $T^8$ and/or $T^9$; or
(ii) —NR$^9$R$^{10}$ or (NR$^9$R$^{10}$)alkyl;

$R^8$ is
(i) alkyl, alkenyl, heterocyclo, (heterocyclo)alkyl, (hydroxy)alkyl, (alkoxy)alkyl, (aryloxy)alkyl, heteroaryl, aryl or (aryl)alkyl, any of which may be optionally independently substituted where valance allows with one to three groups $T^7$, $T^8$ and/or $T^9$; or
(ii) —NR$^9$R$^{10}$ or (NR$^9$R$^{10}$)alkyl;

$R^9$ and $R^{10}$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl, any of which may be optionally independently substituted where valance allows with one to three groups $T^7$, $T^8$ and/or $T^9$;

$T^4$, $T^5$, $T^6$, $T^7$, $T^8$ and $T^9$ are each independently
(i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, aryl, (aryl)alkyl, heterocyclo, (heterocyclo)alkyl, heteroaryl, (heteroaryl)alkyl, —OT$^{10}$, —SH, —ST$^{10}$, —C(O)$_t$H, —C(O)$_t$T$^{10}$, —O—C(O)T$^{10}$, —SO$_3$H, —S(O)$_t$T$^{10}$, -T$^{17}$C(O)N(T$^{11}$)T$^{10}$, —S(O)$_t$N(T$^{11}$)T$^{10}$, -T$^{12}$-NT$^{14}$T$^{15}$, -T$^{12}$-N(T$^{11}$)-T$^{13}$-NT$^{14}$T$^{15}$, and -T$^{12}$-N(T$^{16}$)-T$^{13}$-H; or
(ii) halo, cyano, nitro, OH, oxo, —SH, amino, —OT$^{10}$, —ST$^{10}$, —C(O)$_t$H, —C(O)$_t$T$^{10}$, —O—C(O)T$^{10}$, -T$^{17}$C(O)N(T$^{11}$)T$^{10}$, —SO$_3$H, —S(O)$_t$T$^{10}$, —S(O)$_t$N(T$^{11}$)T$^{10}$, -T$^{12}$-NT$^{14}$T$^{15}$, -T$^{12}$-N(T$^{11}$)-T$^{13}$-NT$^{14}$T$^{15}$, or -T$^{12}$-N(T$^{16}$)-T$^{13}$-H;

t is 1 or 2;

$T^{10}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;

$T^{12}$ and $T^{13}$ are each independently a single bond, -T$^{17}$-S(O)$_t$-T$^{18}$-, -T$^{17}$-C(O)-T$^{18}$-, -T$^{17}$-C(S)-T$^{18}$-, -T$^{17}$-O-T$^{18}$-, -T$^{17}$-S-T$^{18}$-, -T$^{17}$-O—C(O)-T$^{18}$-, -T$^{17}$-C(O)$_t$T$^{18}$-, -T$^{17}$—C(=NT$^{19}$)-T$^{18}$- or -T$^{17}$-C(O)—C(O)-T$^{18}$-;

$T^{11}$, $T^{14}$, $T^{15}$, $T^{16}$ and $T^{19}$ are each independently
(i) hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —ST$^{22}$, —C(O)$_t$H, —C(O)$_t$T$^{22}$, —O—C(O)T$^{22}$ and —S(O)$_t$T$^{22}$ or
(ii) halo, cyano, nitro, OH, oxo, —SH, amino, —OT$^{22}$, —ST$^{22}$, —C(O)$_t$H, —C(O)$_t$T$^{22}$, —O—C(O)T$^{22}$, —SO$_3$H, or —S(O)$_t$T$^{22}$; or
(iii) $T^{14}$ and $T^{15}$ may together be alkylene or alkenylene, completing a 3- to 8-membered saturated or unsaturated ring together with the atoms to which they are attached, which ring is substituted with one or more groups listed in the description of $T^{20}$; or
(iv) $T^{14}$ or $T^{15}$, together with $T^{11}$, may be alkylene or alkenylene completing a 3- to 8-membered saturated or unsaturated ring together with the nitrogen atoms to which they are attached, which ring is substituted with one or more groups listed in the description of $T^{20}$; or
(v) $T^{14}$ and $T^{15}$ or $T^{11}$ and $T^{16}$ together with the nitrogen atom to which they are attached may combine to form a group —N=CT$^{20}$T$^{21}$;

$T^{17}$ and $T^{18}$ are each independently a single bond, alkylene, alkenylene or alkynylene;

$T^{20}$ and $T^{21}$ are each
(i) independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl, any of which may be optionally independently substituted where valence permits by one or more groups selected from alkyl, (hydroxy)alkyl, halo, cyano, nitro, OH, oxo, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, (heteroaryl)alkyl, —SH, —ST$^{22}$, —C(O)$_t$H, —C(O)$_t$T$^{22}$, —O—C(O)T$^{22}$ and —S(O)$_t$T$^{22}$; or
(ii) halo, cyano, nitro, OH, oxo, —SH, amino, —OT$^{22}$, —ST$^{22}$, —C(O)$_t$H, —C(O)$_t$T$^{22}$, —O—C(O)T$^{22}$, —SO$_3$H, —S(O)$_t$T$^{22}$ or —S(O)$_t$N(T$^{11}$)T$^{22}$; and $T^{22}$ is alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl.

3. A compound of claim 2, their enantiomers, diastereomers, and pharmaceutically acceptable salts thereof, wherein Z is selected from:

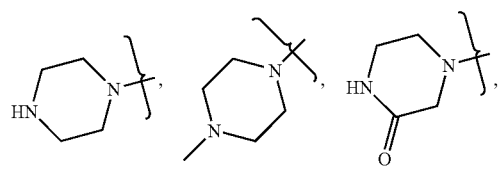

161
-continued
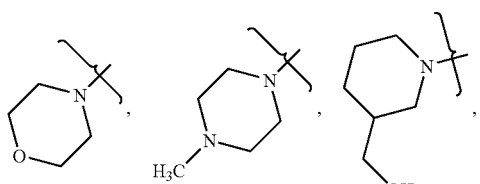
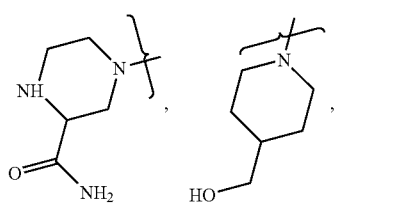
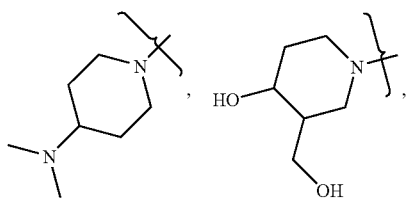
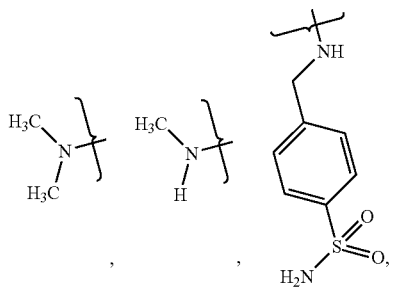
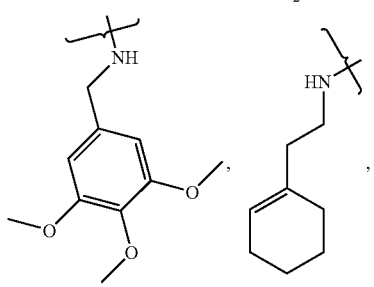
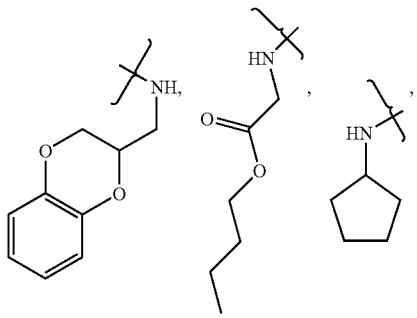
162
-continued
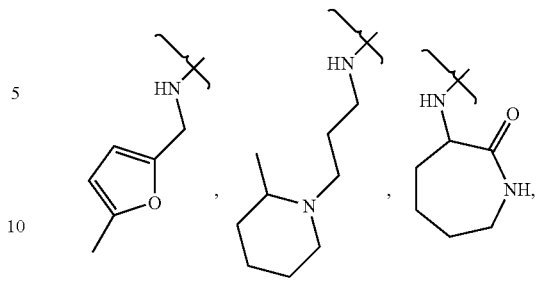
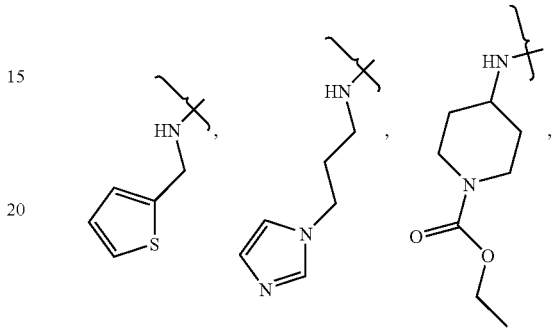
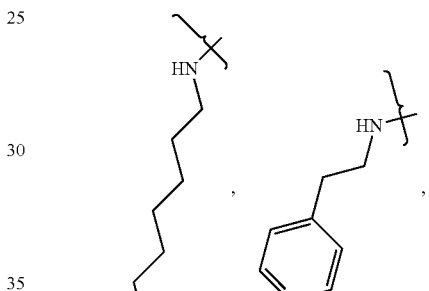
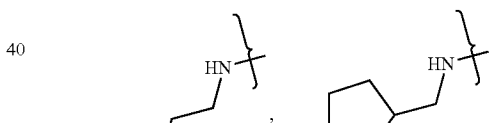
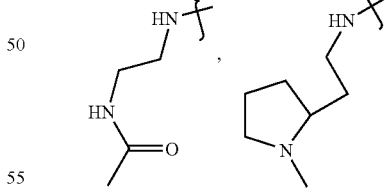
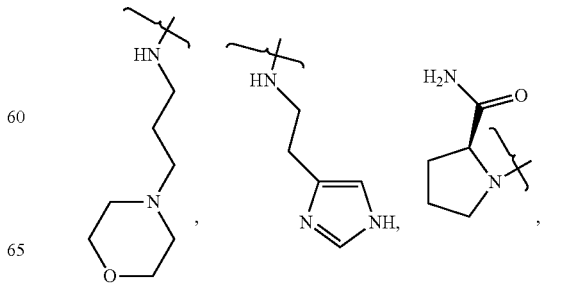

-continued
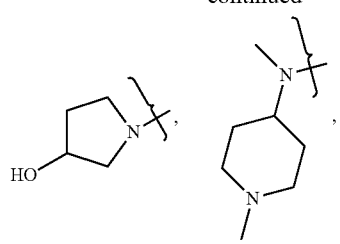
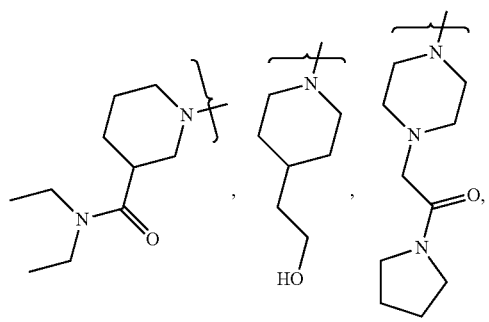
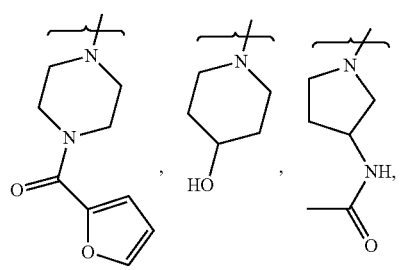
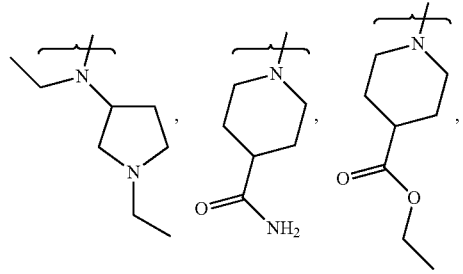
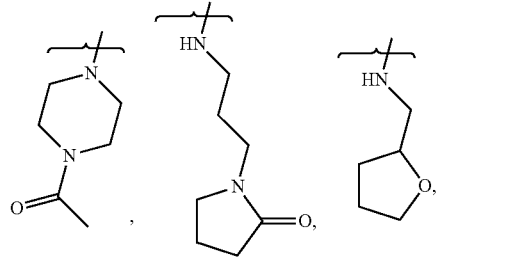
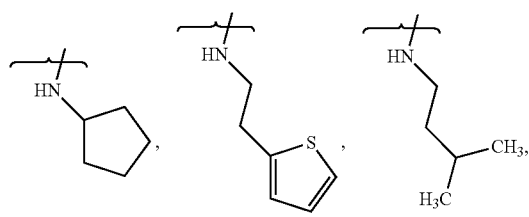
-continued
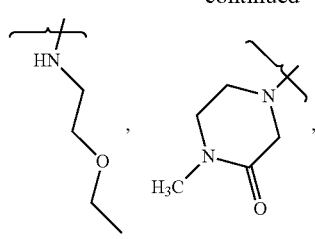
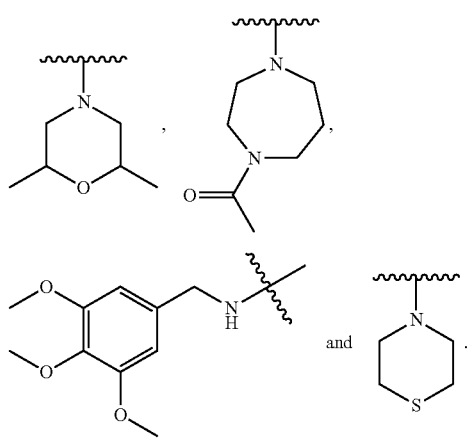
4. A compound of claim 2, their enantiomers, diastereomers, and pharmaceutically acceptable salts thereof, wherein $R^5$ is selected from:
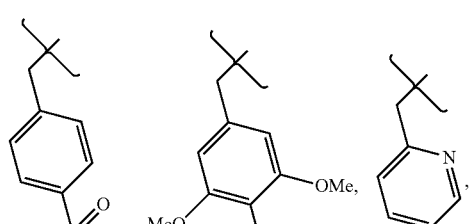
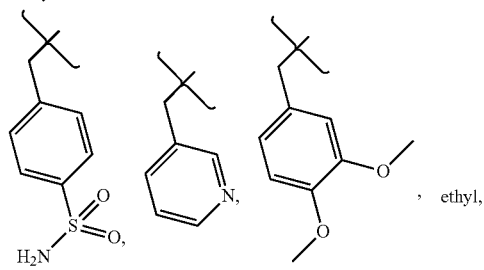
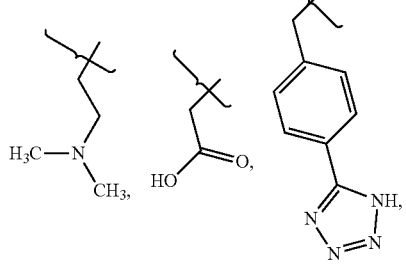

165
-continued
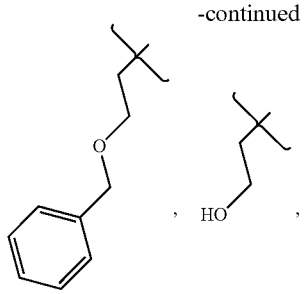
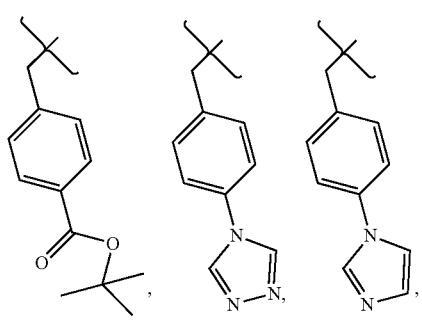
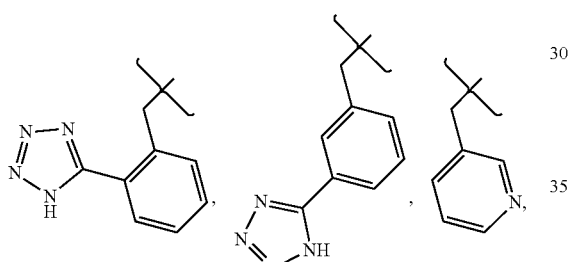
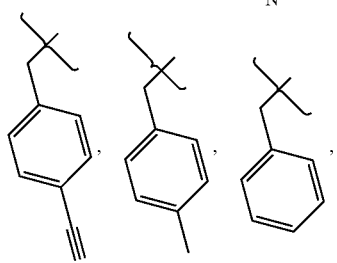
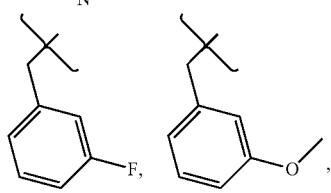
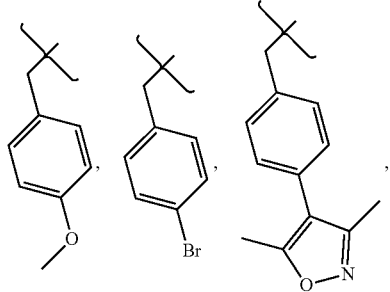
166
-continued
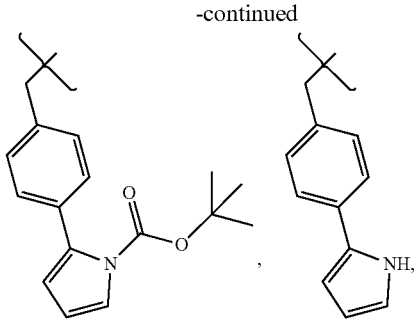
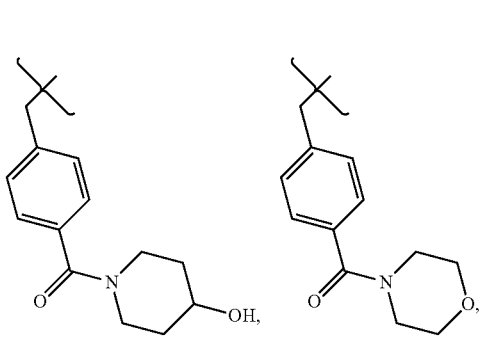
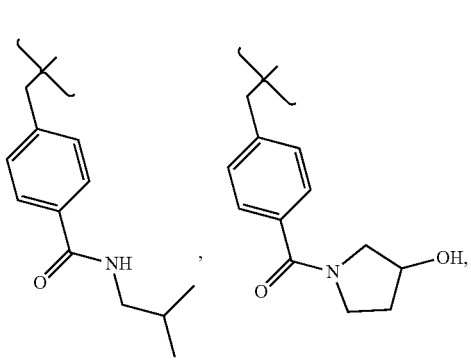
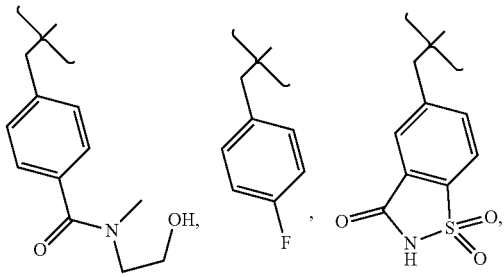
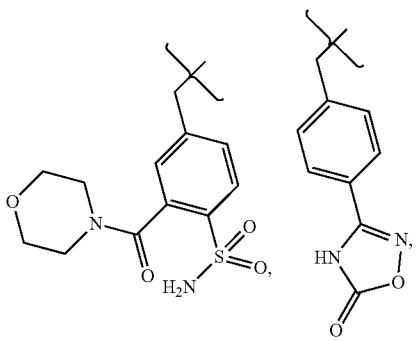

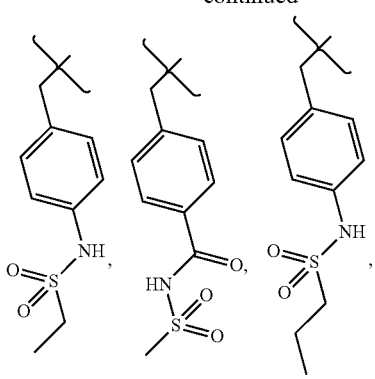
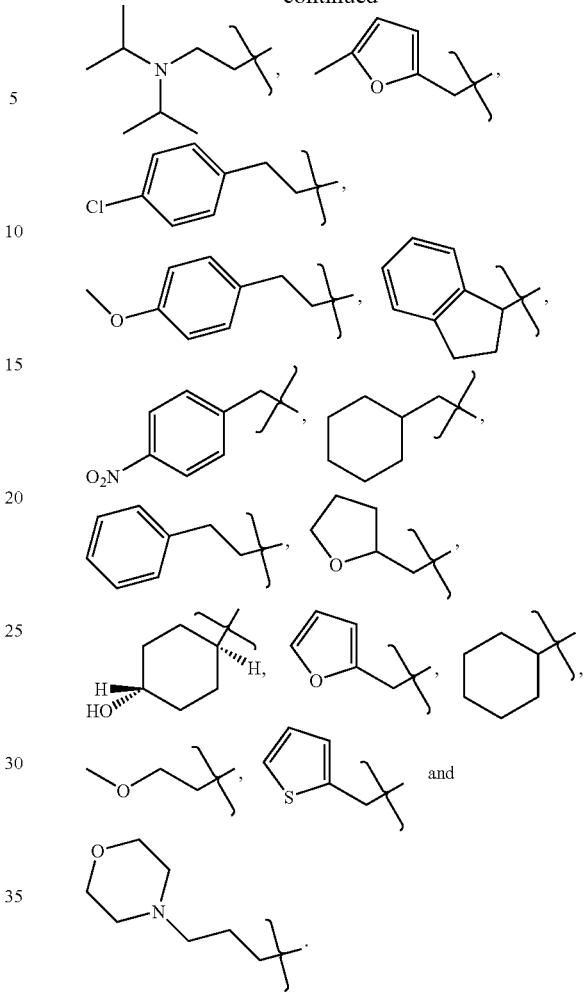
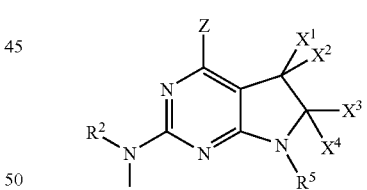

5. A compound of claim 1 having Formula (III)

$$\text{(III)}$$

their enantiomers, diastereomers, and pharmaceutically acceptable salts thereof, wherein:

$X^1$, $X^2$, $X^3$ and $X^4$ are
(i) independently chosen from hydrogen, $T^{10}$, $OT^{10}$ $NT^{14}T^{15}$; and/or
(ii) $X^3$ and $X^4$ may be taken together to be a carbonyl group.

6. A pharmaceutical composition comprising at least one compound of claim 1 and a pharmaceutically-acceptable carrier or diluent.

7. A method of treating leukocyte activation-associated disorders which comprises administering an effective amount of at least one compound of claim 1 to a patient in need thereof, wherein said disorder is transplant rejection, graph verses host disease, rheumatoid arthritis, multiple sclerosis, juvenile diabetes, asthma, inflammatory bowel disease, ischemic or reperfusion injury, cell proliferation, or psoriasis.

8. A compound selected from
i. 2-[4-(4-Hydroxy-piperidin-1-yl)-7-pyridin-2-ylmethyl-5,6-dihydro-pyrrolo[2,3-d]pyrimidin-2-ylamino]-4-methyl-thiazole-5-carboxylic acid ethyl ester;
2-[7-(4-Methanesulfonyl-benzyl)-4-piperazin-1-yl-5,6-dihydro-pyrrolo[2,3-d]pyrimidin-2-ylamino]-4-methyl-thiazole-5-carboxylic acid ethyl ester;
4-Methyl-2-[4-piperazin-1-yl-7-(3,4,5-trimethoxy-benzyl)-5,6-dihydro-pyrrolo[2,3-d]pyrimidin-2-ylamino]-thiazole-5-carboxylic acid ethyl ester;
4-Methyl-2-[4-(4-methyl-piperazin-1-yl)-7-(3,4,5-trimethoxy-benzyl)-5,6-dihydro-pyrrolo[2,3-d]pyrimidin-2-ylamino]-thiazole-5-carboxylic acid ethyl ester;
4-Methyl-2-[4-(3-oxo-piperazin-1-yl)-7-pyridin-2-ylmethyl-5,6-dihydro-pyrrolo[2,3-d]pyrimidin-2-ylamino]-thiazole-5-carboxylic acid ethyl ester;
2-[7-(4-Methanesulfonyl-benzyl)-4-(3-oxo-piperazin-1-yl)-5,6-dihydro-pyrrolo[2,3-d]pyrimidin-2-ylamino]-4-methyl-thiazole-5-carboxylic acid ethyl ester;
2-[7-(4-Methanesulfonyl-benzyl)-4-morpholin-4-yl-5,6-dihydro-pyrrolo[2,3-d]pyrimidin-2-ylamino]-4-methyl-thiazole-5-carboxylic acid ethyl ester;
2-[7-(4-Methanesulfonyl-benzyl)-4-(4-methyl-piperazin-1-yl)-5,6-dihydro-pyrrolo[2,3-d]pyrimidin-2-ylamino]-4-methyl-thiazole-5-carboxylic acid ethyl ester;
2-[4-(3-Hydroxymethyl-piperidin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester;
2-[4-(3-Carbamoyl-piperazin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester;
2-[4-(4-Hydroxymethyl-piperidin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester;
2-[4-(4-Dimethylamino-piperidin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester;
2-[4-(4-Hydroxy-3-hydroxymethyl-piperidin-1-yl)-7-(4-methanesulfonyl-benzyl)-5,6-dihydro-pyrrolo[2,3-d]pyrimidin-2-ylamino]-4-methyl-thiazole-5-carboxylic acid ethyl ester;
2-[4-Dimethylamino-7-(4-methanesulfonyl-benzyl)-5,6-dihydro-pyrrolo[2,3-d]pyrimidin-2-ylamino]-4-methyl-thiazole-5-carboxylic acid ethyl ester;
2-[7-(4-Methanesulfonyl-benzyl)-4-methylamino-5,6-dihydro-pyrrolo[2,3-d]pyrimidin-2-ylamino]-4-methyl-thiazole-5-carboxylic acid ethyl ester;
4-Methyl-2-[4-(3-oxo-piperazin-1-yl)-7-(4-sulfamoyl-benzyl)-5,6-dihydro-pyrrolo[2,3-d]pyrimidin-2-ylamino]-thiazole-5-carboxylic acid ethyl ester;
4-Methyl-2-[4-(3-oxo-piperazin-1-yl)-7-pyridin-3-ylmethyl-5,6-dihydro-pyrrolo[2,3-d]pyrimidin-2-ylamino]-thiazole-5-carboxylic acid ethyl ester;
2-[7-(3,4-Dimethoxy-benzyl)-4-(3-oxo-piperazin-1-yl)-5,6-dihydro-pyrrolo[2,3-d]pyrimidin-2-ylamino]-4-methyl-thiazole-5-carboxylic acid ethyl ester;
2-[7-Ethyl-4-(3-oxo-piperazin-1-yl)-5,6-dihydro-pyrrolo[2,3-d]pyrimidin-2-ylamino]-4-methyl-thiazole-5-carboxylic acid ethyl ester;
2-[7-Ethyl-4-(4-sulfamoyl-benzylamino)-5,6-dihydro-pyrrolo[2,3-d]pyrimidin-2-ylamino]-4-methyl-thiazole-5-carboxylic acid ethyl ester;
2-[7-(4-Cyano-benzyl)-4-(3-oxo-piperazin-1-yl)5,6-dihydro-pyrrolo[2,3-d]pyrimidin-2-ylamino]-4-methyl-thiazole-5-carboxylic acid ethyl ester;
2-[7-(2-Dimethylamino-ethyl)-4-(3-oxo-piperazin-1-yl)-5,6-dihydro-pyrrolo[2,3-d]pyrimidin-2-ylamino]-4-methyl-thiazole-5-carboxylic acid ethyl ester;
2-[7-Carboxymethyl-4-(3-oxo-piperazin-1-yl)-5,6-dihydro-pyrrolo[2,3-d]pyrimidin-2-ylamino]-4-methyl-thiazole-5-carboxylic acid ethyl ester;
2-[7-(2-Dimethylamino-ethyl)-4-(3,4,5-trimethoxy-benzylamino)-5,6-dihydro-pyrrolo[2,3-d]pyrimidin-2-ylamino]-4-methyl-thiazole-5-carboxylic acid ethyl ester;
4-Methyl-2-{4-(3-oxo-piperazin-1-yl)-7-[4-(1H-tetrazol-5-yl)-benzyl]-5,6-dihydro-pyrrolo[2,3-d]pyrimidin-2-ylamino}-thiazole-5-carboxylic acid ethyl ester;
2-[4-(2-Cyclohex-1-enyl-ethylamino)-7-pyridin-3-ylmethyl-5,6-dihydro-pyrrolo[2,3-d]pyrimidin-2-ylamino]-4-methyl-thiazole-5-carboxylic acid ethyl ester;
2-{4-[(2,3-Dihydro-benzo[1,4]dioxin-2-ylmethyl)-amino]-7-pyridin-3-ylmethyl-5,6-dihydro-pyrrolo[2,3-d]pyrimidin-2-ylamino}-4-methyl-thiazole-5-carboxylic acid ethyl ester;
2-[4-(Butoxycarbonylmethyl-amino)-7-pyridin-3-ylmethyl-5,6-dihydro-pyrrolo[2,3-d]pyrimidin-2-ylamino]-4-methyl-thiazole-5-carboxylic acid ethyl ester;
2-(4-Cyclopentylamino-7-pyridin-3-ylmethyl-5,6-dihydro-pyrrolo[2,3-d]pyrimidin-2-ylamino)-4-methyl-thiazole-5-carboxylic acid ethyl ester;
4-Methyl-2-{4-[(5-methyl-furan-2-ylmethyl)-amino]-7-pyridin-3-ylmethyl-5,6-dihydro-pyrrolo[2,3-d]pyrimidin-2-ylamino}-thiazole-5-carboxylic acid ethyl ester;
4-Methyl-2-{4-[3-(2-methyl-piperidin-1-yl)-propylamino]-7-pyridin-3-ylmethyl-5,6-dihydro-pyrrolo[2,3-d]pyrimidin-2-ylamino}-thiazole-5-carboxylic acid ethyl ester;
4-Methyl-2-[4-(2-oxo-azepan-3-ylamino)-7-pyridin-3-ylmethyl-5,6-dihydro-pyrrolo[2,3-d]pyrimidin-2-ylamino]-thiazole-5-carboxylic acid ethyl ester;
4-Methyl-2-{7-pyridin-3-ylmethyl-4-[(thiophen-2-ylmethyl)-amino]-5,6-dihydro-pyrrolo[2,3-d]pyrimidin-2-ylamino}-thiazole-5-carboxylic acid ethyl ester;
2-[4-(3-Imidazol-1-yl-propylamino)-7-pyridin-3-ylmethyl-5,6-dihydro-pyrrolo[2,3-d]pyrimidin-2-ylamino]-4-methyl-thiazole-5-carboxylic acid ethyl ester;
4-Methyl-2-[4-(1-carboxyethyl-piperidin-4-ylamino)-7-pyridin-3-ylmethyl-5,6-dihydro-pyrrolo[2,3-d]pyrimidin-2-ylamino]-thiazole-5-carboxylic acid ethyl ester;
2-[4-(6-Dimethylamino-hexylamino)-7-pyridin-3-ylmethyl-5,6-dihydro-pyrrolo[2,3-d]pyrimidin-2-ylamino]-4-methyl-thiazole-5-carboxylic acid ethyl ester;
4-Methyl-2-[4-(2-pyridin-4-yl-ethylamino)-7-pyridin-3-ylmethyl-5,6-dihydro-pyrrolo[2,3-d]pyrimidin-2-ylamino]-thiazole-5-carboxylic acid ethyl ester;
2-[4-(4-Hydroxy-butylamino)-7-pyridin-3-ylmethyl-5,6-dihydro-pyrrolo[2,3-d]pyrimidin-2-ylamino]-4-methyl-thiazole-5-carboxylic acid ethyl ester;

2-{4-[(1-Ethyl-pyrrolidin-2-ylmethyl)-amino]-7-pyridin-3-ylmethyl-5,6-dihydro-pyrrolo[2,3-d]pyrimidin-2-ylamino}-4-methyl-thiazole-5-carboxylic acid ethyl ester;

2-[4-(2-Acetylamino-ethylamino)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-{4-[2-(1-methyl-pyrrolidin-2-yl)-ethylamino]-7-pyridin-3-ylmethyl-5,6-dihydro-pyrrolo[2,3-d]pyrimidin-2-ylamino}-thiazole-5-carboxylic acid ethyl ester;

2-[4-(1-Hydroxymethyl-butylamino)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-[4-(3-morpholin-4-yl-propylamino)-7-pyridin-3-ylmethyl-5,6-dihydro-pyrrolo[2,3-d]pyrimidin-2-ylamino]-thiazole-5-carboxylic acid ethyl ester;

2-{4-[2-(1H-Imidazol-4-yl)-ethylamino]-7-pyridin-3-ylmethyl-5,6-dihydro-pyrrolo[2,3-d]pyrimidin-2-ylamino}-4-methyl-thiazole-5-carboxylic acid ethyl ester;

2-[4-{(S)-2-Carbamoyl-pyrrolidin-1-yl}-7-pyridin-3-ylmethyl-5,6-dihydro-pyrrolo[2,3-d]pyrimidin-2-ylamino]-4-methyl-thiazole-5-carboxylic acid ethyl ester;

2-[4-(3-Hydroxy-pyrrolidin-1-yl)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-(4-morpholin-4-yl-7-pyridin-3-ylmethyl-5,6-dihydro-pyrrolo[2,3-d]pyrimidin-2-ylamino)-thiazole-5-carboxylic acid ethyl ester;

4-Methyl-2-{4-[methyl-(1-methyl-piperidin-4-yl)-amino]-7-pyridin-3-ylmethyl-5,6-dihydro-pyrrolo[2,3-d]pyrimidin-2-ylamino}-thiazole-5-carboxylic acid ethyl ester;

2-[4-(3-Diethylcarbamoyl-piperidin-1-yl)-7-pyridin-3-ylmethyl-5,6-dihydro-pyrrolo[2,3-d]pyrimidin-2-ylamino]-4-methyl-thiazole-5-carboxylic acid ethyl ester;

2-{4-[4-(2-Hydroxy-ethyl)-piperidin-1-yl]-7-pyridin-3-ylmethyl-5,6-dihydro-pyrrolo[2,3-d]pyrimidin-2-ylamino}-4-methyl-thiazole-5-carboxylic acid ethyl ester;

4-Methyl-2-{4-[4-(2-oxo-2-pyrrolidin-1-yl-ethyl)-piperazin-1-yl]-7-pyridin-3-ylmethyl-5,6-dihydro-pyrrolo[2,3-d]pyrimidin-2-ylamino}-thiazole-5-carboxylic acid ethyl ester;

2-{4-[4-(Furan-2-carbonyl)-piperazin-1-yl]-7-pyridin-3-ylmethyl-5,6-dihydro-pyrrolo[2,3-d]pyrimidin-2-ylamino}-4-methyl-thiazole-5-carboxylic acid ethyl ester;

2-[4-(4-Hydroxy-piperidin-1-yl)-7-pyridin-3-ylmethyl-5,6-dihydro-pyrrolo[2,3-d]pyrimidin-2-ylamino]-4-methyl-thiazole-5-carboxylic acid ethyl ester;

2-[4-(3-Acetylamino-pyrrolidin-1-yl)-7-pyridin-3-ylmethyl-5,6-dihydro-pyrrolo[2,3-d]pyrimidin-2-ylamino]-4-methyl-thiazole-5-carboxylic acid ethyl ester;

2-{4-[Ethyl-(1-ethyl-pyrrolidin-3-yl)-amino]-7-pyridin-3-ylmethyl-5,6-dihydro-pyrrolo[2,3-d]pyrimidin-2-ylamino}-4-methyl-thiazole-5-carboxylic acid ethyl ester;

2-[4-(4-Carbamoyl-piperidin-1-yl)-7-pyridin-3-ylmethyl-5,6-dihydro-pyrrolo[2,3-d]pyrimidin-2-ylamino]-4-methyl-thiazole-5-carboxylic acid ethyl ester;

4-Methyl-2-[4-(4-carboxyethyl-piperidin-1-yl)-7-pyridin-3-ylmethyl-5,6-dihydro-pyrrolo[2,3-d]pyrimidin-2-ylamino]-thiazole-5-carboxylic acid ethyl ester;

2-[4-(4-Acetyl-piperazin-1-yl)-7-pyridin-3-ylmethyl-5,6-dihydro-pyrrolo[2,3-d]pyrimidin-2-ylamino]-4-methyl-thiazole-5-carboxylic acid ethyl ester;

2-[7-(2-Benzyloxy-ethyl)-4-(3-oxo-piperazin-1-yl)-5,6-dihydro-pyrrolo[2,3-d]pyrimidin-2-ylamino]-4-methyl-thiazole-5-carboxylic acid ethyl ester;

2-[7-(2-Hydroxy-ethyl)-4-(3-oxo-piperazin-1-yl)-5,6-dihydro-pyrrolo[2,3-d]pyrimidin-2-ylamino]-4-methyl-thiazole-5-carboxylic acid ethyl ester;

2-{4-(4-Hydroxy-piperidin-1-yl)-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester;

4-Methyl-2-{4-[3-(2-oxo-pyrrolidin-1-yl)-propylamino]-7-[4-(1H-tetrazol-5-yl)-benzyl]-5,6-dihydro-pyrrolo[2,3-d]pyrimidin-2-ylamino}-thiazole-5-carboxylic acid ethyl ester;

4-Methyl-2-{4-morpholin-4-yl-7-[4-(1H-tetrazol-5-yl)-benzyl]-5,6-dihydro-pyrrolo[2,3-d]pyrimidin-2-ylamino}-thiazole-5-carboxylic acid ethyl ester;

2-[7-(4-tert-Butoxycarbonyl-benzyl)-4-(3-oxo-piperazin-1-yl)-5,6-dihydro-pyrrolo[2,3-d]pyrimidin-2-ylamino]-4-methyl-thiazole-5-carboxylic acid ethyl ester;

2-[7-(4-Carboxy-benzyl)-4-(3-oxo-piperazin-1-yl)-5,6-dihydro-pyrrolo[2,3-d]pyrimidin-2-ylamino]-4-methyl-thiazole-5-carboxylic acid ethyl ester;

4-Methyl-2-{4-[(tetrahydro-furan-2-ylmethyl)-amino]-7-[4-(1H-tetrazol-5-yl)-benzyl]-5,6-dihydro-pyrrolo[2,3-d]pyrimidin-2-ylamino}-thiazole-5-carboxylic acid ethyl ester;

2-{4-Cyclopentylamino-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester;

2-{4-(4-Hydroxy-butylamino)-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester;

4-Methyl-2-[7-[4-(1H-tetrazol-5-yl)-benzyl]-4-(2-thiophen-2-yl-ethylamino)-5,6-dihydro-pyrrolo[2,3-d]pyrimidin-2-ylamino]-thiazole-5-carboxylic acid ethyl ester;

4-Methyl-2-{4-(3-methyl-butylamino)-7-[4-(1H-tetrazol-5-yl)-benzyl]-5,6-dihydro-pyrrolo[2,3-d]pyrimidin-2-ylamino}-thiazole-5-carboxylic acid ethyl ester;

2-{4-(2-Ethoxy-ethylamino)-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester;

2-{4-(3-Hydroxymethyl-piperidin-1-yl)-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester;

ii. the enantiomers, diastereomers, and pharmaceutically acceptable salts of each of (i).

9. A compound selected from i.     4-Methyl-2-[4-morpholin-4-yl-6-oxo-7-(3,4,5-trimethoxy-benzyl)-5,6-dihydro-pyrrolo[2,3-d]pyrimidin-2-ylamino]-thiazole-5-carboxylic acid ethyl ester;

4-Methyl-2-[6-oxo-4-(3-oxo-piperazin-1-yl)-7-(4-sulfamoyl-benzyl)-5,6-dihydro-pyrrolo[2,3-d]pyrimidin-2-ylamino]-thiazole-5-carboxylic acid ethyl ester;

2-[7-(4-Methanesulfonyl-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester;

2-[4-(4-Hydroxy-piperidin-1-yl)-6-oxo-7-(3,4,5-trimethoxy-benzyl)-5,6-dihydro-pyrrolo[2,3-d]pyrimidin-2-ylamino]-4-methyl-thiazole-5-carboxylic acid ethyl ester;

4-Methyl-2-[6-oxo-4-(3-oxo-piperazin-1-yl)-7-(3,4,5-trimethoxy-benzyl)-5,6-dihydro-pyrrolo[2,3-d]pyrimidin-2-ylamino]-thiazole-5-carboxylic acid ethyl ester;

4-Methyl-2-[4-morpholin-4-yl-6-oxo-7-(4-sulfamoyl-benzyl)-5,6-dihydro-pyrrolo[2,3-d]pyrimidin-2-ylamino]-thiazole-5-carboxylic acid ethyl ester;

2-[4-(4-Hydroxy-piperidin-1-yl)-6-oxo-7-(4-sulfamoyl-benzyl)-5,6-dihydro-pyrrolo[2,3-d]pyrimidin-2-ylamino]-4-methyl-thiazole-5-carboxylic acid ethyl ester;

4-Methyl-2-[4-(4-methyl-3-oxo-piperazin-1-yl)-6-oxo-7-(4-sulfamoyl-benzyl)-5,6-dihydro-pyrrolo[2,3-d]pyrimidin-2-ylamino]-thiazole-5-carboxylic acid ethyl ester;

4-Methyl-2-[6-oxo-4-(3-oxo-piperazin-1-yl)-7-(4-[1,2,4]triazol-4-yl-benzyl)-5,6-dihydro-pyrrolo[2,3-d]pyrimidin-2-ylamino]-thiazole-5-carboxylic acid ethyl ester;

2-[7-(4-Imidazol-1-yl-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester;

4-Methyl-2-{6-oxo-4-(3-oxo-piperazin-1-yl)-7-[2-(1H-tetrazol-5-yl)-benzyl]-5,6-dihydro-pyrrolo[2,3-d]pyrimidin-2-ylamino}-thiazole-5-carboxylic acid ethyl ester;

2-{4-(4-Hydroxy-piperidin-1-yl)-6-oxo-7-[2-(1H-tetrazol-5-yl)-benzyl]-5,6-dihydro-pyrrolo[2,3-d]pyrimidin-2-ylamino}-4-methyl-thiazole-5-carboxylic acid ethyl ester;

4-Methyl-2-{6-oxo-4-(3-oxo-piperazin-1-yl)-7-[3-(1H-tetrazol-5-yl)-benzyl]-5,6-dihydro-pyrrolo[2,3-d]pyrimidin-2-ylamino}-thiazole-5-carboxylic acid ethyl ester;

4-Methyl-2-[6-oxo-4-(3-oxo-piperazin-1-yl)-7-pyridin-3-ylmethyl-5,6-dihydro-pyrrolo[2,3-d]pyrimidin-2-ylamino]-thiazole-5-carboxylic acid ethyl ester;

2-{4-(4-Hydroxy-piperidin-1-yl)-6-oxo-7-[3-(1H-tetrazol-5-yl)-benzyl]-5,6-dihydro-pyrrolo[2,3-d]pyrimidin-2-ylamino}-4-methyl-thiazole-5-carboxylic acid ethyl ester;

4-Methyl-2-[6-oxo-4-(3-oxo-piperazin-1-yl)-7-pyridin-2-ylmethyl-5,6-dihydro-pyrrolo[2,3-d]pyrimidin-2-ylamino]-thiazole-5-carboxylic acid ethyl ester;

2-[4-(4-Hydroxy-piperidin-1-yl)-6-oxo-7-pyridin-3-ylmethyl-5,6-dihydro-pyrrolo[2,3-d]pyrimidin-2-ylamino]-4-methyl-thiazole-5-carboxylic acid ethyl ester;

2-[4-(4-Hydroxy-piperidin-1-yl)-6-oxo-7-pyridin-2-ylmethyl-5,6-dihydro-pyrrolo[2,3-d]pyrimidin-2-ylamino]-4-methyl-thiazole-5-carboxylic acid ethyl ester;

4-Methyl-2-[6-oxo-4-(3-oxo-piperazin-1-yl)-7-pyridin-4-ylmethyl-5,6-dihydro-pyrrolo[2,3-d]pyrimidin-2-ylamino]-thiazole-5-carboxylic acid ethyl ester;

4-Methyl-2-(4-morpholin-4-yl-6-oxo-7-pyridin-4-ylmethyl-5,6-dihydro-pyrrolo[2,3-d]pyrimidin-2-ylamino)-thiazole-5-carboxylic acid ethyl ester;

2-[4-(4-Hydroxy-piperidin-1-yl)-6-oxo-7-pyridin-4-ylmethyl-5,6-dihydro-pyrrolo[2,3-d]pyrimidin-2-ylamino]-4-methyl-thiazole-5-carboxylic acid ethyl ester;

4-Methyl-2-{6-oxo-4-(3-oxo-piperazin-1-yl)-7-[4-(1H-tetrazol-5-yl)-benzyl]-5,6-dihydro-pyrrolo[2,3-d]pyrimidin-2-ylamino}-thiazole-5-carboxylic acid ethyl ester;

2-{4-(4-Hydroxy-piperidin-1-yl)-6-oxo-7-[4-(1H-tetrazol-5-yl)-benzyl]-5,6-dihydro-pyrrolo[2,3-d]pyrimidin-2-ylamino}-4-methyl-thiazole-5-carboxylic acid ethyl ester;

4-Methyl-2-{4-morpholin-4-yl-6-oxo-7-[4-(1H-tetrazol-5-yl)-benzyl]-5,6-dihydro-pyrrolo[2,3-d]pyrimidin-2-ylamino}-thiazole-5-carboxylic acid ethyl ester;

2-[7-(4-Cyano-benzyl)-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester;

2-[4-(4-Hydroxy-piperidin-1-yl)-7-(4-methyl-benzyl)-6-oxo-5,6-dihydro-pyrrolo[2,3-d]pyrimidin-2-ylamino]-4-methyl-thiazole-5-carboxylic acid ethyl ester;

2-[7-Benzyl-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester;

2-[7-(3-Fluoro-benzyl)-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester;

2-[4-(4-Hydroxy-piperidin-1-yl)-7-(3-methoxy-benzyl)-6-oxo-5,6-dihydro-pyrrolo[2,3-d]pyrimidin-2-ylamino]-4-methyl-thiazole-5-carboxylic acid ethyl ester;

2-[7-(3,4-Dimethoxy-benzyl)-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester;

2-[4-(4-Hydroxy-piperidin-1-yl)-7-(4-methoxy-benzyl)-6-oxo-5,6-dihydro-pyrrolo[2,3-d]pyrimidin-2-ylamino]-4-methyl-thiazole-5-carboxylic acid ethyl ester;

2-[7-(4-Bromo-benzyl)-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester;

2-[4-(4-Hydroxy-piperidin-1-yl)-6-oxo-7-(4-thiophen-3-yl-benzyl)-5,6-dihydro-pyrrolo[2,3-d]pyrimidin-2-ylamino]-4-methyl-thiazole-5-carboxylic acid ethyl ester;

2-[7-[4-(3,5-Dimethyl-isoxazol-4-yl)-benzyl]-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester;

2-[7-[4-(1-tert-Butoxycarbonyl-1H-pyrrol-2-yl)-benzyl]-4-(4-hydroxy-piperidin-1-yl)-6-oxo-5,6-dihydro-pyrrolo[2,3-d]pyrimidin-2-ylamino]-4-methyl-thiazole-5-carboxylic acid ethyl ester;

2-{4-(4-Hydroxy-piperidin-1-yl)-6-oxo-7-[4-(1H-pyrrol-2-yl)-benzyl]-5,6-dihydro-pyrrolo[2,3-d]pyrimidin-2-ylamino}-4-methyl-thiazole-5-carboxylic acid ethyl ester;

2-[7-(4-Carboxy-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester;

2-[7-(4-Dimethylcarbamoyl-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester;

2-[7-[4-(4-Hydroxy-piperidine-1-carbonyl)-benzyl]-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester;

4-Methyl-2-[7-[4-(morpholine-4-carbonyl)-benzyl]-6-oxo-4-(3-oxo-piperazin-1-yl)-5,6-dihydro-pyrrolo[2,3-d]pyrimidin-2-ylamino]-thiazole-5-carboxylic acid ethyl ester;

2-[7-(4-Isobutylcarbamoyl-benzyl)-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester;

2-[7-[4-(3-Hydroxy-pyrrolidine-1-carbonyl)-benzyl]-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester; and 2-[7-{4-[(2-Hydroxy-ethyl)-methyl-carbamoyl]-benzyl}-6-oxo-4-(3-oxo-piperazin-1-yl)-5,6-dihydro-pyrrolo[2,3-d]pyrimidin-2-ylamino]-4-methyl-thiazole-5-carboxylic acid ethyl ester; or ii. the enantiomers, diastereomers, and pharmaceutically acceptable salts of each of (i).

* * * * *

UNITED STATES PATENT AND TRADEMARK OFFICE
CERTIFICATE OF CORRECTION

PATENT NO.         : 7,981,881 B2                                      Page 1 of 1
APPLICATION NO.    : 12/050227
DATED              : July 19, 2011
INVENTOR(S)        : Joseph Barbosa et al.

It is certified that error appears in the above-identified patent and that said Letters Patent is hereby corrected as shown below:

In the Claims:

Claim 8:

Column 165, lines 30 to 36, change " 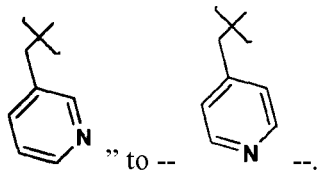 " to -- 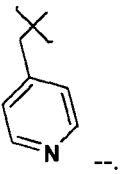 --.

Signed and Sealed this
Twenty-fourth Day of July, 2012

David J. Kappos
*Director of the United States Patent and Trademark Office*